United States Patent
Maglia et al.

(10) Patent No.: US 10,802,015 B2
(45) Date of Patent: *Oct. 13, 2020

(54) NANOPORE BIOSENSORS FOR DETECTION OF PROTEINS AND NUCLEIC ACIDS

(71) Applicant: Katholieke Universiteit Leuven, Leuven (BE)

(72) Inventors: Giovanni Maglia, Assen (NL); Mikhael Soskine, Leuven (BE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,475

(22) Filed: Jul. 24, 2019

(65) Prior Publication Data

US 2019/0346431 A1 Nov. 14, 2019

Related U.S. Application Data

(63) Continuation of application No. 15/984,974, filed on May 21, 2018, now Pat. No. 10,514,378, which is a continuation of application No. 14/779,895, filed as application No. PCT/BE2014/000013 on Mar. 25, 2014, now Pat. No. 10,006,905.

(60) Provisional application No. 61/805,068, filed on Mar. 25, 2013.

(30) Foreign Application Priority Data

Jul. 29, 2013 (GB) .................................. 1313477.0

(51) Int. Cl.
| | | |
|---|---|---|
| *G01N 33/543* | (2006.01) | |
| *C07K 14/255* | (2006.01) | |
| *C12Q 1/6869* | (2018.01) | |
| *C12Q 1/68* | (2018.01) | |
| *G01N 27/327* | (2006.01) | |
| *G01N 33/487* | (2006.01) | |

(52) U.S. Cl.
CPC ..... *G01N 33/54306* (2013.01); *C07K 14/255* (2013.01); *C12Q 1/68* (2013.01); *C12Q 1/6869* (2013.01); *G01N 27/3278* (2013.01); *G01N 33/48721* (2013.01)

(58) Field of Classification Search
CPC ....... G01N 33/54306; G01N 33/48721; G01N 27/3278; C12Q 1/68; C12Q 1/6869; C07K 14/255
See application file for complete search history.

(56) References Cited

U.S. PATENT DOCUMENTS

| | | |
|---|---|---|
| 5,795,782 A | 8/1998 | Church et al. |
| 6,015,714 A | 1/2000 | Baldarelli et al. |
| 6,114,121 A | 9/2000 | Fujiwara et al. |
| 6,362,002 B1 | 3/2002 | Denison et al. |
| 6,426,231 B1 | 7/2002 | Bayley et al. |
| 6,627,067 B1 | 9/2003 | Branton et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,588,079 B2 | 3/2017 | Gundlach et al. |
| 9,732,381 B2 | 8/2017 | Stoddart et al. |
| 9,751,915 B2 | 9/2017 | Clarke et al. |
| 9,777,049 B2 | 10/2017 | Bruce et al. |
| 10,006,905 B2 | 6/2018 | Maglia et al. |
| 10,167,503 B2 | 1/2019 | Clarke et al. |
| 10,266,885 B2 | 4/2019 | Jayasinghe et al. |
| 10,385,389 B2 | 8/2019 | Heron et al. |
| 10,400,014 B2 | 9/2019 | Howorka et al. |
| 10,443,097 B2 | 10/2019 | Jayasinghe et al. |
| 10,472,673 B2 | 11/2019 | Maglia et al. |
| 10,514,378 B2 | 12/2019 | Maglia et al. |
| 2002/0028458 A1 | 3/2002 | Lexow |
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |

(Continued)

FOREIGN PATENT DOCUMENTS

| | | |
|---|---|---|
| CA | 2381139 A1 | 3/2001 |
| CN | 102116783 A | 7/2011 |

(Continued)

OTHER PUBLICATIONS

[No Author Listed] Helicos BioSciences Corporation, "Helicos Genetic Analysis System," Specification Sheet retrieved online at: www.helicosbio.com/Portals/0/Documents/Helicos_SalesSpec.pdf, 4 pages (2008).

Ahern, Biochemical, reagents kits offer scientists good return on investment. The Scientist. Jul. 24, 1995;9(15):20.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

(Continued)

*Primary Examiner* — Ruixiang Li
(74) *Attorney, Agent, or Firm* — Wolf, Greenfield & Sacks, P.C.

(57) ABSTRACT

Described herein are nanopore biosensors based on a modified cytolysin protein. The nanopore biosensors accommodate macromolecules including proteins and nucleic acids, and may additionally comprise ligands with selective binding properties.

17 Claims, 24 Drawing Sheets

Specification includes a Sequence Listing.

(56) References Cited

U.S. PATENT DOCUMENTS

| | | |
|---|---|---|
| 2003/0211502 A1 | 11/2003 | Sauer et al. |
| 2003/0215881 A1 | 11/2003 | Bayley et al. |
| 2004/0214177 A1 | 10/2004 | Bension |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0311582 A1 | 12/2008 | Bayley et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0175663 A1 | 6/2015 | Yokoi et al. |
| 2015/0177237 A1 | 6/2015 | Turner et al. |
| 2015/0346149 A1 | 12/2015 | Brown et al. |
| 2016/0010147 A1 | 1/2016 | Heron et al. |
| 2016/0005330 A1 | 2/2016 | Maglia et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0209952 A1 | 7/2018 | Maglia et al. |
| 2018/0334707 A1 | 11/2018 | Stoddart et al. |
| 2018/0335425 A1 | 11/2018 | Maglia et al. |
| 2018/0364214 A1 | 12/2018 | Maglia et al. |
| 2019/0071721 A1 | 3/2019 | Jayasinghe et al. |
| 2019/0300582 A1 | 10/2019 | Jayasinghe et al. |
| 2019/0330282 A1 | 10/2019 | Jayasinghe et al. |
| 2020/0017556 A1 | 1/2020 | Howorka et al. |

FOREIGN PATENT DOCUMENTS

| | | |
|---|---|---|
| EP | 2682460 | 1/2014 |
| GB | 2453377 | 4/2009 |
| JP | H10-146190 | 6/1998 |
| JP | 2005-253427 | 9/2005 |
| JP | 2015-514128 A | 5/2015 |
| WO | WO 1999/005167 | 2/1999 |
| WO | WO 2000/028312 | 5/2000 |
| WO | WO 2001/042782 | 6/2001 |
| WO | WO 2001/059453 | 8/2001 |
| WO | WO 2002/042496 | 5/2002 |
| WO | WO 2003/095669 | 11/2003 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2008/102120 | 8/2008 |
| WO | WO 2008/102121 | 8/2008 |
| WO | WO 2008/124107 | 10/2008 |
| WO | WO 2009/024775 A1 | 2/2009 |
| WO | WO 2009/035647 | 3/2009 |
| WO | WO 2009/044170 A1 | 4/2009 |
| WO | WO 2009/077734 A2 | 6/2009 |
| WO | WO 2009/143425 A1 | 11/2009 |
| WO | WO 2010/004265 | 1/2010 |
| WO | WO 2010/004273 | 1/2010 |
| WO | WO 2010/034018 | 3/2010 |
| WO | WO 2010/055307 A1 | 5/2010 |
| WO | WO 2010/086602 A1 | 8/2010 |
| WO | WO 2010/086603 | 8/2010 |
| WO | WO 2010/086622 | 8/2010 |
| WO | WO 2010/122293 | 10/2010 |
| WO | WO 2011/067559 | 6/2011 |
| WO | WO 2012/042226 | 4/2012 |
| WO | WO 2012/107778 A2 | 8/2012 |
| WO | WO 2012/164270 A1 | 12/2012 |
| WO | WO 2013/014451 | 1/2013 |
| WO | WO 2013/057495 | 4/2013 |
| WO | WO 2013/098561 | 7/2013 |
| WO | WO 2013/098562 | 7/2013 |
| WO | WO 2013/109970 A1 | 7/2013 |
| WO | WO 2013/153359 | 10/2013 |
| WO | WO 2014/013259 | 1/2014 |
| WO | WO 2014/013260 | 1/2014 |
| WO | WO 2014/013262 | 1/2014 |
| WO | WO 2014/153625 A1 | 2/2014 |
| WO | WO 2014/135838 | 9/2014 |
| WO | WO 2015/022544 | 2/2015 |
| WO | WO 2015/055981 | 4/2015 |
| WO | WO 2015/110777 | 7/2015 |
| WO | WO 2015/124935 | 8/2015 |
| WO | WO 2015/150786 | 10/2015 |
| WO | WO 2015/150787 | 10/2015 |

OTHER PUBLICATIONS

Aoki et al., Single channel properties of lysenin measured in artificial lipid bilayers and their applications to biomolecule detection. Proc Jpn Acad Ser B Phys Biol Sci. 2010;86(9):920-5.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Atkins et al., Structure-function relationships of a novel bacterial toxin, hemolysin E. The role of alpha G. J Biol Chem. Dec. 29, 2000;275(52):41150-5.

Avrameas, Coupling of enzymes to proteins with glutaraldehyde. Use of the conjugates for the detection of antigens and antibodies. Immunochemistry. Jan. 1969;6(1):43-52.

Bayley et al., Stochastic sensors inspired by biology. Nature. Sep. 13, 2001;413(6852):226-30.

Bayley et al., Wrestling with native chemical ligation. ACS Chem Biol. Dec. 18, 2009;4(12):983-5. doi: 10.1021/cb900304p.

Bayley, Membrane-protein structure: Piercing insights. Nature. Jun. 4, 2009;459(7247):651-2. doi: 10.1038/459651a.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bianco et al., Helicase unwinding: active or merely perfect? J Mol Biol. Jul. 13, 2012;420(3):139-40. doi: 10.1016/j.jmb.2012.04.030. Epub May 2, 2012.

(56) References Cited

OTHER PUBLICATIONS

Bourdon et al., Molecular cloning and sequence analysis of a chondroitin sulfate proteoglycan cDNA. Proc Natl Acad Sci U S A. Mar. 1985;82(5):1321-5.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Byrd et al., Dda helicase tightly couples translocation on single-stranded DNA to unwinding of duplex DNA: Dda is an optimally active helicase. J Mol Biol. Jul. 13, 2012;420(3):141-54. doi:10.1016/j.jmb.2012.04.007. Epub Apr. 11, 2012.
Cao et al., Structure of the nonameric bacterial amyloid secretion channel. Proc Natl Acad Sci U S A. Dec. 16, 2014;111(50):E5439-44. doi: 10.1073/pnas.1411942111. Epub Dec. 1, 2014.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., A Novel DNA Sensing Technique Using Nanopore MSPA. 54th Annual Meeting of the Biophysical Society, Poster 2182-Plat, 2 pages (2010).
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dorre et al., Techniques for single molecule sequencing. Bioimaging, vol. 5:139-152 (1997).
EBI accession No. GSP:AXX09397. May 13, 2010.
EBI Accession No. A0A085GH19. Oct. 29, 2014.
EBI Accession No. A0A0D1LDB9. Apr. 29, 2015.
EBI accession No. EMBLCDS:ABV05494. Sep. 11, 2007.
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
Engelhardt et al., A tetrameric porin limits the cell wall permeability of *Mycobacterium smegmatis*. J Biol Chem. Oct. 4, 2002;277(40):37567-72. Epub Jul. 18, 2002.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.
Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Goyal et al., Structural and mechanistic insights into the bacterial amyloid secretion channel CsgG. Nature. Dec. 11, 2014;516(7530):250-3. doi: 10.1038/nature13768. Epub Sep. 14, 2014.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Interaction of the noncovalent molecular adapter, beta-cyclodextrin, with the staphylococcal alpha-hemolysin pore. Biophys J. Oct. 2000;79(4):1967-75.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.
Han et al., Characterization and optimization of an entropic trap for DNA separation. Anal. Chem. Jan. 15, 2002;74(2):394-401.

(56) References Cited

OTHER PUBLICATIONS

Han et al., RecJ exonuclease: substrates, products and interaction with SSB. Nucleic Acids Res. Feb. 18, 2006;34(4):1084-91. Print 2006.
Henrickson et al., Driven DNA transport into an asymmetric nanometer-scale pore. Phys Rev Lett. Oct. 2, 2000;85(14):3057-60.
Heron et al., Direct detection of membrane channels from gels using water-in-oil droplet bilayers. J Am Chem Soc. Dec. 26, 2007; 129(51):16042-7. Epub Dec. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.
Ide et al., Lysenin forms a voltage-dependent channel in artificial lipid bilayer membranes. Biochem Biophys Res Commun. Jul. 21, 2006;346(1):288-92. Epub May 26, 2006.
Ivanov et al., DNA tunneling detector embedded in a nanopore. Nano Lett. Jan. 12, 2011;11(1):279-85. doi: 10.1021/n1103873a. Epub Dec. 6, 2010.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Khulbe et al., DNA translocation through a-hemolysin nanopores with potential application to macromolecular data storage. Journal Applied Physics, vol. 97(104317):1-7 (2005).
Kobayashi et al., Comparative Physiology and Biochemistry, 2005, vol. 22, No. 3-4, pp. 139-148.
Langecker et al., Synthetic lipid membrane channels formed by designed DNA nanostructures. Science. Nov. 16, 2012;338(6109):932-6. doi: 10.1126/science.1225624.
Li et al., DNA molecules and configurations in a solid-state nanopore microscope. Nat Mater. Sep. 2003;2(9):611-5. Epub Aug. 24, 2003.
Lieberman et al., Processive replication of single DNA molecules in a nanopore catalyzed by phi29 DNA polymerase. J Am Chem Soc. Dec. 22, 2010; 132(50):17961-72. doi:10.1021/ja1087612. Epub Dec. 1, 2010.
Luo et al., Influence of polymer-pore interactions on translocation. Phys Rev Lett. Oct. 5, 2007;99(14):148102. Epub Oct. 1, 2007.
Maglia et al., DNA strands from denatured duplexes are translocated through engineered protein nanopores at alkaline pH. Nano Lett. Nov. 2009;9(11):3831-6. doi: 10.1021/nl9020232.
Maglia et al., Engineering a Biomimetic Biological Nanopore to Selectively Capture Folded Target Proteins. Biophysical J. Feb. 5, 2013;104(2):518a.
Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.
Manrao et al., Nucleotide Discrimination with DNA Immobilized in the MspA Nanopore PLoS One, vol. 6(10):e25723, 7 pages (2011).
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Manrao et al., Single Nucleotide Discrimination in Single Stranded DNA Immobilized within Biological Nanopre MSPA. 54th Annual Meeting of the Biophysical Society, 3 pages (2010).
Martin et al., Nanoscale protein pores modified with PAMAM dendrimers. J Am Chem Soc. Aug. 8, 2007;129(31):9640-9. Epub Jul. 18, 2007.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005; 102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Moreau et al., Coupling ion channels to receptors for biomolecule sensing. Nat Nanotechnol. Oct. 2008;3(10):620-5. doi: 10.1038/nnano.2008.242. Epub Sep. 7, 2008.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).

(56) References Cited

OTHER PUBLICATIONS

Pavlenok et al., Hetero-oligomeric MspA pores in *Mycobacterium smegmatis*. FEMS Microbiol Lett. Apr. 2016;363(7). pii: fnw046. doi:10.1093/femsle/fnw046. Epub Feb. 23, 2016.
Pavlenok et al., MspA nanopores from subunit dimers. PLoS One. 2012;7(6):e38726. doi: 10.1371/journal.pone.0038726. Epub Jun. 18, 2012.
Pfeiffer et al., Bivalent cholesterol-based coupling of oligonucletides to lipid membrane assemblies. J Am Chem Soc. Aug. 25, 2004;126(33):10224-5.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Rasko et al., The pangenome structure of *Escherichia coli*: comparative genomic analysis of *E. coli* commensal and pathogenic isolates. J Bacteriol. Oct. 2008;190(20):6881-93. doi:10.1128/JB.00619-08. Epub Aug. 1, 2008.
Rhee et al., Nanopore sequencing technology: research trends and applications. Trends Biotechnol. Dec. 2006;24(12):580-6. Epub Oct. 19, 2006.
Robinson et al., Secretion of curli fibre subunits is mediated by the outer membrane-localized CsgG protein. Mol Microbiol. Feb. 2006;59(3):870-81.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon end DNA hairpin substrates. Nucleic Acids Res. Jun. 6, 2006;34(10):3139-49.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Smeets et al., Salt dependence of ion transport and DNA translocation through solid-state nanopores. Nano Lett. Jan. 2006;6(1):89-95.
Soni et al., Synchronous optical and electrical detection of biomolecules traversing through solid-state nanopores. Rev Sci Instrum. Jan. 2010;81(1):014301. doi: 10.1063/1.3277116.
Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012.
Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Taylor et al., Atomic resolution insights into curli fiber biogenesis. Structure. Sep. 7, 2011;19(9):1307-16. doi: 10.1016/j.str.2011.05.015.
Van De Goor, Nanopore Detection: Threading DNA Through a Tiny Hole. PharmaGenomics, vol. 4 (3):28-30 (2004).
Van Gerven et al., Secretion and functional display of fusion proteins through the curlibiogenesis pathway. Mol Microbiol. Mar. 2014;91(5):1022-35. doi:10.1111/mmi.12515 Epub Feb. 12, 2014.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., Nanopores with a spark for single-molecule detection. Nat Biotechnol. Jul. 2001;19(7):622-3.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
U.S. Appl. No. 16/568,225, filed Sep. 11, 2019, Maglia et al.
U.S. Appl. No. 16/540,425, filed Aug. 14, 2019, Heron et al.
U.S. Appl. No. 16/572,869, filed Sep. 17, 2019, Jayasinghe et al.
U.S. Appl. No. 16/522,591, filed Jul. 25, 2019, Howorka et al.
U.S. Appl. No. 16/081,888, filed Aug. 31, 2018, Jayasinghe et al.
PCT/BE2014/000013, Aug. 5, 2014, International Search Report and Written Opinion.
PCT/BE2014/000013, Oct. 8, 2015, International Preliminary Report on Patentability.
Wallace et al., *E. coli* hemolysin E (HlyE, ClyA, SheA): X-ray crystal structure of the toxin and observation of membrane pores by electron microscopy. Cell. Jan. 21, 2000;100(2):265-76.

| Round | Name | Sequence changes |
|---|---|---|
| 0 | ClyA-SS | C87S, C285S |
| 4 | ClyA-CS | L99Q, E103G, F166Y, C285S, K294R |
| 5 | ClyA-AS | C87A, L99Q, E103G, F166Y, I203V, C285S, K294R, H307Y |

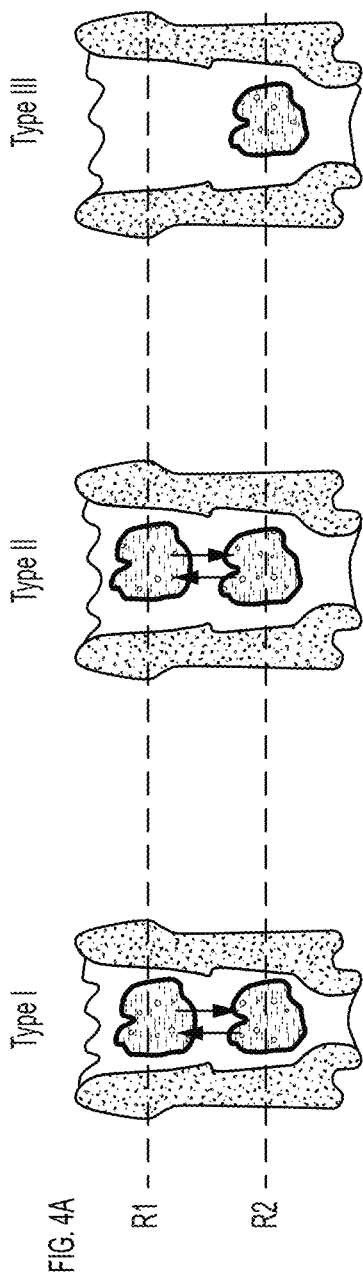
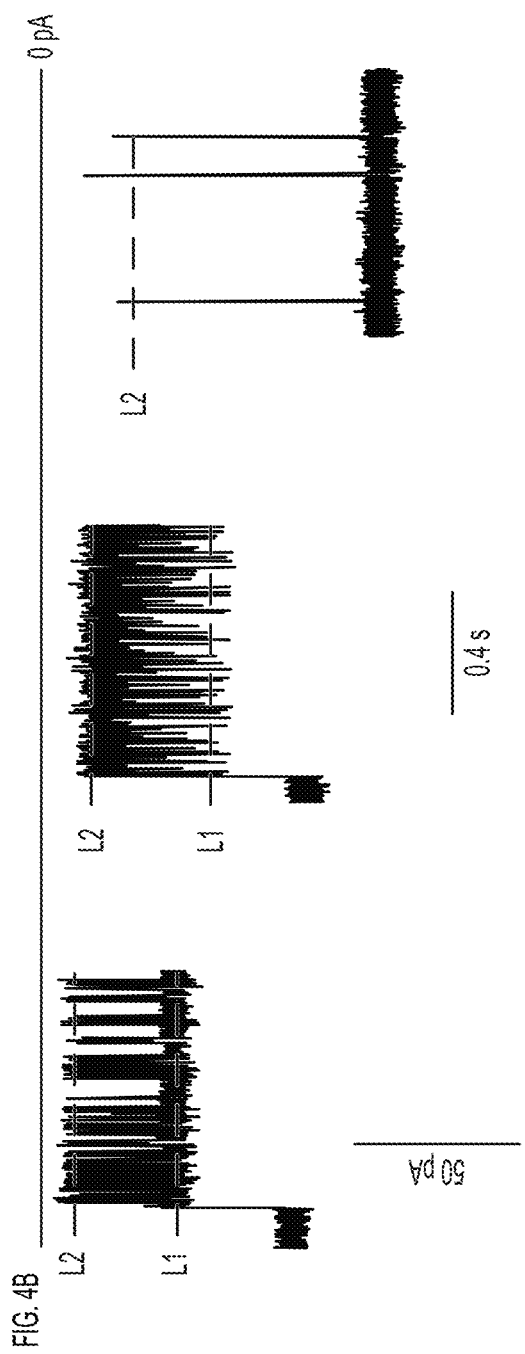
FIG. 4A
FIG. 4B

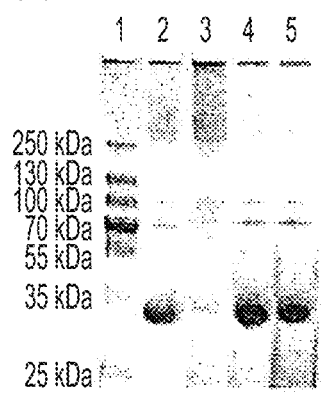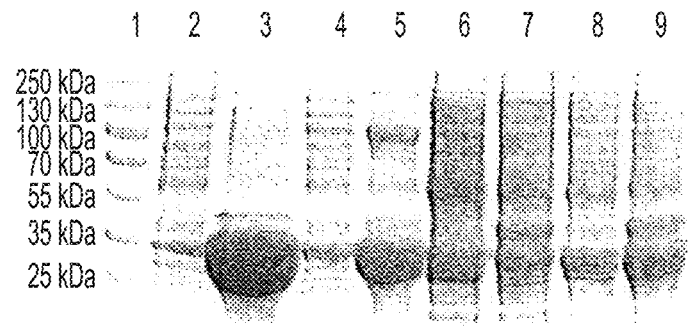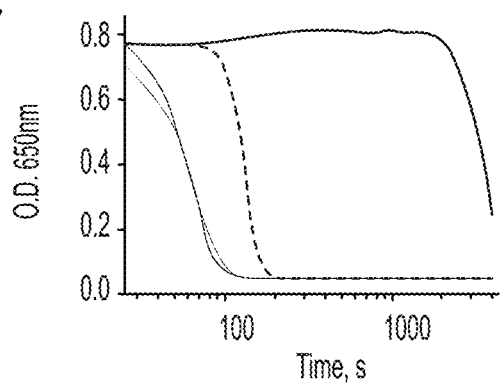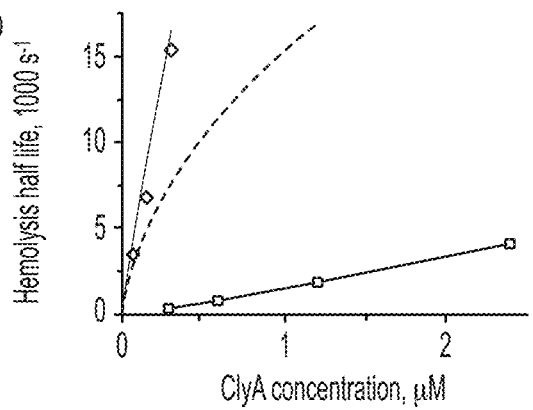

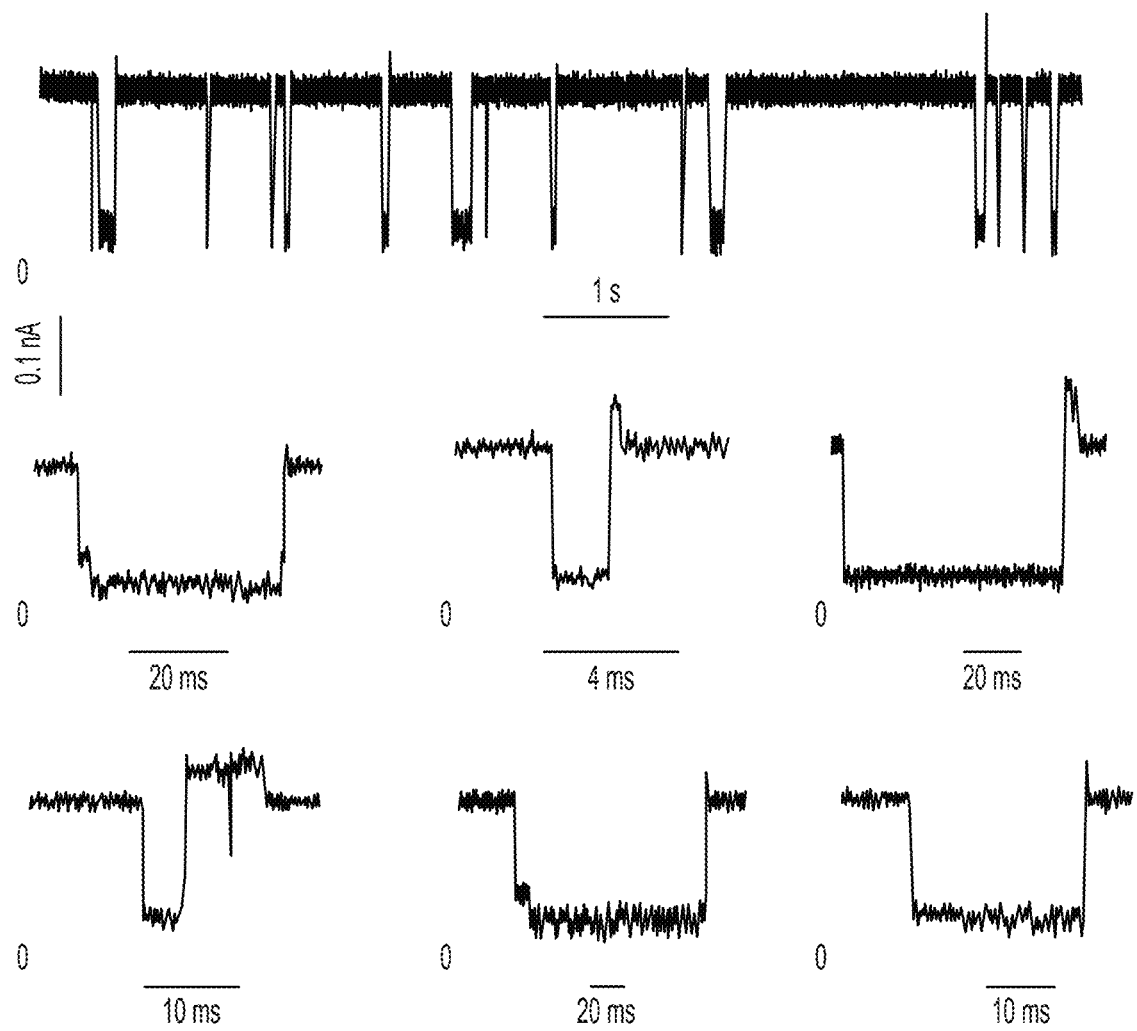

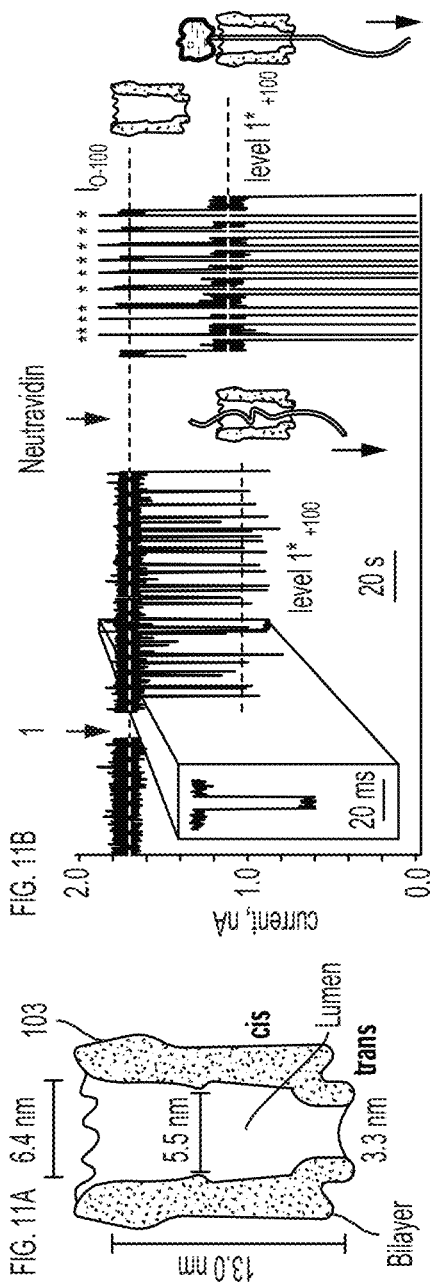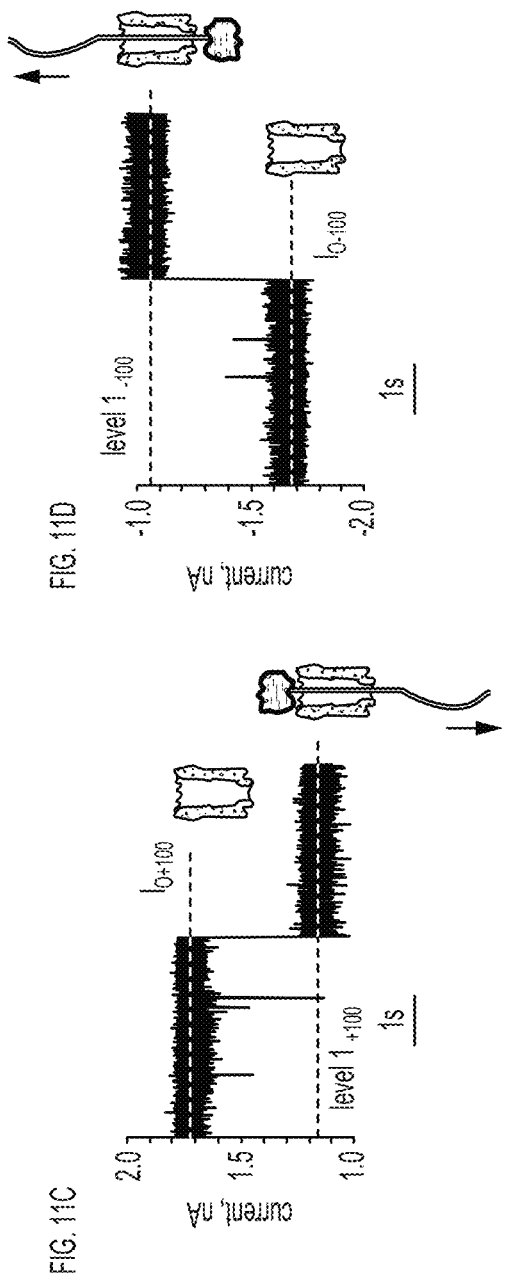

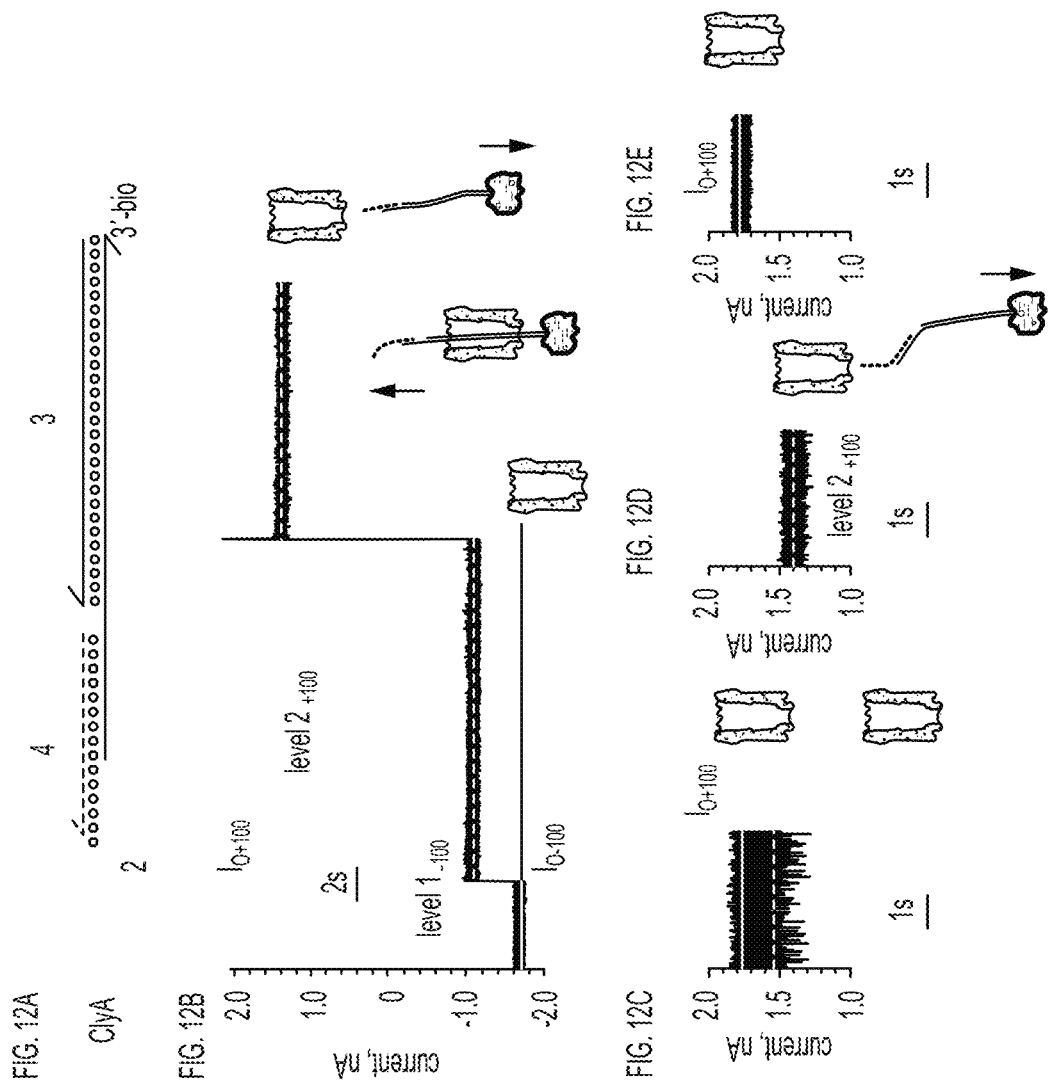

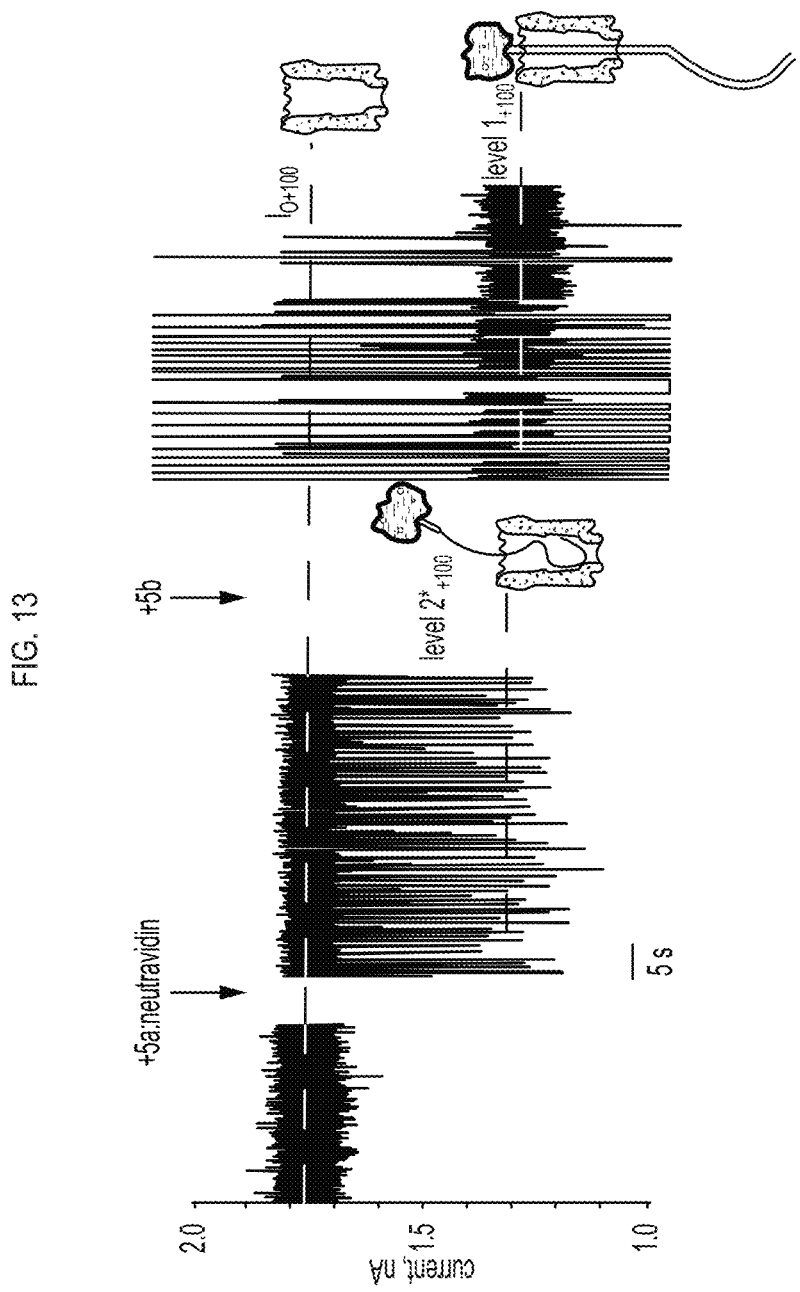

FIG. 14A
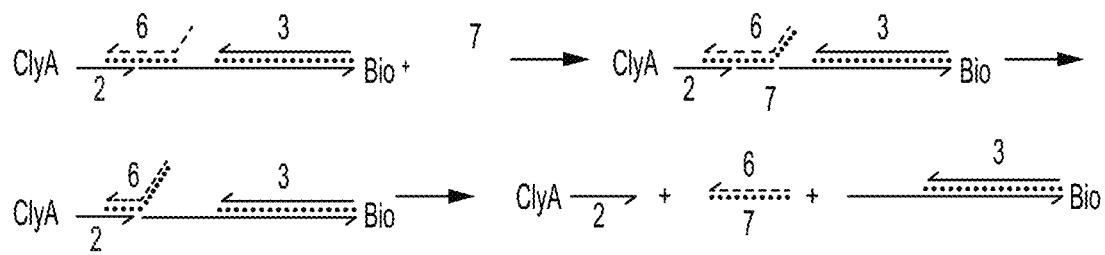
FIG. 14B
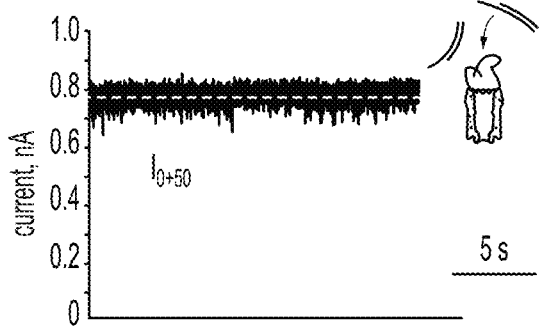
FIG. 14C
FIG. 14D
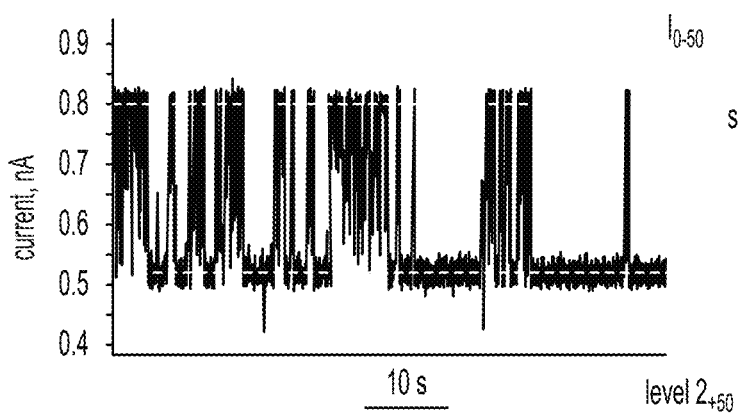
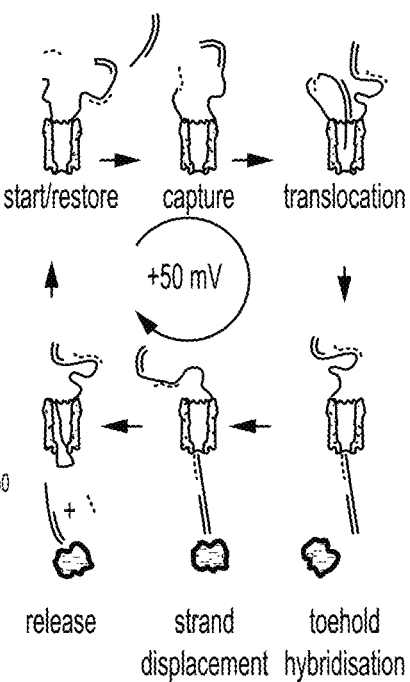

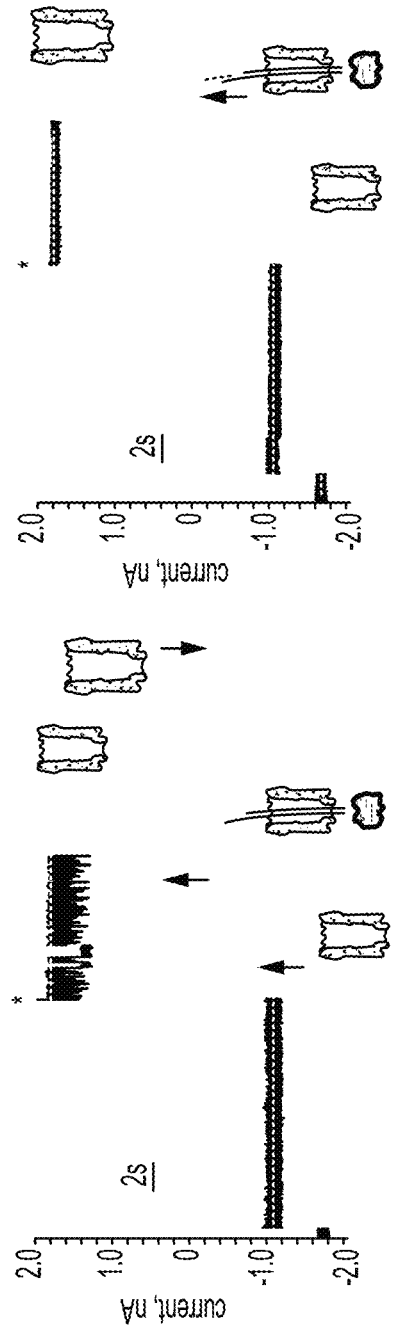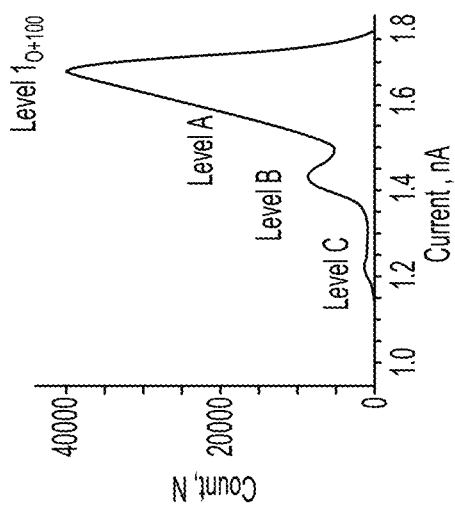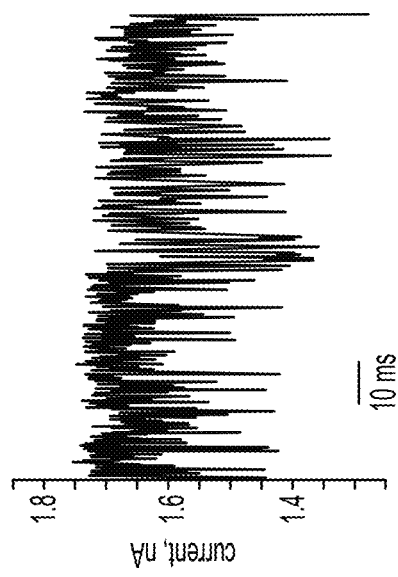
FIG. 15A
FIG. 15B
FIG. 15C
FIG. 15D

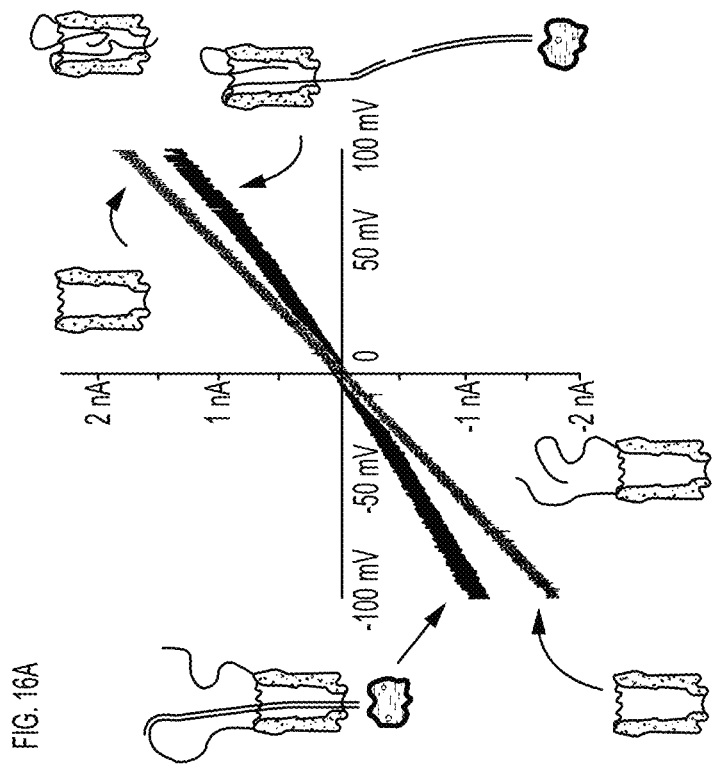
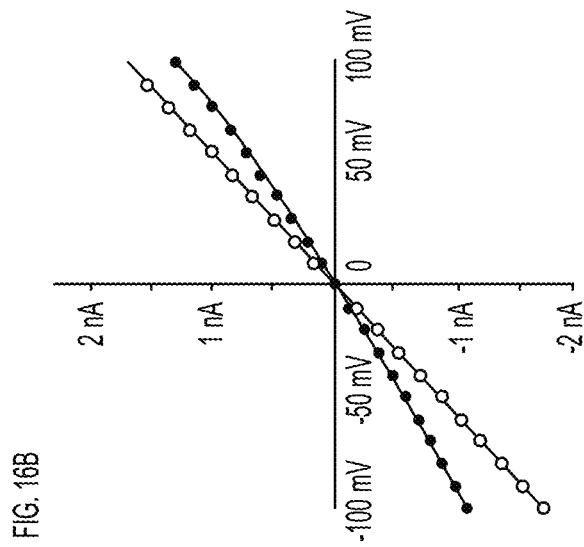
FIG. 16A
FIG. 16B

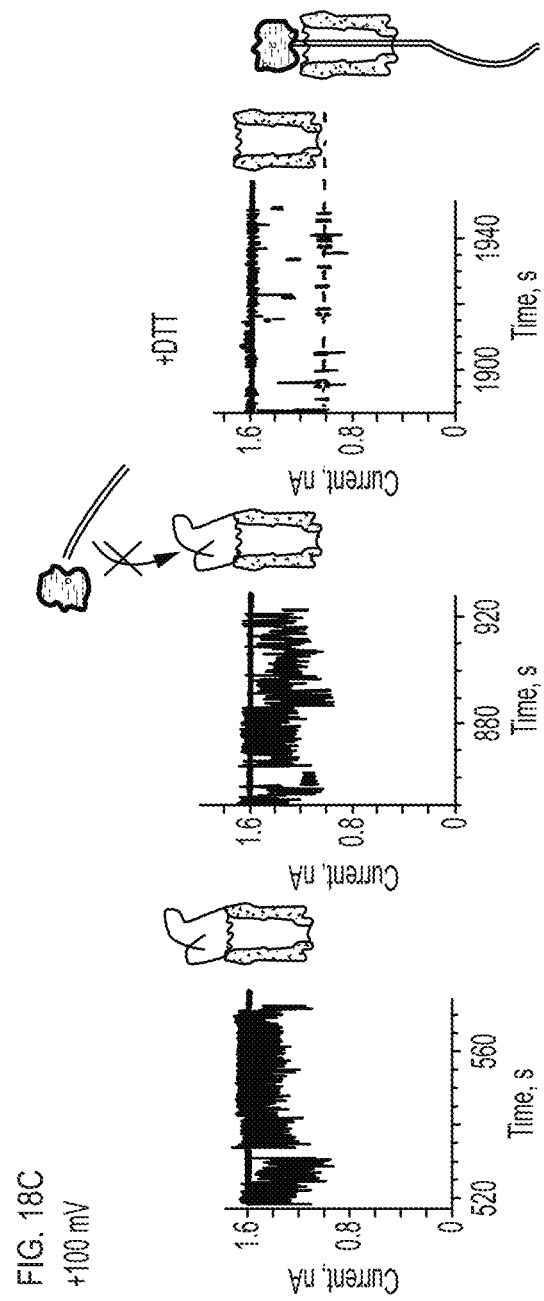

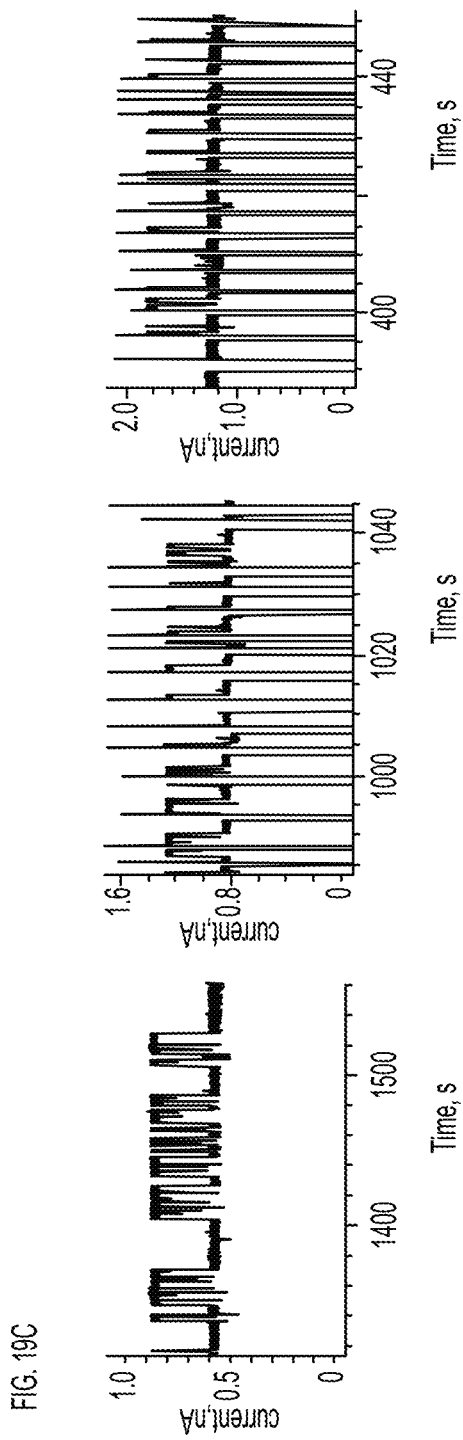

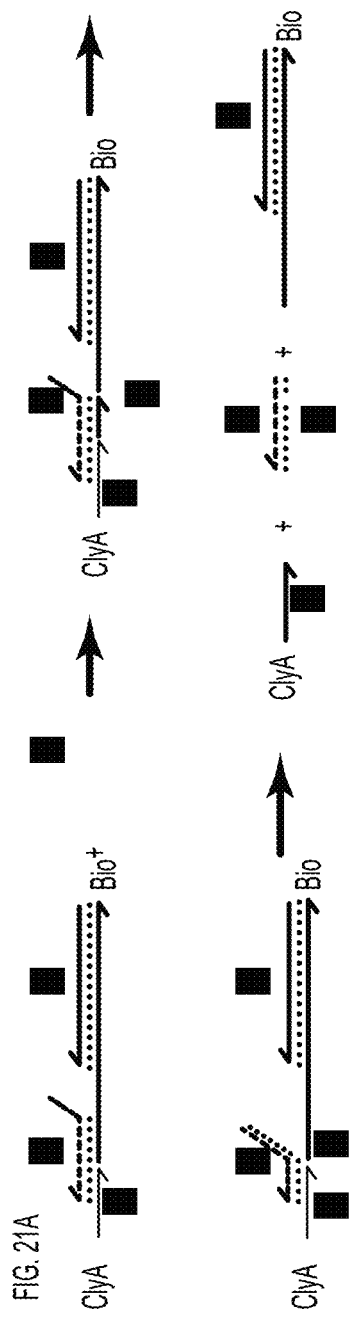
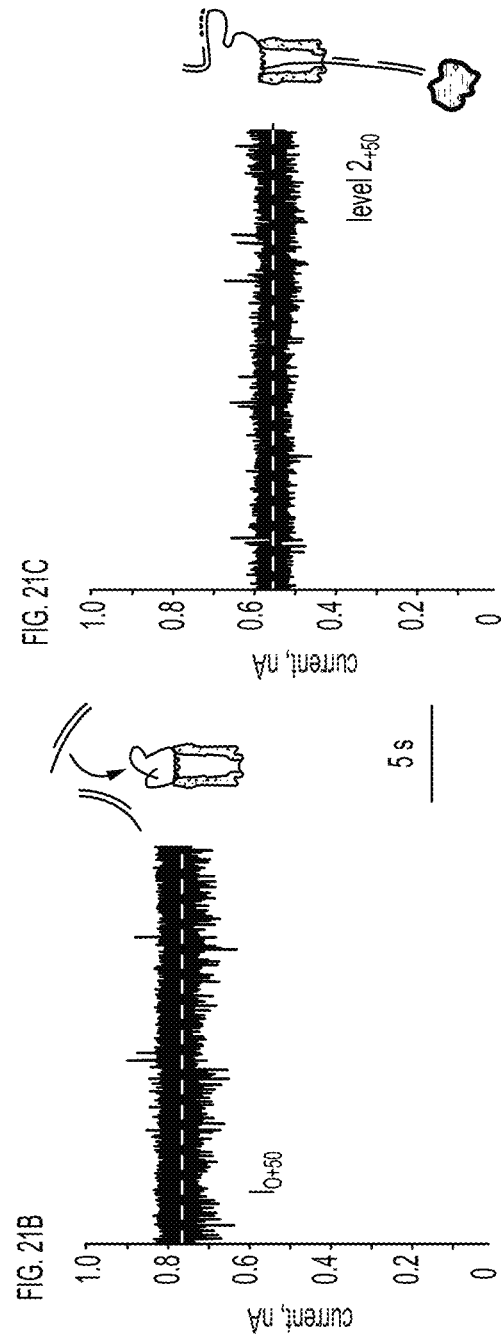
FIG. 21A
FIG. 21B
FIG. 21C

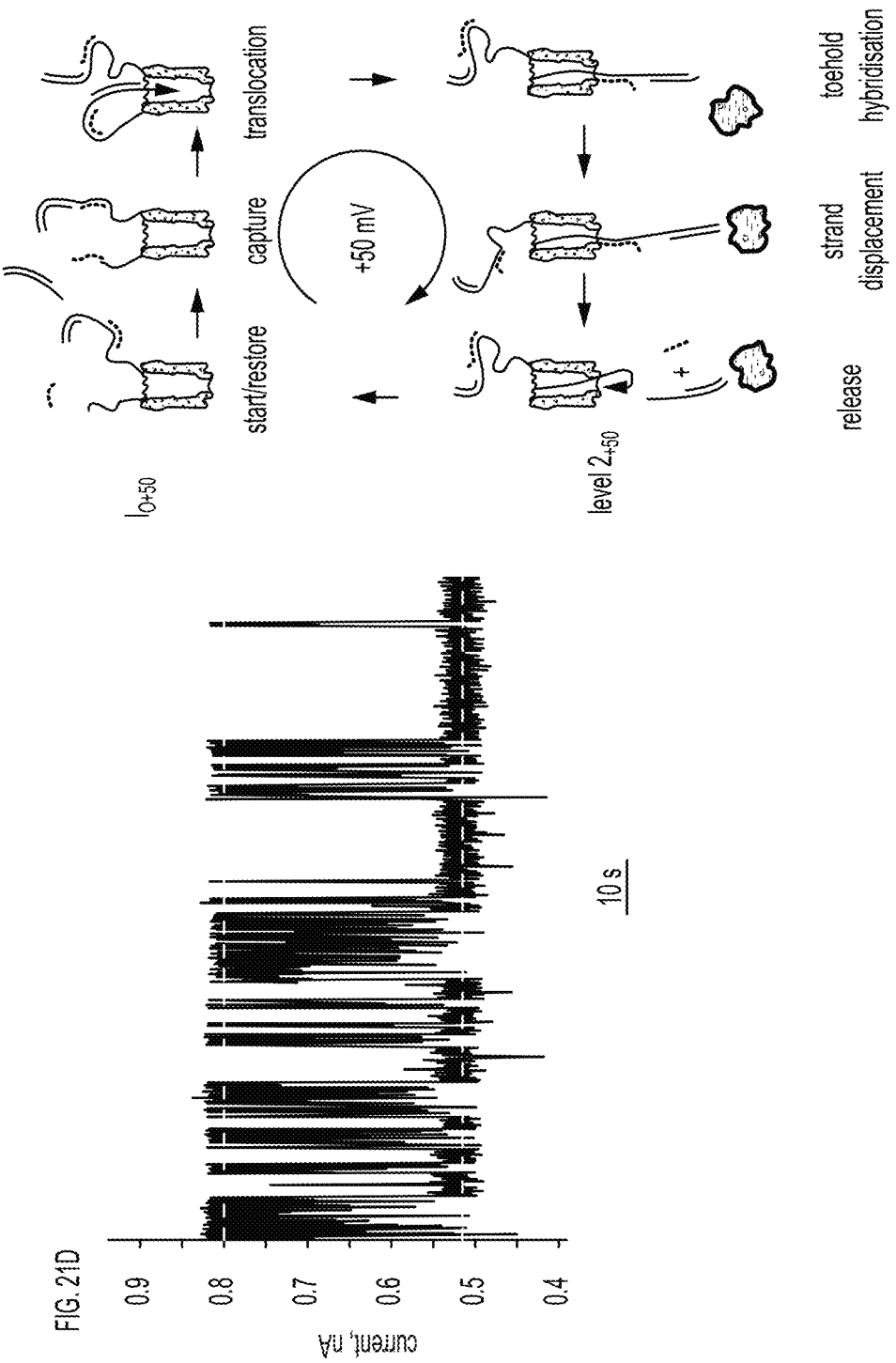

NANOPORE BIOSENSORS FOR DETECTION OF PROTEINS AND NUCLEIC ACIDS

RELATED APPLICATIONS

This application is a continuation of U.S. application Ser. No. 15/984,974 filed May 21, 2018, which is a continuation of U.S. application Ser. No. 14/779,895 filed Sep. 24, 2015, which is a national stage filing under U.S.C. § 371 of PCT International Application No. PCT/BE2014/000013, with an international filing date of Mar. 25, 2014, which claims the benefit under 35 U.SC. § 119(e) to U.S. Provisional Application Ser. No. 61/805,068, filed Mar. 25, 2013 and which claims foreign priority benefits under 35 U.S.C. § 119(a)-(d) or 35 U.S.C. § 356(b) of GB Application Number 1313477.0, filed Jul. 29, 2013, the contents of each of which are incorporated herein by reference in their entireties.

FIELD OF INVENTION

The present disclosure relates to nanopore biosensors based on a modified cytolysin protein. The nanopore biosensors accommodate large molecules including folded proteins and nucleic acids including double stranded (ds) DNA, and showed augmented activity, solubility and electrical properties, as compared with other nanopore biosensors.

BACKGROUND

The transport of ions or molecules across a biological membrane is a fundamental process in cellular life and is tightly regulated by ion channels, transporters and pores. Recently, researchers have adopted biological,[1] solid-state,[2] DNA origami[3] and hybrid[3a,b,4] nanopores in single-molecule analysis.[5] Biological nanopores have advantages compared to their synthetic counterparts, mostly because they can be reproducibly fabricated and modified with an atomic level precision that cannot yet be matched by artificial nanopores. Biological nanopores, however, also have drawbacks. The mechanical stability of biological nanopores depends on individual cases. Alpha hemolysin from *Staphylococcus aureus* (αHL) and porin A from *Mycobocterium smegmatis* (MspA) nanopores remain open in lipid bilayers at high-applied potentials and can cope surprisingly well with extreme conditions of temperature,[6] pH[6b,7] and denaturant concentrations.[6b,8] However, most of other porines and channels are much less robust. Arguably, however, the biggest disadvantage of biological nanopores is their fixed size. For example, the dimensions of αHL, MspA or aerolysin nanopores allowed the analysis of single stranded nucleic acids, aptamers or small peptides,[9] but their small internal diameter (~1 nm) precludes the direct investigations of other important biological systems such as folded enzymes or ribozymes.

Recently a significant number of studies sampled the translocation of folded proteins through artificial nanopores.[10] However, the investigation of proteins with solid-state nanopores is difficult because proteins have a non-uniform charge distribution, they often adsorb to the nanopores surface and they translocate too quickly to be properly sampled.[10c] Further, because proteins have compact folded structure, the diameter of the nanopore should be similar to that of the protein.[10b] Recently, we have introduced Cytolysin A from *Salmonella typhi* (ClyA) as the first biological nanopore that allows the investigation of natively folded proteins.[7a] The ClyA structure is ideal for this task because proteins such as thrombin (37 kDa) or malate dehydrogenase (dimer, 35 kDa monomer) can be electrophoretically trapped between the wide cis entrance (5.5 nm, table 1) and the narrower trans exit (3.3 nm, table 1), and can therefore be sampled for several minutes. Ionic currents through ClyA are so sensitive to the vestibule environment that blockades of human and bovine thrombin can be easily distinguished.[7a] Our work was based on a ClyA construct where the two native cysteine residues of ClyA-WT (C87 and C285) were replaced by serine (ClyA-SS).[7a] However, ClyA-SS monomers showed low water solubility and low activity when compared to ClyA-WT monomers (Figure S1), and in planar lipid bilayers spontaneously opened and closed (gated) at applied potentials higher than +60 mV or lower than −90 mV.

Thus, there remains a need in the art for nanopore biosensors with high sensitivity for target analytes as well as high water solubility and stability at a range of potentials. Nanopore biosensors should have favorable properties of oligomerization, voltage dependent gating, and electrical noise in single-channel current recordings. The present disclosure relates to engineered nanopores in which specific substitutions to the native cysteine residues and other residues confer additional properties as compared with ClyA-WT and ClyA-SS.

SUMMARY

One aspect of the present disclosure relates to a modified ClyA pore comprising a plurality of subunits, wherein each subunit comprises a polypeptide represented by an amino acid sequence at least 80% identical to SEQ ID NO:1 wherein exactly one Cys residue is substituted with Ser. In some embodiments, the Cys residue is C285. In certain embodiments, each subunit of the modified ClyA pore comprises at least one additional amino acid substitution selected from L99Q, E103G, F166Y, and K294R. For example, each subunit may comprise a polypeptide represented by an amino acid sequence of SEQ ID NO:2. In certain embodiments, exactly one Cys residue in each subunit is substituted with Ala. In some embodiments, each subunit of the modified ClyA pore comprises at least one additional amino acid substitution selected from L203V and H207Y. For example, each subunit may comprise a polypeptide represented by an amino acid sequence of SEQ ID NO:3.

In some embodiments, the modified ClyA pore comprises at least 12 subunits. For example, the modified ClyA pore may comprise 12 subunits or may comprise 13 subunits. In certain embodiments, the modified ClyA pore has a cis diameter of at least 3.5 nm. In certain embodiments, the modified ClyA pore has a trans diameter of at least 6 nm. In some embodiments, the modified ClyA pore remains open when the voltage across the modified ClyA pore ranges from −60 +90 to −150 mV.

In some embodiments, a protein analyte binds within the lumen of the modified ClyA pore. A protein analyte may bind to more than one site within the lumen of the modified ClyA pore. In some embodiments, the protein analyte is a protein with a molecular weight in the range of 15-70 kDa.

BRIEF DESCRIPTION OF DRAWINGS

FIG. 1B indicates the sequence changes in ClyA-SS, ClyA-CS and ClyA-AS relative to ClyA-WT.

FIG. 2A shows the oligomerisation of ClyA nanopores examined by 4-20% BN-PAGE. Proteins (1 mg/ml) were pre-incubated with 0.5% DDM for 30 min at room temperature before loading into the gel (40 µg/lane). Lane 1: Protein ladder, lane 2: ClyA-WT, lane 3: ClyA-SS, lane 4: ClyA-AS and lane 5: ClyA-CS. FIG. 2B shows the unitary nanopore conductance distribution obtained from 100 nanopores reconstituted in planar lipid bilayers for ClyA-WT (top), ClyA-CS (middle) and ClyA-AS (bottom) nanopores after pre-oligomerization in 0.5% DDM. Recordings were carried out at −35 mV in 15 mM Tris.HCl, pH 7.5, 150 mM NaCl and the temperature was 28° C.

FIGS. 4A-4B show the current blockades provoked by HT on the three types of ClyA-CS nanopores. In FIG. 4A, from left to right, cut through Type I, Type II and Type III ClyA nanopores (grey) containing HT (black) in the nanopore vestibule. Type II and Type III ClyA nanopores were modeled as 13mer (Type II) or 14mer (Type III) as described in supplementary information. FIG. 4b shows HT blockades to Type I (left), Type II (middle) or Type III (right) ClyA-CS nanopores at −35 mV. HT current blockades to Type I and Type II ClyA-CS switched between L1 (IRES %=56±1 and 68±1, respectively) and L2 (IRES %=23±3 and 31±1, respectively) current levels. The blockades lasted for several minutes, therefore only the first second of the current traces is shown. In Type I ClyA-CS, L1 was the most represented current blockade (70%), while in Type II ClyA-CS L2 was mostly populated (96%). HT current blockades to Type III ClyA-CS nanopores only showed L2 current levels (IRES=32±9). Recordings were carried out at −35 mV in 15 mM Tris.HCl pH 7.5 150 mM NaCl. The traces in FIG. 4B were collected applying a Bessel low-pass filter with 2000 Hz cutoff and sampled at 10 kHz and the temperature was 28° C.

FIG. 5A shows the voltage dependency of HT blockade dwell times determined for Type I (hollow circles) and Type II (filled rectangles) ClyA-CS nanopores. Lifetimes at each voltage were calculated from single exponential fits to cumulative distributions (n≤3) constructed from dwell times of at least 50 blockades. The lines indicate double exponential fits to the experimental points. FIG. 5B shows the HT current blockades to Type I (left) and Type II (right) ClyA-CS nanopores at −150 mV. The blockades showed only L2 current levels for both nanopores (IRES %=23±2 and 31±5, for Type I and Type II ClyA-CS respectively). FIG. 5C shows a typical HT current blockade on Type I ClyA-CS at −150 mV showing "shoulder" and "spike" current signatures. Recordings were carried in 15 mM Tris.HCl, pH 7.5, 150 mM NaCl in presence of 20 nM HT. The traces in FIG. 5B were collected applying a Bessel low-pass filter with 2000 Hz cutoff and sampled at 10 kHz. The trace in c was collected applying a Bessel low-pass filter with 10 kHz cutoff and sampled at 50 kHz. The temperature was 28° C. Errors are given as standard deviations.

FIGS. 6A-6D show the characterization of purified ClyA monomers. FIG. 6A: Solubility of purified ClyA monomers examined by 4-20% acrylamide BN-PAGE. Equal amounts (40 µg) of purified ClyA monomers (no detergent) were supplemented with ~10% glycerol and 1× of NativePAGE™ Running Buffer and 1× Cathode Buffer Additive (Invitrogen™) and loaded in each lane: Lane 1: markers, Lane 2: ClyA-WT, Lane 3: ClyA-SS, Lane 4: ClyA-CS, Lane 5: ClyA-AS. FIG. 6B: Overexpression of ClyA variants. Equal amounts of bacterial pellets derived from overnight cultures overexpressing ClyA variants were resuspended to ~100 mg/mL concentration and disrupted by sonication followed by centrifugation at 20'000 g for 10 min (4° C.). 20 µL of the supernatant containing the soluble fraction of ClyA proteins were loaded on lanes 2, 4, 6 and 8 of a 12% acrylamide SDS-PAGE. The lysate pellets were brought to the original volume by adding a solution containing 15 mM, Tris.HCl pH 7.5, 150 mM NaCl and 2% SDS w/v. 20 µL of such solution were loaded on lanes 3, 5, 7 and 9 of the same 12% acrylamide SDS-PAGE. Therefore, Lane 1: protein marker, Lanes 2 and 3: ClyA-SS supernatant and pellet fractions, respectively; Lanes 4 and 5: ClyA-WT supernatant and pellet fractions, respectively; Lane 6 and 7: ClyA-CS supernatant and pellet fractions, respectively; and Lane 8 and 9: ClyA-AS supernatant and pellet fractions, respectively. FIG. 6C: Hemolytic assays. ClyA monomers (0.6 µM) were Incubated with 100 µL of 1% horse erythrocytes suspension (110 µL final volume) and the decrease of turbidity was measured at 650 nm (OD650 nm). ClyA-WT is shown as a thick grey line, ClyA-SS as a thick black line, ClyA-CS as a thin black line and ClyA-AS as a dashed line. FIG. 6D: The rates of hemolysis (calculated as the inverse of the time to reach 50% of turbidity) plotted against protein concentration ClyA-WT (triangle, thick grey line), ClyA-SS (squares, thick black line), ClyA-AS (circles, dashed line) and ClyA-CS (diamonds, thin black line).

FIG. 7A: Round 4. Lane 1, 2: ClyA-CS, lane 3 and 4: 4ClyA5, lane 5 and 6: 4ClyA3, lane 7 and 8: 4ClyA1, lane 9 and 10: 4ClyA2, lane 11 and 12: 4ClyA6. Samples were prepared as explained in FIG. 6A supplemented with 0.05% (even lane number) or 0.1% (odd lane numbers) SDS. SDS was used to counter the "smearing" effect of large quantity of DDM in the samples. FIG. 7B: Round 5. Lane 1, 2: 5ClyA2, lane 3: 5ClyA1, lane 4: ClyA-AS. Samples were supplemented with 0.05% SDS. Oligomerization was triggered by the addition of 1% DDM and ClyA variants were partly purified by Ni-NTA affinity chromatography as described in methods.

FIG. 10 shows the typical HT current blockades on Type I ClyA at −150 mV showing "shoulder" and "spike" current signatures. Recordings were carried in 15 mM Tris.HCl, pH 7.5, 150 mM NaCl in presence of 20 nM HT. The traces were filtered with a Gaussian low-pass filter with 10,000 Hz cutoff filter and sampled at 50,000 Hz.

FIGS. 11A-11D show dsDNA translocation through ClyA nanopores. On the right of the current traces, ClyA (pore shaped structure) and neutravidin (dark gray) are depicted, and the dsDNA is shown as a black line. FIG. 11A: Sections through of ClyA from *S. typhi* constructed by homology modeling from the *E. coli* ClyA structure (PDB: 2WCD, 90% sequence identity).[22] ClyA is shown with pore measurements including the Van der Waals radii of the atoms, and the approximate location of residue 103 (serine in the WT sequence) on the pore indicated. FIG. 11B: at +100 mV (level $I_{O+100}$=1.74±0.05 nA), the addition of 0.12 μM of 290 bp dsDNA 1 to the cis side of a ClyA nanopore provokes short current blockades of $I_{RES}$=0.63±0.01 (level $1^*_{+100}$=1.10±0.03 nA, n=3) that are due to the translocation of dsDNA through the pore. Addition of neutravidin to the cis chamber converted the short current blockades to higher conductive and long-lasting current blockades with $I_{RES}$=0.68±0.01 (level $1_{+100}$=1.19±0.01) due to the partial translocation of DNA through the pore. The open pore current was restored by reversing the potential to −100 mV (red asterisk). The inset shows a typical transient current blockade. FIG. 11C: Details for a current blockade due to the formation of a cis pseudorotaxanes at +100 mV. FIG. 11D: Formation of a trans pseudorotaxanes at −100 mV by threading the dsDNA:neutravidin complex (see above) from the trans side (level $1_{−100}$=1.02±0.03 nA, $I_{RES}$=0.62±0.01, n=4). The electrical recordings were carried out in 2.5 M NaCl, 15 mM Tris.HCl pH 7.5 at 22° C. Data were recorded by applying a 10 kHz low-pass Bessel filter and using a 20 μs (50 kHz) sampling rate.

FIGS. 12A-12E show formation of a nanopore-DNA rotaxane. FIG. 12A: representation of the hybridisation of the DNA molecules used to form the rotaxane. Arrowheads mark the 3' ends of strands. FIG. 12B: rotaxane formation. At −100 mV following the addition of the DNA hybrid 3 (1 μM) complexed with neutravidin (0.3 μM) and oligo 4 (1 μM) to the trans compartment, the open pore current of ClyA-2 ($I_{O−100}$=−1.71±0.07 nA, n=4) is reduced to level $1_{−100}$=1.1±0.04 nA ($I_{RES}$ value of 0.64±0.02, n=4), indicating that dsDNA threads the pore from the trans side. Stepping to +100 mV (red asterisk) produced a current block with $I_{RES}$=0.77±0.04 (level $2_{+100}$=1.31±0.09 nA, n=4), indicating that the DNA is still occupying the pore at positive applied potentials. Level 2 most likely corresponds to ssDNA occupying the vestibule of the pore. Successive switching to positive applied potentials did not restore the open pore current (FIG. 16), confirming that a rotaxane is permanently formed. FIGS. 12C-12E: Rotaxane removal. FIG. 12C: at +100 mV the ionic current through ClyA-2 nanopores showed a multitude of fast current blockades (FIG. 15), suggesting that the ssDNA molecules attached at the cis entrance of the pore transiently occupy the lumen of the pore. FIG. 12d: after the rotaxane is formed (FIG. 12B), at +100 mV the nanopore shows a steady ionic current (level $2_{+100}$) suggesting that a single DNA molecule is occupying the pore. FIG. 12E: 20 minutes after the addition of 20 mM DTT to the cis compartment the DNA molecules atop the ClyA pore are removed and the open pore current at +100 mV is restored ($I_{O+100}$=1.78±0.07, n=4). Recordings were performed as described in FIG. 11.

FIG. 13 shows the ssDNA blockades to ClyA-CS. At +100 mV, the addition of 2 μM of a biotinylated ssDNA (5a) to the cis side of ClyA-CS nanopores in the presence of 0.6 μM neutravidin provoked transient current blocks (1.24±0.02 nA, $I_{RES}$=0.69±0.04, n=3), indicating that ssDNA can enter the lumen of the pore but only transiently. The subsequent addition of the complementary ssDNA strand (5b) converted the current blockades into level $1_{+100}$ blocks (1.22±0.13 nA, $I_{RES}$=0.67±0.01, n=3), Indicating that the dsDNA can now translocate the entire length of the pore.

FIGS. 14A-14D show the transport of DNA through ClyA nanopores. FIG. 14A: schematic representation of the strand displacement reaction that promotes the release of DNA from the pore. FIG. 14B: at +50 mV and in the presence of 3 (0.3 μM) ClyA-2 showed a steady open pore current ($I_{O+50}$=0.85±0.01 nA, n=3), showing that the ssDNA strands attached to the pore do not thread through the lumen of the pore and prevent the translocation of dsDNA form solution. FIG. 14C: the addition of the ssDNA strands 6 (40 nM) to the cis chamber produced long lasting current blockades with $I_{RES}$=0.70±0.02, (level $2_{+50}$=0.59±0.02 nA, n=5) indicating that the dsDNA hybrid is threaded the pore. FIG. 14D: the subsequent addition of 1 μM of 7 to the trans chamber (+50 mV), which also contains 0.3 μM neutravidin, promoted the release of the DNA thread and restored the open pore current. Subsequently, dsDNA molecules are sequentially captured and released as shown by multiple blocked and open pore currents. For the sake of clarity, neutravidin is not included in the cartoon representation. The electrical recordings were carried out in 2.5 M NaCl, 15 mM Tris.HCl pH 7.5 at 22° C. Data were recorded by applying a 10 kHz low-pass Bessel filter and using a 20 μs (50 kHz) sampling rate. The current signal in panel d was digitally filtered at 2 kHz with a post-acquisition low-pass Gaussian filter. The applied potential of this experiment was set to +50 mV to facilitate the observation of the multiple block and release (FIG. 14D), as at higher applied potentials the capture of the DNA in cis is very fast.

FIGS. 15A-15D show the results of control experiments showing that all components of FIG. 12 are necessary to form a DNA rotaxane. FIG. 15A: the absence of the bridging sequence 4 does not allow the linkage between ClyA-2 and 3. After the complex is captured at −100 mV it is readily expelled from the pore at +100 mV (asterisk) as shown by the typical current signature of an open pore current for ClyA-2 at +100 mV. FIG. 15B: the absence of 2 from the pore top (e.g. after cleavage with DTT) does not allow 3·4 DNA hybrid to bind to the pore when captured at −100 mV. Upon reversing the potential to +100 mV (red asterisk) the open pore current is restored. FIG. 15C: Typical current recording for a ClyA-2 nanopore at +100 mV. FIG. 15D: all points histogram (5 pA bin size) for 20 seconds of the current trace shown in FIG. 15A. Level $I_{O+100}$=1.71±0.07 nA, level A=1.62±0.12 nA, level B=1.43±0.05 nA and level C=1.28±0.06 nA, corresponding to the $I_{RES}$ values of 0.94±0.04, 0.84±0.03 and 0.75±0.03, respectively. The values, calculated from 12 experiments, might represent the DNA strands lodging within the lumen of ClyA.

FIGS. 16A-16B show the Current versus voltage (IV) relationships for ClyA-2 nanopores. FIG. 16A: a typical curve for ClyA-2 before (lightest grey line) and after (black line) rotaxane formation. The medium-grey line indicates the same nanopore after the DNA molecules attached to the nanopore are removed by the addition of DTT. The current recordings were measured by applying an automated protocol that ramped the voltage from −100 mV to +100 mV In 4 seconds. FIG. 16B: I-V curves calculated from the average of four experiments showing the steady-state (1 s) ClyA-2 open pore current levels (white spheres) and ClyA-2 open pore current levels in a rotaxane configuration (black spheres). The unitary conductance values of the nanopores as calculated from the slopes of the I-V curves were 17.1 nS for ClyA-2 at both positive and negative bias, 10.8 nS for the rotaxane at negative bias and 13.0 nS at positive bias. The rotaxanes were prepared as described in FIG. 12.

FIGS. 17A-17D: current recordings for ClyA-2 after hybridisation with a 6·7 (indicated with asterik) at different applied potentials. FIG. 17E: at +50 mV, upon hybridisation with 6 (40 nM) and 2, the DNA duplex 3 (0.3 μM) is transported through the pore as shown by the drop in the ionic current from $I_{O+50}$=0.85±0.01 nA, to a level $2_{+50}$ block ($I_{RES}$=0.70±0.02). Reversal of the applied potential to −50 mV restores the open pore current ($I_{O-50}$=0.83±0.00). FIG. 17F: the subsequent addition of 1 μM neutravidin (black) to the trans chamber locked the DNA thread within the pore as revealed after the reversal of the potential to −50 mV when a blocked pore level ($I_{RES}$=0.67±0.02) was observed.

FIGS. 18A-18C show selective DNA translocation through ClyA-2 pores. FIG. 18A: left, at +50 mV the ionic current through ClyA-2 nanopores showed fast and shallow current blockades, suggesting that the ssDNA molecules attached at the cis entrance might transiently occupy the lumen of the pore. Middle, after dsDNA strand 1 (50 nM) Is added to the cis chamber the current signals did not change, indicating that dsDNA does not translocate ClyA-2. Right, 20 minutes after the addition of 20 mM DTT to the cis compartment the DNA molecules atop the ClyA pore are removed and the DNA can translocate through the pore. FIG. 18B: same experiment as described in panel a but in the presence of 1 μM of neutravidin. FIG. 18C: same as in FIG. 18B, but at +100 mV.

FIGS. 19A-19C show Voltage dependence of the interaction of a ssDNA-dsDNA hybrid 5 construct with ClyA-CS pores. FIG. 19A: depiction of the DNA molecules used in the experiments described in FIG. 19B and FIG. 19C. FIG. 19B: current blockades of the DNA hybrid 3 (FIG. 19A, left) in complex with neutravidin at +50 mV (left), +70 mV (middle) and +100 mV (right). FIG. 19C: current blockades of the DNA hybrid 3:6 (FIG. 19A, right) in complex with neutravidin at +50 mV (left), +70 mV (middle) and +100 mV (right).

FIG. 14 shows the implementation of the first reaction of the OR gate.

FIGS. 21A-21D show alternative transport of DNA through ClyA nanopores. FIG. 21A: schematic of the release of the DNA thread by strand displacement showing the implementation of the second reaction of the OR gate described in FIG. 18. FIG. 21B: open pore current of ClyA-2 at +35 mV. FIG. 21C: addition of DNA strands 3 (1 μM) and 8 (0.5 μM) to the cis chamber produce long lasting current blockades, Indicating that the dsDNA hybrid is threading the pore. FIG. 21D: at +35 mV the subsequent addition of 1 μM of 9 to the trans chamber, which also might contain 1 μM neutravidin, promoted the release of the DNA thread and restored the open pore current. Subsequently, other dsDNA molecules are captured and then released as shown by the cycles of blocked and open pore currents. Data were recorded by applying a 10 kHz low-pass Bessel filter and using a 20 μs (50 kHz) sampling rate.

DETAILED DESCRIPTION

Figures 1A, 1B:
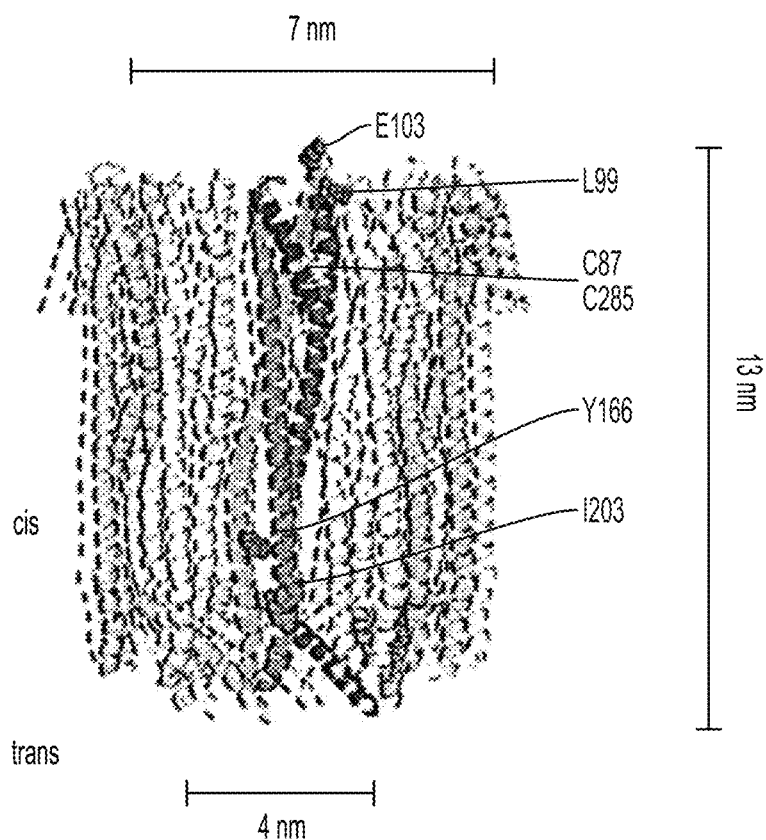
FIGS. 1A-1B show a ribbon representation of *S. typhi* ClyA nanopores constructed by homology modeling from the *E. coli* ClyA structure (PDB: 2WCD, 90% sequence identity).[17] In FIG. 1A, one protomer is highlighted, with the secondary structure elements shaded in dark grey from N to C terminii; other protomers are shown alternating in pale grey. The side chain of the amino acids changed by directed evolution experiments are displayed as spheres. The two native cysteine residues and Phenylalanine 166 are labeled.

The present disclosure relates to nanopore biosensors which may be used for a variety of applications, including but not limited to detection and quantification of proteins and translocation of DNA. The nanopores are based on pore-forming bacterial cytotoxins, which act as channels for large macromolecules such as proteins and nucleic acids. Nucleic acids may include DNA, for example, single stranded DNA (ssDNA) or double stranded DNA (dsDNA), RNA, peptide nucleic acids, and/or nucleic acid analogs.

Modified Nanopore Biosensors

One aspect of the present disclosure relates to nanopore biosensors made from modified pore proteins. Exemplary pore proteins include, but are not limited to cytolysins, hemolysins, porins, DNA packaging protein, and motor proteins. Pore proteins may be bacterial or viral proteins.

In certain embodiments, the modified pore protein is a pore-forming cytotoxic protein, for example, a bacterial cytolysin. The cytolysin may be a Cytolysin A (ClyA) from a gram-negative bacteria such as *Salmonella* or *Escherichia coli* (*E. coli*). In some embodiments, the modified cytolysin is a modified ClyA from *Salmonella typhi* (*S. typhi*) or *Salmonella paratyphi* (*S. paratyphi*). In some embodiments, the modified ClyA pore comprises a plurality of subunits, wherein each subunit comprises a polypeptide represented by an amino acid sequence at least 80% identical to SEQ ID NO: 1. In certain embodiments, the subunits are represented by an amino acid sequence at least 85% Identical, 90% identical, 95% identical, or 100% identical to SEQ ID NO:1. Identical may refer to amino acid identity, or may refer to structural and/or functional identity. Accordingly, one or more amino acids may be substituted, deleted, and/or added, as compared with SEQ ID NO:1. Modifications may alter the pore lumen in order to alter the size, binding properties, and/or structure of the pore. Modifications may also alter the ClyA pore outside of the lumen.

In certain embodiments, each subunit comprises a polypeptide represented by an amino acid sequence at least 80% identical to SEQ ID NO:1, wherein exactly one Cys residue is substituted with Ser. Each subunit may be represented by an amino acid sequence that is at least 85%, 90%, 95%, 96%, 96%, 98%, or 99% identical to SEQ ID NO:1, and additionally exactly one Cys residue may be substituted with Ser. The Cys residue may be Cys 87 and/or Cys 285 in SEQ ID NO:1. In some embodiments, the Cys residue is Cys285. Other amino acid residues may be substituted, for example, with amino acids that share similar properties such as structure, charge, hydrophobicity, or hydrophilicity. In certain embodiments, substituted residues are one or more of I99, E103, F166, and K294. For example, the substituted residues may be one or more of L99Q, E103G, F166Y, and K294R. An exemplary subunit may comprise substitutions L99Q, E103G, F166Y, K294R, and C285S. Thus, each subunit may comprise a polypeptide represented by an amino acid sequence of SEQ ID NO:2. An exemplary modified ClyA pore comprising subunits in which exactly one Cys residue is substituted with Ser may be called ClyA-CS.

The modified ClyA pore may comprise a plurality of subunits, wherein each subunit comprises a polypeptide represented by an amino acid sequence that is at least 80% identical to SEQ ID NO:1, wherein exactly one Cys residue is substituted with Ala. The cysteine residue may be Cys 87 or Cys 285. Each subunit may be represented by an amino acid sequence that is at least 85%, 90%, 95%, 96%, 96%, 98%, or 99% identical to SEQ ID NO:1, and exactly one Cys residue may be substituted with Ser and/or exactly one Cys residue may be substituted with Ala. In some embodiments, each subunit is represented by an amino acid sequence that is at least 85%, 90%, 95%, 96%, 96%, 98%, or 99% identical to SEQ ID NO:1, and additionally exactly one Cys residue may be substituted with Ser and exactly one Cys residue may be substituted with Ala. Other amino add residues may be substituted, for example, with amino acids that share similar properties such as structure, charge, hydrophobicity, or hydrophilicity. In certain embodiments, substituted residues are one or more of L99, E103, F166, K294, L203 and H207. For example, the substituted residues may be L99Q, E103G, F166Y, K294R, L203V, and H207Y. An exemplary subunit may comprise L99OQ E103G, F166Y, K294R, L203V, and H207Y, and C285S. Accordingly, each subunit may comprise a polypeptide represented by an amino acid sequence of SEQ ID NO:3. An exemplary modified ClyA pore comprising subunits in which exactly one Cys residue is substituted with Ser and exactly one Cys residue is substituted with Ala may be called ClyA-AS.

The present disclosure further relates to nucleic acids encoding the modified ClyA pores. In some embodiments, a nucleic acid encoding a modified ClyA pore is represented by a nucleotide sequence that is at least 80%, 90%, 95%, 96%, 96%, 98%, or 99% identical to SEQ ID NO:4. A nucleic acid may be represented by SEQ ID NO: 5 or SEQ ID NO:6. Nucleotide sequences may be codon optimized for expression in suitable hosts, for example, E. coli.

The modified ClyA pore may have a pore lumen of at least 3 nm in diameter, for example, the diameter may measure 3 nm, 3.5 nm, 4 nm, 4.5 nm, 5 nm, 5.5 nm, 6 nm, 6.5 nm, 7 nm, or greater. The size of the pore lumen may depend on the analyte to be detected by the modified ClyA pore. The cis diameter of the pore lumen may be at least 3.5 nm and/or the trans diameter of the ClyA pore may be at least 6 nm. In general, cis refers to the end of the modified ClyA pore to which an analyte is added, while trans refers to the end of the modified ClyA pore through which the analyte exits after translocating the length of the pore lumen. In artificial lipid bilayers, for example, the trans end of a pore may be inserted in the lipid bilayer, while the cis end of the pore remains on the same side of the lipid bilayer. Accordingly, the cis diameter of the pore is the diameter of the opening at the cis end of the pore, and the opening to which an analyte is added, while the trans diameter of the pore is the diameter at the opening of the trans end of the pore, from which an analyte exits.

The size of the pore lumen may also depend on the number of subunits in the modified ClyA pore. For example, larger pores which are made up of 13 or 14 subunits may have larger lumens than pores made up of 7 subunits. In some embodiments, the modified ClyA pores comprise 12 or more subunits. In certain embodiments, the modified ClyA pores comprise 12 subunits. In certain embodiments, the modified ClyA pores comprise 13 subunits, or comprise 14 subunits. The subunits may preferentially assemble in 12mers and/or 13mers, depending on the amino acid sequence of the subunits. In some embodiments, each subunit comprises a polypeptide as disclosed herein. Within a single modified ClyA pore, each of the subunits may be identical, or the subunits may be different, so that subunits in a modified ClyA pore may comprise sequences that differ from sequences of other polypeptide subunits in the same modified ClyA pore. In certain embodiments, modified ClyA pores as disclosed herein, such as ClyA-CS pores, may form more than one subtype depending on subunit composition. For example, there may be at least 2 or 3 different subtypes (i.e., Type I, Type II, Type III) of modified ClyA-CS pore, depending on subunits. Each subtype may have different conductance measurements, as compared with other subtypes. Subtypes may be preferentially formed by subunits of a particular polypeptide sequence.

The substitutions in specific residues may confer new properties on the modified ClyA pores, as compared with wild-type ClyA pores found in nature. Voltage dependent opening and closing (gating) of the pore at specific voltages is one property. In planar lipid bilayers, for example, ClyA-SS spontaneously opens and closes at applied potentials that are greater than +60 mV or lower than −90 mV. In some embodiments, the modified ClyA pores as described herein remain open when the voltage across the pore (i.e., the voltage across the membrane which the modified ClyA pore is in) ranges from +90 mV to −150 mV. Accordingly, the modified ClyA pore may remain open when the voltage across the pore is held at +90, +85, +80, +75, +70, +65, +60, +55, +50, +45, +40, +35, +30, +25, +20, +15, +10, +5, 0, −5, −10, −15, −20, −25, −30, −35, −40, −45, −50, −60, −65, −70, −75, −80, −85, −90, −95, −100, −110, −115, −120, −125, −130, −135, −140, −145, −150 mV, and/or the voltage across the pore is adjusted between +90 mV and −150 mV (inclusive), or any subrange of voltages in between. In certain embodiments, the modified ClyA pores show low electrical noise as compared with the signal (i.e., the current block measured). Thus, the noise inherent in a modified ClyA pore is reduced when pores as described herein are used. An exemplary modified ClyA pore shows noise measurements of _1.5 pA rms_ to 3 pA rms_under_−35 mV in 150 mM NaCl 15 mM Tris·HCl pH 7.5_conditions. Notably, it is possible to reduce noise by increasing the salt concentration and/or altering the length of time during which a current block is measured.

In some embodiments, the modified ClyA pores show solubility properties that differ from wild-type ClyA pores. For examples, monomers of the modified ClyA pores may be soluble in water, and/or in other solutions where surfactants such as SDS or DDM are not present. Stable oligomers are modified ClyA pores that are capable of withstanding applied potentials of +150 mV to −150 mV across membranes or lipid bilayers Into which the modified ClyA pores are inserted.

Nanopores with Ligands

A further aspect of the present disclosure relates to nanopore biosensors in which modified ClyA pore proteins are combined with ligands that have selective binding properties. In some embodiments, these modified pores and ligands are used to identify protein analytes in complex biological samples, for example, in a tissue and/or a bodily fluid. The target protein analyte may be present in a low concentration as compared to other components of the sample. In some embodiments, ligands may also be used to target subpopulations of macromolecular analytes based on conformation or on functional properties of the analytes. The presence of a ligand may increase the association of the target protein analyte with the modified pore. For example, the ligands may act as a selectivity filter at the entrance of the pore, increasing capture of the target protein while repulsing other non-target proteins in the sample.

Exemplary ligands include but are not limited to aptamers, antibodies, receptors, and/or peptides that bind to the target protein. In some embodiments, ligands may be inhibitors of the target protein, which suppress the binding of the target protein to the modified ClyA pore.

In certain embodiments, a ligand that binds to a target protein analyte is added to a sample prior to the detection steps described above. This step may provide additional confirmation that a target protein analyte is present. Thus, a method for detecting at least one target protein in a sample may comprise comprises (a) contacting the sample with a ligand that binds to a target protein; (b) contacting the sample with a modified ClyA pore as disclosed herein; (b) applying an electrical potential across the modified ClyA pore; (c) measuring electrical current passing through the modified ClyA pore at one or more time intervals; and (d) comparing the electrical current measured at one or more time intervals with a reference electrical current, wherein a change in electrical current relative to the reference current indicates that the presence of the target protein in the sample. In addition, the change in electrical current may be compared with a sample that was not contacted with a ligand prior to measuring the electrical current through the modified ClyA pore. If a target protein analyte is indeed present, the addition of a ligand will suppress the binding of the target protein to the modified ClyA pore, and a current block would not be detected. In contrast, a current block would be detected when the ligand was not added. With both results together, the presence and the concentration of the target protein could be determined. For example, in a given sample containing many different proteins including a target protein analyte, the sample may initially give X blockades per second. After addition of an excess of a specific ligand, the sample may give (X-n) blockades per second. Thus, n may reflect the blockades per second produced by the target protein analyte in the original sample, which, in turn, may provide information about the concentration of the target protein analyte in the original sample.

In certain embodiments, varying electrical potentials are applied across the modified ClyA pore. For example, the electrical potential applied across the modified ClyA pore may range from −90 mV to +90 mV. The electrical potential may be −90 mV, −85 mV, −80 mV, −75 mV, −70 mV, −65 mV, −60 mV, −55 mV, −50 mV, −45 mV, −40 mV, −35 mV, −30 mV, −25 mV, −20 mV, −15 mV, −10 mV, −5 mV, 0 mV, +5 mV, +10 mV, +15 mV, +20 mV, +25 mV, +30 mV, +35 mV, +40 mV, +45 mV, +50 mV, +55 mV, +60 mV, +65 mV, +70 mV, +80 mV, +85 mV, and/or +90 mV. For each potential, the electrical current may be measured and compared with one or more reference electrical currents. In some embodiments, a reference electrical current Is measured in an open, unblocked pore. In some embodiments, a reference electrical current is measured in a modified ClyA pore that is bound to a known protein, for example, a protein whose presence or absence will be determined in solution.

In some embodiments, a modified ClyA pore as described herein may be conjugated to one or more aptamers. When more than one aptamer is conjugated, the aptamers may be the same aptamer or may be different aptamers. The one or more aptamers may be conjugated to a cysteine residue in the modified ClyA pore. In some embodiments, a modified ClyA pore comprises a cysteine residue in place of another amino acid residue in the pore. This cysteine residue substitution may be combined with other amino acid substitutions, deletions, and/or additions made relative to the wild-type pore protein. For example, modifications within the pore lumen may be engineered to after the size, binding properties, and/or structure of the pore. In some embodiments, cysteine residues are substituted with other amino acids such as serine residues. The modified pore protein may be a pore comprising multiple subunits, for example, 12 subunits, in which at least one subunit comprises a modified amino acid. In certain embodiments, the modified ClyA is from a gram-negative bacteria such as *Salmonella* or *Escherichia coli* (*E. coli*). In some embodiments, the modified cytolysin is a modified ClyA from *Salmonella typhi* (*S. typhi*) or *Salmonella paratyphi* (*S. paratyphi*). In some embodiments, the modified A modified ClyA pore comprises 12 subunits, each subunit comprising a sequence shown in SEQ ID NO: 2.

An aptamer may be a nucleic acid aptamer comprising DNA, RNA, and/or nucleic acid analogs. An aptamer may be a peptide aptamer, such as a peptide aptamer that comprises a variable peptide loop attached at both ends to a scaffold. Aptamers may be selected to bind to a specific target protein analyte. In certain embodiments, two or more aptamers are conjugated to the same modified ClyA pore. For example, 5, 6, 7, 8, or 9 aptamers may be conjugated to a modified ClyA pore. Alternatively, 10, 11, or 12 aptamers may be conjugated to a modified ClyA pore. If more than one aptamer is conjugated to the modified ClyA pore, the aptamers may be positioned at least 2 nm apart.

In certain embodiments, a modified ClyA pore as described herein is combined with one or more peptide ligands. Peptide ligands may be attached to the modified ClyA pores via disulfide linkages, cross-linking, and/or chemical ligation. The modified ClyA pore may also be engineered as a fusion protein in which one or more peptide ligands is fused to at least one subunit of the modified ClyA pore. In some embodiments, the modified ClyA pore is combined more than one peptide ligand. The peptide ligands may be the same ligand or may be different ligands. Exemplary peptide ligands include, but are not limited to, receptors, antibodies, inhibitors, activators, and/or other peptide ligands that bind to target proteins.

Target Analytes

1. Protein Analytes

In some embodiments, the modified ClyA pore protein is engineered to allow protein analytes to bind within the lumen of the pore. This binding mediates a robust, reproducible current block, which is readily distinguished from the unblocked ionic currents measured in unbound pores. The protein analytes may range from 15-70 kDa in molecular weight, for example, exemplary protein analytes may have a molecular weight of 15, 20, 25, 30, 35, 40, 45, 50, 55, 60, 65, or 70 kDa. The analyte may be a dimer or other multimer of a smaller protein.

In some embodiments, the modified ClyA pore proteins comprise more than one site of binding and/or residence for protein analytes. For example, a modified ClyA pore protein may comprise two sites: level 2 may be associated with residence of the protein analyte at a deep, more sterically constrained site, while the level 1 may be associated with residence of the protein analyte at a position closer to the wider cis entrance of the pore. Protein analyes may move between the two sites, thus eliciting two current levels seen within the same current blockade event. Thus, a modified ClyA pore proteins may provide more than one (i.e., two) current level measurement upon binding to a protein analyte.

In some embodiments, the modified ClyA-CS pores as described herein are capable of detecting and quantifying protein analytes. The modified ClyA pores may distinguish between homologs of the same protein, for example, bovine thrombin and human thrombin.

a. Detection and Identification of Proteins

Another aspect of the present disclosure relates to detection of specific proteins in a sample. In some embodiments, a method for detecting the presence of at least one protein analyte in a sample comprises (a) contacting the sample with a modified ClyA pore as disclosed herein; (b) applying one or more electrical potentials across the modified ClyA pore; (c) measuring current passing through the modified ClyA pore at each of the one or more electrical potentials; and (d) comparing measured currents with reference currents, wherein a change in currents relative to the reference currents indicates the presence of the protein analyte in the sample. In some embodiments, the change in currents is a decrease in current. In some embodiments, a target protein has a molecular weight in the range of 15-50 kDa, for example, a molecular weight of 15, 20, 25, 30, 35, 40, 45, or 50 kDa. The reference current may be a current measured through the modified ClyA pore in the absence of a ligand, and/or a current measured through the modified ClyA pore in the presence of a reference ligand. In some embodiments, the reference ligand and the protein analyte are identical. In certain embodiments, the reference ligand and the protein analyte are at least 75%, 80%, 85%, 90%, or 95% identical. Thus, in some embodiments, a method for identifying a protein analyte in a sample comprises (a) contacting the sample with a modified ClyA pore as described herein; (b) applying one or more electrical potentials across the modified ClyA pore; (c) measuring currents passing through the modified ClyA pore at each of the one or more electrical potentials; and (d) comparing measured currents with one or more reference currents from a known ligand, wherein a match between the measured currents and the reference currents indicates the protein analyte and the known ligand are identical. Similarly, a non-match between the measured currents and the reference currents may indicate that the protein analyte and the known ligand are not identical.

In some embodiments, the modified ClyA pore comprises amino acid substitutions, deletions, and/or additions, as compared with the wild-type pore protein. For example, modifications within the pore lumen may be engineered to alter the size, binding properties, and/or structure of the pore. In some embodiments, cysteine residues are substituted with other amino acids such as serine residues. The modified pore protein may be a pore comprising multiple subunits, for example, between 7-11 subunits, 12 subunits, 13 subunits, or 14 subunits, in which at least one subunit comprises a modified amino acid. In certain embodiments, the modified ClyA is from a gram-negative bacteria such as Salmonella or Escherichia coli (E. coli). In some embodiments, the modified cytolysin is a modified ClyA from Salmonella typhi (S. typhi) or Salmonella paratyphi (S. paratyphi). In some embodiments, the modified A modified ClyA pore comprises 12 subunits, each subunit comprising a sequence shown in SEQ ID NO: 1.

In certain embodiments, varying electrical potentials are applied across the modified ClyA pore. For example, the electrical potential applied across the modified ClyA pore may range from −90 mV to +90 mV. The electrical potential may be −90 mV, −85 mV, −80 mV, −75 mV, −70 mV, −65 mV, −60 mV, −55 mV, −50 mV, −45 mV, −40 mV, −35 mV, −30 mV, −25 mV, −20 mV, −15 mV, −10 mV, −5 mV, 0 mV, +5 mV, +10 mV, +15 mV, +20 mV, +25 mV, +30 mV, +35 mV, +40 mV, +45 mV, +50 mV, +55 mV, +60 mV, +65 mV, +70 mV, +80 mV, +85 mV, and/or +90 mV. At each voltage, the electrical current may be measured and compared with one or more reference electrical currents. In some embodiments, a reference electrical current is measured in an open, unblocked pore. In some embodiments, a reference electrical current is measured in a modified ClyA pore that is bound to a known protein, for example, a protein whose presence or absence will be determined in solution.

In certain embodiments, the interaction of a protein analyte with a modified ClyA pore provokes current blocks as compared to open, unbound pores. The amplitude of the current block may be measured as the residual current percentage (IRES) of the open pore current. In some embodiments, characteristic current blocks are used to identify a specific protein analyte. For example, current blocks may be short, quick current spikes. Current blocks may be transient, or may last for more than 1 minute. Current blocks may be shallow or may be deep. A shallow current level may be indicated by an IRES value of about 41-100%, indicating that the target protein analyte leaves a residual current that is about 41%, 45%, 50%, 55%, 60%, 65%, 70%, 75%, 80%, 85%, 90%, 95%, or 100% of the open pore current. Conversely, a deep current level may be Indicated by an IRES value of about 0-40%, indicating that the target analyte leaves a residual current that is about 0%, 5%, 10%, 15%, 20%, 25%, 30%, 35%, or 40% of the open pore current. In some embodiments, a current block comprises more than one current level, for example, a current block may comprise a shallow current level and a deep current level. In one exemplary modified ClyA pore, a target analyte may provoke a first current block with an IRES value of about 70% as well as a second current block with an IRES value of about 15%. In certain embodiments, the presence and/or identity of a protein analyte is determined by comparing the shallow and deep current levels from the protein analyte with shallow and deep current levels from a reference ligand. The inter-conversion between shallow and deep current levels may be compared, for example, IRES values may be compared, the rate of conversion between shallow and deep current levels may be compared, the relative durations of the shallow and deep currents levels may be compared, and/or the number of shallow and deep current levels may be compared.

For any target protein analyte, when the voltage across the modified ClyA pore is varied, the percentage of shallow and/or deep current levels may also vary. The distribution of shallow and/or deep current levels may differ from one target protein analyte to another target protein analyte. Thus, in some embodiments, two or more target analytes are distinguished from one another on the basis of their current level measurements. Two or more target protein analytes may be distinguished by the intensity and duration of their current blocks and/or by their distributions of current levels. For example, a first protein may show a large decrease in the percentage of shallow levels as the voltage across the pore is increased, while a second protein may show a more gradual decrease.

In certain embodiments, the two or more target proteins about 95%, 90%, 85%, 80%, 75%, or 70% identical. In certain embodiments, the two or more target proteins or their subunits are about 65%, 60%, 55%, 50%, or 45% identical. In some embodiments, the two or more target proteins are species-specific forms of the same protein.

2. Translocation of Nucleic Adds

One aspect of the present disclosure is a modified ClyA pore that is capable of binding, detecting, identifying, translocating nucleic acids and/or modulating transport of nucleic acids. Nucleic acids which translocate through the modified ClyA pores include but are not limited to DNA, which may or may not carry posttranslational modifications such as methylation; RNA such as transfer RNA (tRNA), messenger RNA (mRNA), ribosomal RNA (rRNA), small interfering RNA (siRNA), micro RNA (miRNA), small nucleolar RNA (snoRNA), small nuclear RNA (snRNA), extracellular RNA (exRNA), Piwi-interacting RNA (piRNA), and any non-coding RNA (ncRNA). Nucleic acid analogs such as 2'-O-methyl substituted RNA, locked nucleic acid (lNA), morpholino, and peptide nucleic acid (PNA), dideoxynucleotides, etc.

In certain embodiments, the modified ClyA pores are engineered to translocate DNA such as ssDNA or dsDNA. While ssDNA in particular may not enter a modified ClyA pore at physiological salt conditions due to replusive charges from negatively-charged residues in the lumen, DNA translocates through modified ClyA pores as described herein under conditions of high ionic strength. In some embodiments, conditions of high ionic strength are (or have the equivalent to the ionic strength of) a 2.5 M NaCl solution. In certain embodiments, conditions of high ionic strength are higher than the ionic strength of a 2.5 M NaCl, for example, conditions of high ionic strength may be be (or may be equivalent to the ionic strength of) a 2.75 M, 3 M, 3.25 M, 3.5 M, 3.75 M, 4 M, 4.25 M, 4.5 M, 4.75 M, or 5 M NaCl solution and/or may be (or may be equivalent to) 2.75 M, 3 M, 3.25 M, 3.5 M, 3.75 M, 4 M, 4.25 M, 4.5 M, 4.75 M, or 5 M KCl solution. The negatively charged residues lining the internal lumen of the ClyA pore may be screened under these conditions. For example, in 2.5 M NaCl, 15 mM Tris-HCl at pH 7.5, addition of ds DNA to a modified ClyA pore as described herein at +100 mV may produce a short current blockade due to translocation of dsDNA through the pore. As demonstrated herein, dsDNA translocates the modified ClyA pores under these conditions. In addition, ssDNA may translocate the modified ClyA pores, for example under conditions of high ionic strength and/or in a folded structure. ssDNA may translocate modified ClyA pores at a different rate than dsDNA.

Accordingly, one aspect of the present disclosure is a method for translocating DNA, for example dsDNA through a modified ClyA pore that is capable of translocating DNA, comprising the steps of obtaining a modified ClyA pore as described herein, applying a voltage of at least +50 mV across the modified ClyA pore, adding a sample containing the DNA to the cis opening of the modified ClyA pore, and measuring the current flowing through the pore. A current blockade indicates translocation of the DNA. Current may be restored by reversing the potential to a negative potential, such as −100 mV or −50 mV. In some embodiments, the modified ClyA pore is used under conditions of high ionic strength.

In some embodiments, the modified ClyA pore for translocating DNA comprises a modified ClyA pore as described herein. The modified ClyA pores may be engineered to translocate nucleic acids. For example, the modified ClyA pore may comprise at least 12 subunits, wherein each subunit comprises a polypeptide represented by an amino acid sequence at least 80% identical to SEQ ID NO:1, wherein exactly one Cys residue is substituted with Ser. Each subunit may be represented by an amino acid sequence that is at least 85%, 90%, 95%, 96%, 96%, 98%, or 99% identical to SEQ ID NO:1, and additionally exactly one Cys residue may be substituted with Ser. The Cys residue may be Cys 87 and/or Cys 285 in SEQ ID NO:1. In some embodiments, the Cys residue is Cys285. Other amino acid residues may be substituted, for example, with amino acids that share similar properties such as structure, charge, hydrophobicity, or hydrophilicity. In certain embodiments, substituted residues are one or more of L99, E103, F166, and K294. For example, the substituted residues may be one or more of L99Q, E103G, F166Y, and K294R. Thus, each subunit may comprise a polypeptide represented by an amino acid sequence of SEQ ID NO:2. An exemplary modified ClyA pore comprising subunits in which exactly one Cys residue is substituted with Ser may be called ClyA-CS.

In some embodiments, the modified ClyA pore recognizes and chaperones a specific DNA molecule across a biological membrane under a fixed transmembrane potential. The reaction mechanism may be based on DNA strand displacement. For example, a DNA moiety may be conjugated to a nanopore in order to allow the transport of selected DNA molecules across the nanopore via the DNA strand displacement reaction. In certain embodiments, the modified ClyA pore comprises at least 12 subunits, wherein each subunit comprises C87S, C285S, and D103C substitutions, and each subunit is conjugated to an oligonucleotide. Accordingly, in some embodiments, a method for translocating dsDNA comprises (a) obtaining a modified ClyA pore comprising at least 12 subunits, wherein each subunit comprises C87S, C285S, and D103C substitutions and is conjugated to an oligonucleotide; (b) applying a voltage of +50 mV across a modified ClyA pore as described herein, (c) adding a sample containing a dsDNA to the cis opening of the modified ClyA pore, (d) adding to the cis opening of the modified ClyA pore a first single stranded nucleic acid comprising (i) a sequence that is complementary to at least 15 nucleobases of the oligonucleotide that is conjugated to the ClyA pore, and (ii) a sequence is that is complementary to at least 12 nucleobases of the double stranded DNA; and measuring the current across the modified ClyA pore, wherein a decrease in current after step (d) indicates translocation of the double stranded DNA through the modified ClyA pore.

In some embodiments, the method optionally comprises adding to a trans opening of the modified ClyA nanopore a second single stranded nucleic acid comprising a sequence that is complementary to the first single stranded nucleic acid. Here, an increase in current across the modified ClyA pore after adding the second single stranded nucleic acid to a trans opening of the modified ClyA pore indicates that the double stranded DNA has translocated completely through the pore.

A further aspect of the present disclosure relates to a device for translocating DNA, comprising: a fluid-filled compartment separated by a membrane into a first chamber and a second chamber; electrodes capable of applying potential across the membrane; one or more nanopores inserted in the membrane; a solution of high ionic strength in one chamber of the membrane, wherein DNA translocates through the nanopore from the first chamber to the second chamber. In certain embodiments, the DNA is double stranded. The nanopores may be ClyA pores, for example, the modified ClyA pores described herein. The pores, such as modified ClyA pores, may have an inner diameter of at least 2.2 nm. In some embodiments, the membrane is an artificial lipid bilayer. In some embodiments, the potential across the membrane ranges from −100 mV to +100 mV. The solution of high ionic strength may comprise 2.5M NaCl.

EXAMPLES

Having provided a general disclosure, the following examples help to illustrate the general disclosure. These specific examples are included merely to Illustrate certain aspects and embodiments of the disclosure, and they are not intended to be limiting in any respect. Certain general principles described in the examples, however, may be generally applicable to other aspects or embodiments of the disclosure.

Example 1. Tuning the Property of ClyA by Directed Evolution

Figure 7A:
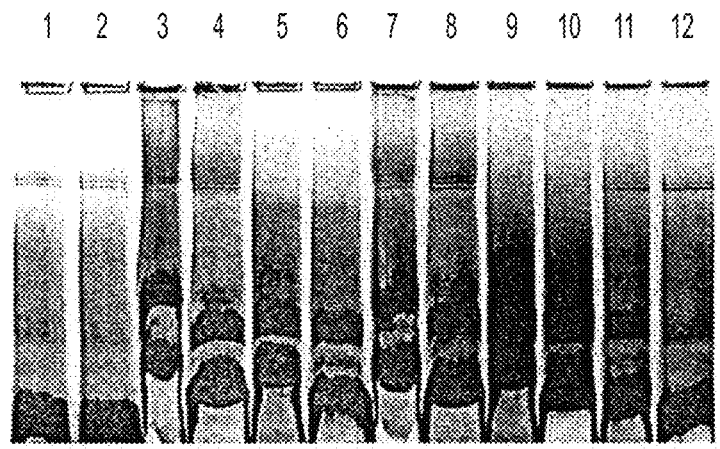
FIGS. 7A-7B show an example of the screening of the oligomerization of ClyA variants using 4-20% acrylamide BN-PAGE.
Figure 7B:
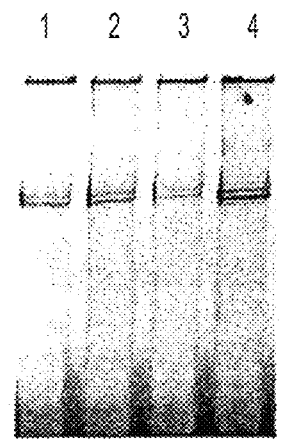
Figure 8:
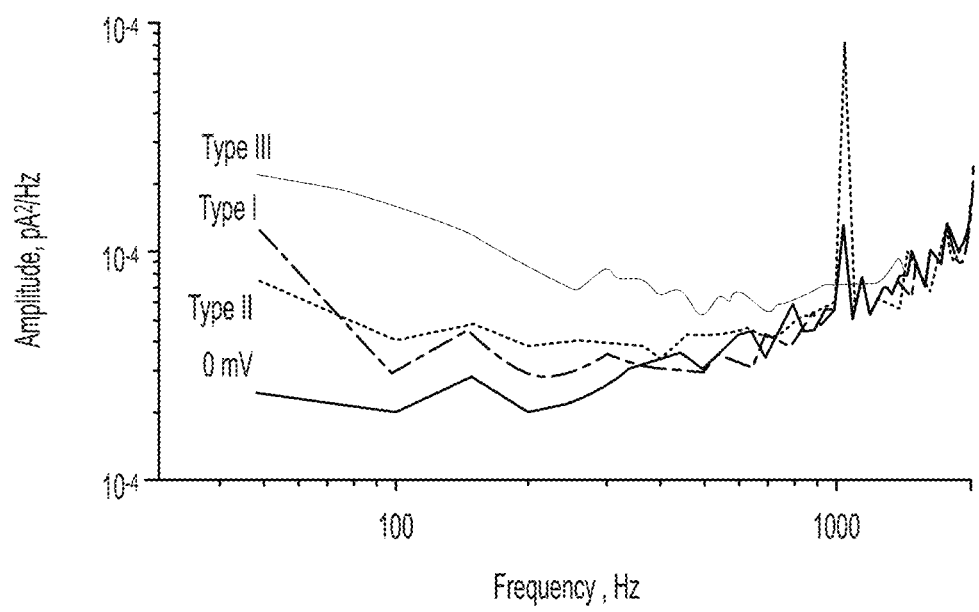
FIG. 8 shows noise characteristics of three types of ClyA nanopores under −35 mV potential in 150 mM NaCl, 15 mM Tris.HCl. Current power spectral densities of the Type I (dashed line), Type II (dotted line) and Type III (light gray solid line) ClyA-CS nanopores at −35 mV obtained from 0.5 s traces. The current power spectral density at 0 mV is shown in black. Each line corresponds to the average of power spectra calculated from 3 recordings carried out on different single channels.

Directed evolution approaches for tailoring enzymes with desired properties were used to improve the activity of ClyA-SS, reasoning that mutations that compensate for the deleterious effects of C87S and C285S substitutions would also increase stability of the nanopore in lipid bilayers. Random libraries were generated on the background of ClyA-SS by error prone PCR (approximately 1-4 mutations per gene per round) and screened for hemolytic activity (FIG. 6). The most active variants were then purified by Ni-NTA affinity chromatography and tested for oligomer formation by BN-PAGE (FIG. 7). Selected nanopore variants were finally screened in planar lipid bilayers for the desired behavior (low electrical noise and ability to remain open at high applied potentials), which served as final and critical criteria for selection. After just four rounds of screening, ClyA-CS variants were isolated (Table 1) that showed low electrical noise (FIG. 8) and remained open in planar lipid bilayers from +90 to −150. Remarkably, the serine at position 87 converted back to cysteine, the original residue in the wild-type gene. In order to obtain a cysteine-less ClyA variant amenable to site-specific chemical modification, ClyA-CS was subjected to saturation mutagenesis at position 87, the resulting library was screened, and cysteine-less ClyA-AS with desired electrical properties (SI) was selected. In contrast to ClyA-SS, evolved ClyA nanopores expressed in E. coli cells in the soluble fraction (FIG. 6) and the monomers could be purified in one-step by affinity chromatography, which allowed a ten fold increase in the production yield (~0.6 mg per 10 ml culture).

Example 2. Isolation of ClyA Nanopores with Different Size

Figure 2A:
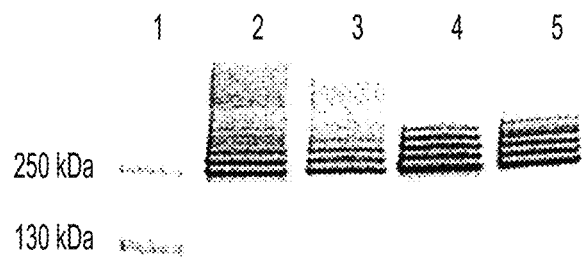
FIGS. 2A-2B show the oligomerization and nanopore formation of ClyA-WT, ClyA-SS and evolved ClyA variants.

ClyA oligomers, formed by incubation of ClyA monomers with 0.5% w/v β-dodecyl maltoside (DDM), revealed multiple bands on a BN-PAGE (FIG. 2a), suggesting that ClyA might assemble into several oligomeric states. This is particularly intriguing, since the exact stoichiometry of E. coli ClyA oligomerisation is controversial. The ClyA crystal structure (PDB_ID: 2WCD) revealed a dodecamer with a 5.5 nm opening on the cis side and a 3.3 nm opening at the trans entrance (including Van der Waals radii of the amino acid side chains), while earlier cryo-EM structures revealed nanopores with $8^{11}$ or $13^{12}$ subunits.

Figure 2B:
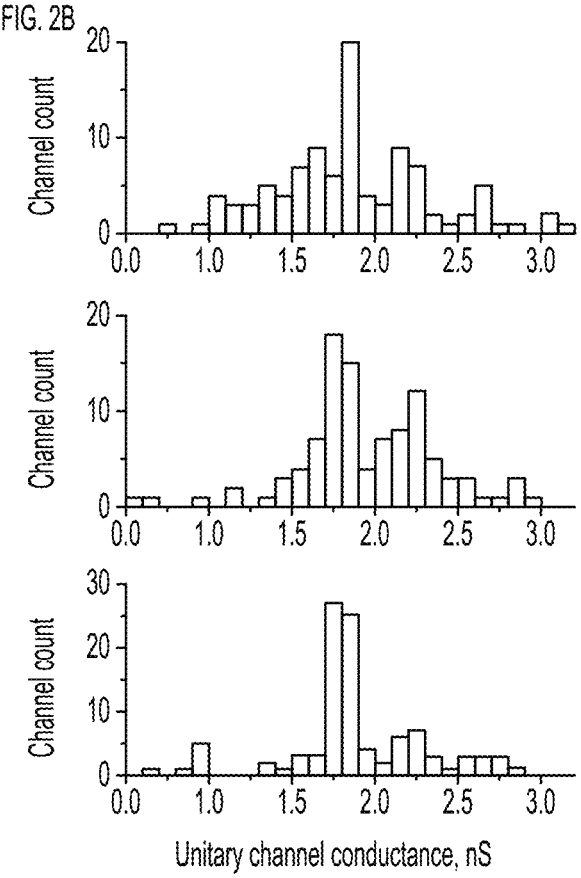

In planar lipid bilayers, ClyA-WT pre-incubated with DDM showed a wide distribution of open nanopore conductances spanning approximately 2 nS (FIG. 2b, top), suggesting that also in lipid bilayers ClyA-WT might assemble into nanopores of different size and/or geometry. The major peak in the distribution of ClyA-WT unitary conductance (Type I ClyA) represented only 24% of the reconstituted nanopores and showed an average conductance of 1.83±0.06 nS in the conductance range from 1.7 to 1.9 nS (−35 mV, 15 mM Tris.HCl pH 7.5 and 150 mM NaCl). The distribution of ClyA-CS open pore conductance showed two major peaks: the first included 37% of the reconstituted nanopores and corresponded to Type I ClyA-CS (1.79±0.05 nS); while the second (Type II ClyA-CS) included 23% of the nanopores and showed an average conductance of 2.19±0.09 nS (conductance range 2.1-2.4 nS, FIG. 2b, middle). ClyA-WT and ClyA-AS also showed small percentage of Type II ClyA (18% and 16%, respectively). The unitary conductance of ClyA-AS was especially uniform with 52% of the reconstituted nanopores corresponding to Type I ClyA (FIG. 2b, bottom).

Figure 3A:
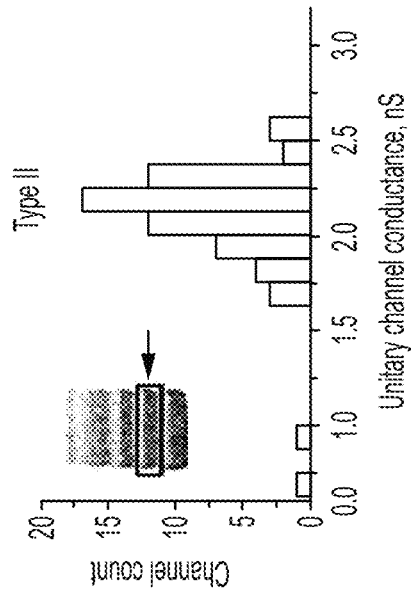
FIGS. 3A-3C show the unitary conductance of 62 ClyA-CS nanopores extracted from the lowest (FIG. 3A), second lowest (FIG. 3B) and third lowest (FIG. 3C) oligomeric band of ClyA-CS separated on 4-20% acrylamide BN-PAGE. ClyA-CS monomers were pre-incubated in 0.5% DDM and loaded on a BN-PAGE as described in FIG. 2. The bands that were excised are boxed and marked with an arrow on the insets. Recordings were carried out at −35 mV, 28° C. in 15 mM Tris.HCl pH 7.5 containing 150 mM NaCl.
Figure 3B:
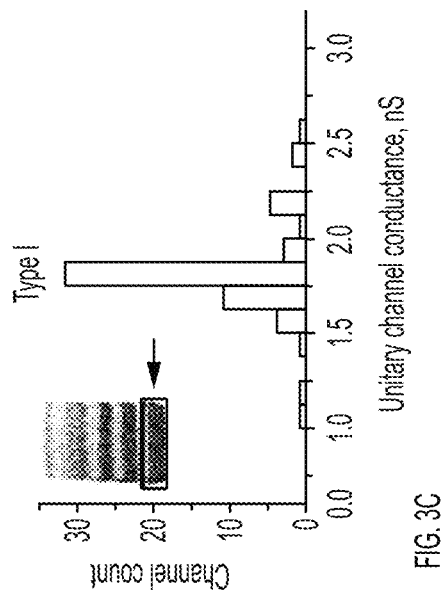
Figure 3C:
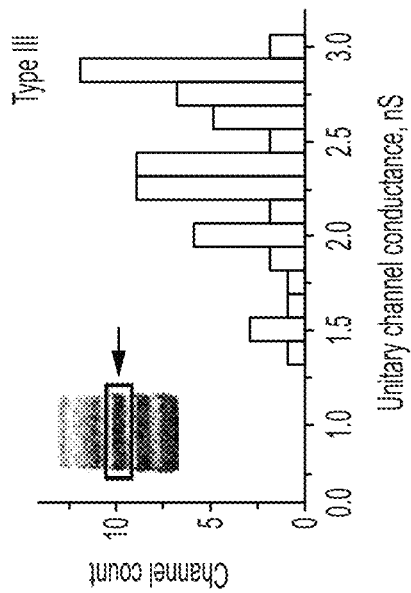

To establish whether the different bands of ClyA oligomers corresponded to nanopores with different size, ClyA-CS were extracted from the three major oligomeric bands in the BN-PAGE, and measurements were made of the unitary open nanopore conductance of 62 nanopores derived from each band within two days from gel extraction. 62% of ClyA-CS oligomers from the lowest band formed Type I ClyA-CS nanopores (1.78±0.04 nS, FIG. 3a), while 68% of nanopores extracted from the second lowest band (FIG. 3b) reconstituted as Type II ClyA-CS nanopores (2.19±0.09 nS). Interestingly, 42% of the nanopores extracted from the third band reconstituted in lipid bilayers as a third nanopore type (Type III ClyA) that showed an average conductance of 2.81±0.11 nS in the conductance range 2.5-3.0 nS (FIG. 3c).

Taken together, these results show that the three major bands of ClyA oligomers observed on the BN-PAGE correspond to three distinct nanopore types with different size and different unitary conductance. This finding is consistent with reports that high order symmetrical oligomeric structures are often permissive with respect to subunit stoichiometry.[13] Therefore it can be hypothesized that Type I ClyA most likely represents the 12mer of the crystal structure, while Type II ClyA might be the 13mer observed in earlier cryo-EM studies. Both nanopores showed low electrical noise (FIG. 8) and remained open over a wide range of applied potentials (from +90 mV to −150 mV). Type III ClyA-CS nanopores, which showed higher noise than Type I and Type II nanopores (FIG. 8) and frequently gated especially at applied potentials lower than −40 mV and higher than +50 mV, may correspond to a 14mer version of ClyA not observed before.

Example 3. HT as Molecular Caliper to Test ClyA Nanopores of Different Size

The ability to employ nanopores with identical amino acid composition but different size is a new feature in the biological nanopore field and is important because the size of a nanopore defines its ability to capture and study a particular molecule.[10b, 14] It has been previously shown[7a] that at −35 mV HT (human thrombin, 37 kDa) inflicted well-defined current blockades to Type I ClyA-SS nanopores that lasted for several minutes. The blockade signal switched rapidly between two current levels, level 1 [percentage of the open nanopore current ($I_{RES \%}$)=56 t 1%] and level 2, ($I_{RES \%}$=23 t 1%, Table 1, and FIG. 4a), reflecting two residence sites for HT within the lumen of the ClyA nanopore. Level 2 is most likely associated to HT residence at a deep site, while level 1 is associated to the residence of HT closer to the cis entrance of the nanopore.[7a] Because thrombin provoked such a well-defined pattern of current blockades HT was used here as a molecular caliper to compare the geometries of the different ClyA nanopores.

At −35 mV HT current blockades to Type I ClyA-CS nanopores were identical to that of Type I ClyA-SS nanopore (Table 1), confirming that mutations accumulated in the variants disclosed herein most likely did not change the size and geometry of the ClyA nanopore. HT current blockades to Type II ClyA also switched between the two current levels, but their relative distribution was different. In Type I ClyA-CS HT mostly lodged at the more superficial binding site (70% occupancy), while in Type II ClyA-CS HT preferred the binding site deeper within the nanopore (96% occupancy). These results suggest that both ClyA Types most likely retain similar overall nanopore architecture but provide different steric hindrance to HT. HT blockades to Type III ClyA were fast (55±48 ms) and showed only a level 2 current block ($I_{RES\%}$ of 32±9%), suggesting that Type III ClyA is large enough to allow unhindered translocation of HT through the nanopore (see below).

Example 4. Protein Translocation Through ClyA Nanopores

Figure 5A:
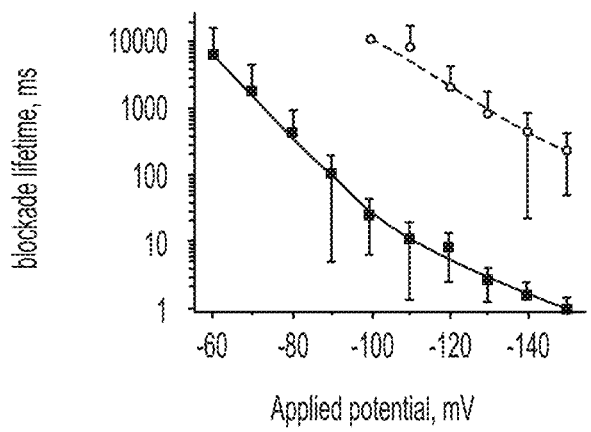
FIGS. 5A-5C show protein translocation through Type I and Type II ClyA-CS nanopores.
Figure 5B:
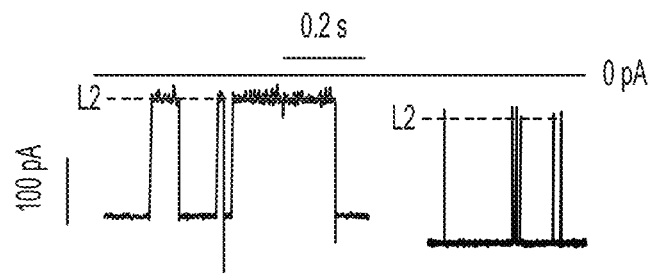
Figure 9B:
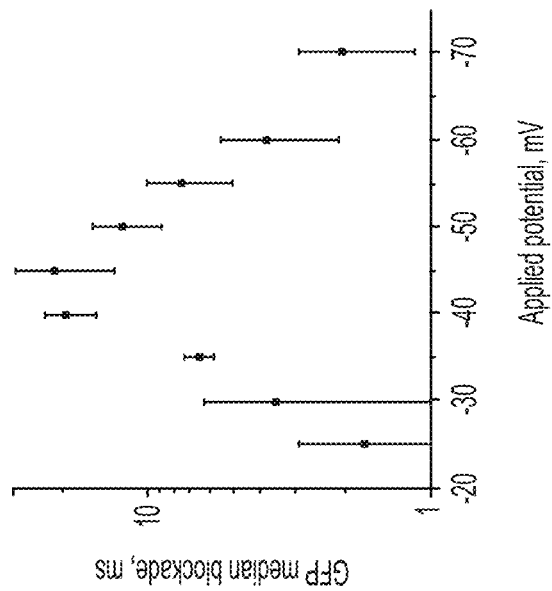
FIGS. 9A-9B show the duration of HT (FIG. 9A) and FP (FIG. 9B) blockades on Type I ClyA-SS pores. Traces were recorded at a sampling rate of 10 kHz with an internal low-pass Bessel filter set at 2 kHz. Each plotted value corresponds to the average determined using at least 3 different single channels. Errors are given as standard deviations.
Figure 9A:
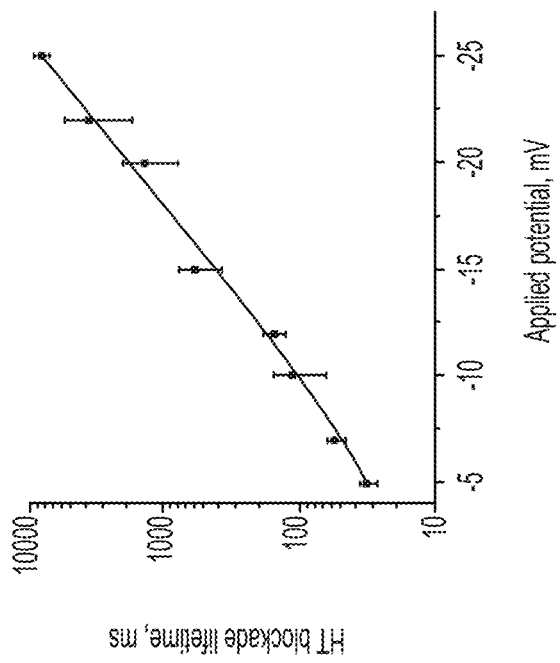
Figure 17B:
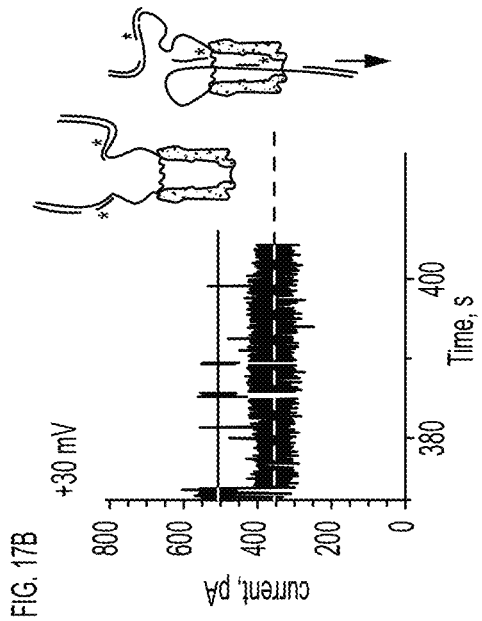
FIGS. 17A-17F show dsDNA current blockades to ClyA-CS. On the right of each current trace the cartoon represents the physical interpretation of the current recordings.
Figure 17D:
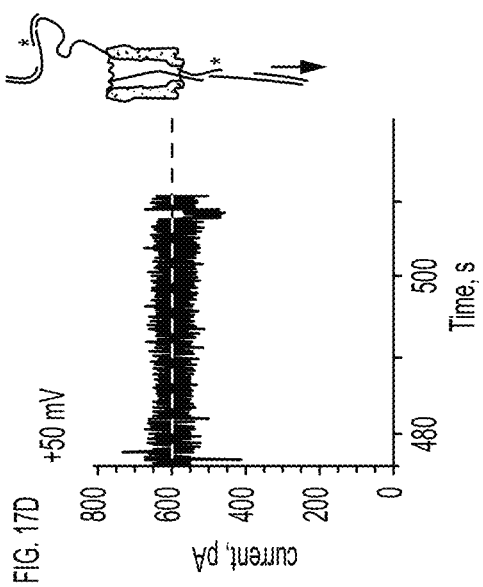
Figure 17A:
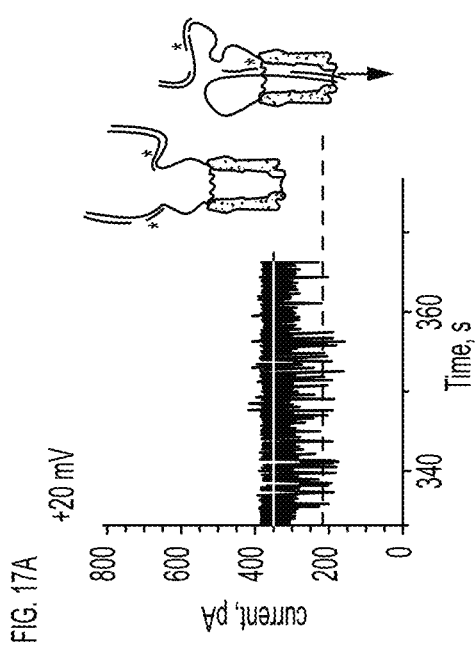
Figure 17C:
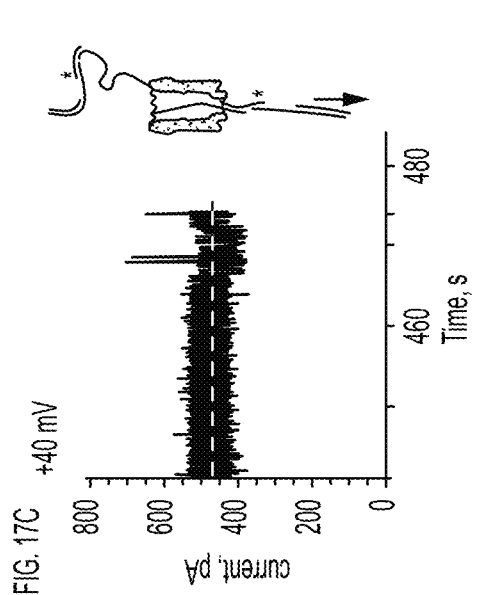
Figure 17F:
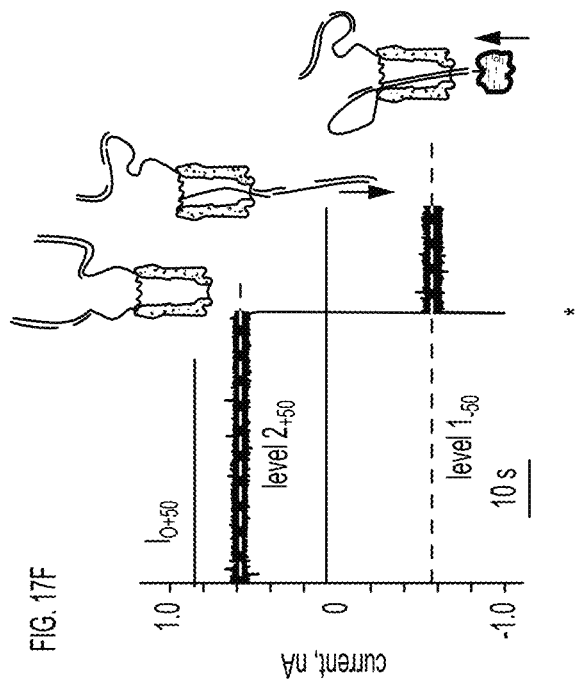
Figure 17E:
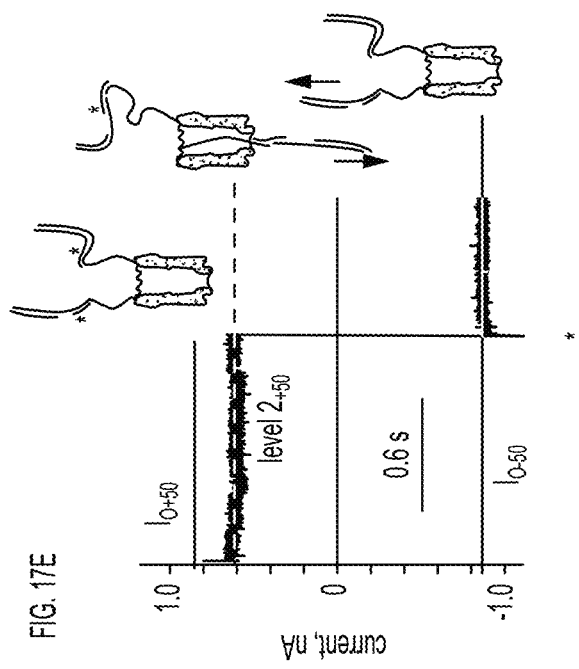

Thrombin is a globular protein with a molecular volume that can be approximated to a sphere with diameter of 4.2 nm (SI). Therefore, assuming that Type I, II and III ClyA correspond to nanopores with different oligomeric state (see above), HT should not easily translocate through Type I and Type II ClyA nanopores (trans diameter, including the Van der Waals radii of the atoms, of 3.3 and 3.7 nm, respectively, Table 1). Contrary, HT has the same diameter as Type III ClyA (Table 1), suggesting that the protein might be capable of translocating through this nanopore. A powerful method to assess whether molecules pass through nanopores is to investigate the voltage dependence of the duration of the proteins current blockades. The decrease of the duration of the current blockades with increasing potential is strong evidence that the molecules translocate through the nanopore. By contrast, an increase in the duration of the current blockades with the voltage suggests that the proteins are driven into the nanopore but do not translocate through it.[10f, 15] From −5 mV to −25 mV the dwell time of HT blockades to Type I ClyA-SS nanopores increased with the applied potential (FIG. 9a), suggesting that HT does not translocate through the nanopores in this voltage interval. Taking advantage of the fact that Type I and Type II evolved ClyA nanopores remained open at applied potentials up to −150 mV, HT blockades were characterized on Type I and II ClyA-CS nanopores from −60 to −150 mV. At applied potentials higher than −100 mV for Type I ClyA-CS nanopores and −60 mV for Type II ClyA-CS nanopores the dwell times of HT current blockades strongly decreased with Increasing potential (FIG. 5a), suggesting that in this potential range HT molecules translocate through the nanopores. Similarly, Dendra2_M159A (FP, a GFP like protein, 30 kDa protein) displayed an initial increase (from −25 mV to −40 mV) followed by a decrease of the duration of the current blockades (from −50 mV to −70 mV), suggesting that FP translocates through Type I ClyA-SS nanopores at potentials higher than −50 mV (FIG. 9b). Comparing the duration of HT blockades to Type I and Type II ClyA-CS nanopores at the same potential revealed that the translocation of HT through Type II ClyA-CS was about two orders of magnitude faster than for Type I ClyA-CS (FIG. 5b, Table 1), which is in line with the interpretation that Type I and Type II ClyA describe nanopores with different size.

Example 5. Folded Versus Unfolded Translocation

Figure 5C:
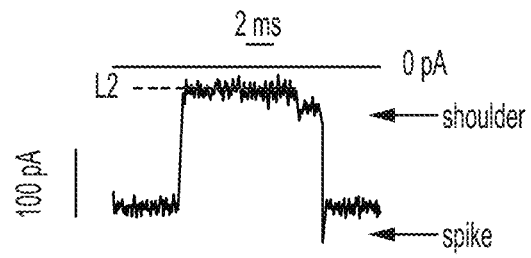

When a molecule is lodged within the lumen of a nanopore, the ionic current block is proportional to the atomic volume of the electrolytes being excluded by the molecule.[10d, 10f, 16] Therefore, if the molecule translocates through the nanopore with a folded structure, the $I_{RES\%}$ should remain constant at different applied voltages. In contrast, if a protein unfolds upon translocation, the $I_{RES\%}$ is expected to change, giving that the volume and shape of the unfolded polypeptide chain is different to that of the globular protein. The $I_{RES\%}$ values during the translocation of HT through Type I and Type II nanopores were identical at −35 mV and −150 mV (level 2, Table 1), suggesting that in this potential range HT does not unfold while in the nanopore. Interestingly, solely with Type I ClyA-CS nanopores, the current blockades of HT at potentials below −90 mV often terminated with a current block of higher $I_{RES\%}$ (shoulder) followed by a current increase (spike) with respect to the open nanopore current (FIGS. 5c and 10). Although the shoulder in the $I_{RES\%}$ values might Indicate that HT unfolds upon translocation, the current spikes that follows the protein translocation suggest otherwise that ClyA nanopores may need to deform in order to allow the translocation of folded HT through Type I nanopores.

Example 6: Translocation of dsDNA Through a ClyA Pore

In this work ClyA-CS was selected for its enhanced activity, solubility and favourable behaviour in planar lipid bilayers when compared to Wild Type ClyA The internal diameter of the ClyA dodecamers (3.8 nm at its narrower entrance,[17] FIG. 11a) is larger than the diameter of dsDNA (2.2 nm for the B form), indicating that dsDNA should readily electrophoretically translocate through the pore. However, most likely because of the negatively charged residues lining the lumen of ClyA (pI=5.1), at physiological salt concentrations ssDNA does not enter the nanopore.[7a] In view of previous work with alpha hemolysin (αHL) nanopores at high alkaline pH,[7b, 7c] the ability of DNA to translocate through ClyA-CS nanopores was tested at high ionic strength, where the internal charges of the pore are screened. In 2.5 M NaCl, 15 mM Tris.HCl pH 7.5 and under +100 mV applied potential, the addition of 0.12 μM of biotinylated dsDNA 1 (290 bp, Table 2) to the cis compartment produced transient current blockades ($I_B$) to the open pore current ($I_O$) showing a residual current ($I_{RES}=I_B/I_O$) of 0.63±0.01 (level $1*_{+100}$=1.10±0.03 nA, n=3 experiments), with 2.0±0.6 ms dwell time, due to the entrance of the DNA into the lumen of the pore (FIG. 11b). The subsequent addition to the cis compartment of 0.3 μM of neutravidin, which forms a tight complex with biotin, converted the transient blockades into long lasting current blockades (level $1_{+100}$=1.19±0.01 nA, n=4) with a higher residual current value ($I_{RES}$=0.68±0.01). The open pore current could be restored by reversal of the applied potential to −100 mV (FIG. 11b). These results suggest that neutravidin prevents the full translocation of DNA through ClyA nanopores by forming a cis protein:DNA complex where the DNA occupies the full length of the pore (FIG. 11c). Trans complexes could also be formed at −100 mV (level $1_{100}$=1.02±0.03 nA, $I_{RES}$=0.62±0.01, n=4) when the dsDNA:neutravidin complex is threaded through the trans side (FIG. 11d).

Example 7. A Rotaxane System Traps a dsDNA within a ClyA Nanopore

Rotaxanes are supramolecular interlocked systems in which a linear unit (thread) is translocated through a microcyclic ring and is tapped by two bulky substituents (stoppers). Such mechanically joined molecules have applications for example as switches in molecular electronics or as components in molecular machineries. Rotaxanes have been made from a variety of molecules including dsDNA[22] or by locking a biotinylated ssDNA molecules threaded through αHL nanopore with streptavidin on one side and with a DNA hairpin on the other side (dsDNA can not translocate through αHL).[23] Here to prove the translocation of dsDNA through ClyA nanopores a rotaxane system was built in which a dsDNA molecule added to the trans side of a ClyA nanopore hybridize with a second DNA strand on the cis side after threading through the lumen of the nanopore. A ClyA nanopore ClyA-2 was used, which contains 12 ssDNA molecules 2 (51 bases, Table 2, FIG. 12a) covalently attached at their 5' ends to cysteine residues introduced at the cis entrance of the pore (at position 103, FIG. 11a) via disulphide linkages. 2 is designed to act as a rotaxane stopper. The thread 3 is a dsDNA molecule (59 bp, Table 2) with an additional 31 nucleobases stretch of ssDNA at the 5' end that is designed to hybrize with the stopper at the cis side through hybridisation with oligo 6; and a 3' biotinylated linker that is used for complexation with neutravidin at the trans side. The linkage between the thread and stopper on the cis side is mediated by a bridging ssDNA molecule 4 (Table 2, FIG. 12a) that is complementary to the first 16 nucleobases of 2 and to the last 25 nucleobases of 3. When 3 and 4 are added to the trans compartment, at −100 mV the DNA thread is captured by the pore and not released from the pore upon reversing of the potential to +100 mV (level $2_{+100}$, $I_{RES}$=0.77±0.04, n=4), indicating that a DNA rotaxane is formed (FIG. 12b). Interestingly, at +100 mV the residual current of the rotaxane was higher than the $I_{RES}$ values of the cis or trans pseudorotaxane threads (0.68±0.01 and 0.62±0.01, respectively), suggesting that an unhybridized ssDNA stretch of 2 is likely to span the pore at this potential (FIG. 12b). The rotaxane could be disassembled by addition of 20 mM DTT to the cis chamber, which reduced the disulphide bond between 2 and ClyA and restored the open pore current at +100 mV (FIG. 12c-12e).

Selective Translocation Through ClyA-2 Pores.

The data indicate that ClyA-2 excludes non-specific DNA from the pore lumen of the pore, suggesting that the mesh ssDNA molecules attached to the pore might produce a steric and or electrostatic impediment for non-tethered DNA translocation. In addition, the DNA attached to the pore often occupies the pore lumen (FIG. 15c) thus preventing the entrance of other DNA molecules. When a specific DNA molecule is hybrised to ClyA-2, rapid DNA capture is observed at positive applied potentials. The concentration of ssDNA attached to the pore was previously estimated to be ~20 mM.[21] Therefore, augmented concentration of the dsDNA in the proximity of the pore mouth may enhance the capture of the specific DNA strands. In this case, unhybridized strands 2 might still be tethered to the pore, in which case the dsDNA construct might have to compete with the ssDNA 2 to enter the pore lumen.

Example 8. A Nanopore:DNA Device Utilizing a Strand Displacement Reaction

At high positive applied potentials, the ionic current of ClyA-2 nanopores fluctuated between the open pore level and several blocked pore levels (FIG. 12c, FIGS. 15 and 16a), suggesting the ssDNA molecules tethered to the top of the pore enter the lumen of ClyA but do not permanently thread to the trans side of the pore.[1c] Further suggesting this interpretation; at +100 mV the addition of a 90mer ssDNA Sa (Table 2) in complex with neutravidin to the cis side of ClyA-CS provoked transient current blockades (FIG. 13) that converted into long lasting DNA translocation events upon the subsequent addition of equimolar concentrations of the complimentary ssDNA 5b (Table 2, FIG. 13). The translocation of DNA through nanopores is often observed above a threshold potential[24-27] that can be tuned by modulating the charge distribution of the lumen of the pore,[26,27] or by changing the ionic strength of the solution.[7c,28] Therefore, most likely because of its lower charge density and/or higher flexibility, these findings indicate that ssDNA has higher threshold for DNA translocation than dsDNA (FIG. 13).

These results suggest that despite the applied potentials a ssDNA molecule attached to the cis entrance of ClyA is likely to sample the cis solution. On the other hand if the DNA molecule becomes double stranded (e.g. by strand hybridisation) at positive applied potential the dsDNA strand will translocate through the pore and sample the trans solution. Therefore, a nanopore:DNA device was designed in which the hybridisation of a specific DNA strand to the cis side of the nanopore promotes the translocation of the DNA hybrid through the pore. The DNA:nanopore complex is then disassembled by a strand displacement reaction (FIG. 14a), which will promote the transport of DNA across the bilayer and the return of 2 to sample the cis chamber. Conveniently, at positive applied potentials the addition of dsDNA molecules to the cis side of a ClyA-2 do not produce current blockades (FIG. 18), Indicating that the ssDNA molecules attached to ClyA-2 prevent or drastically reduce the translocation of DNA from solution. Therefore, the DNA unit atop of the nanopore might infer specificity to the system by promoting the translocation of specific DNA molecules while creating a barrier for the translocation of non-specific DNA. At +50 mV, the addition of 3 to the cls side of ClyA-2 did not produce current blockades, further confirming that the ssDNA molecules attached to ClyA-2 prevent the DNA in solution from entering the pore (FIG. 14b). Nonetheless, after the addition to the cis chamber of 6, which is complementary to the first 15 bases of 2 and to the last 12 nucleobases of 3 (Table 2), the dsDNA hybrid nanopore showed permanent current blockades with $I_{RES}$=0.70±0.02 (level $2_{+50}$=0.59±0.02 nA, FIG. 14c, n=5), the hallmark of DNA capture. The translocation of 3 to the trans side was confirmed by the formation of a rotaxane upon addition of neutravidin to the trans chamber (FIG. 14c-d, FIG. 17e-f). Crucially, 6 was designed to include a 10 nucleobases 5'-single-strand extension to serve as toehold for the dissociation of the rotaxane (FIG. 14a). Notably, the addition to the trans chamber of 7, a ssDNA molecule complementary to 6 (Table 2), released 3 from the nanopore by first hybridising to the toehold and then promoting strand displacement (FIG. 14a). This was observed by the restoration of the open pore current, because the ssDNA molecule tethered to ClyA returned to the cis side after 3 and 6 are released from the pore (FIG. 14d). Remarkably, the nanopore showed a succession of open and blocked current levels, reflecting a cycle of capture, translocation and release, as the DNA cargos are captured from the cis chamber, transported through the pore and released to the trans chamber (FIG. 14d).

Figure 18A:
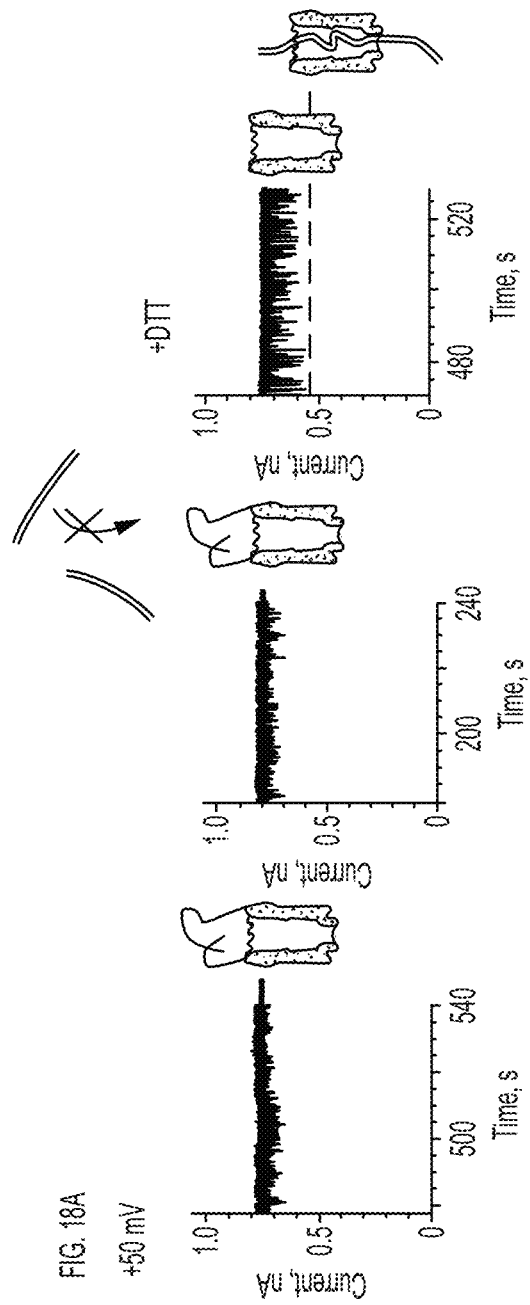
Figure 18B:
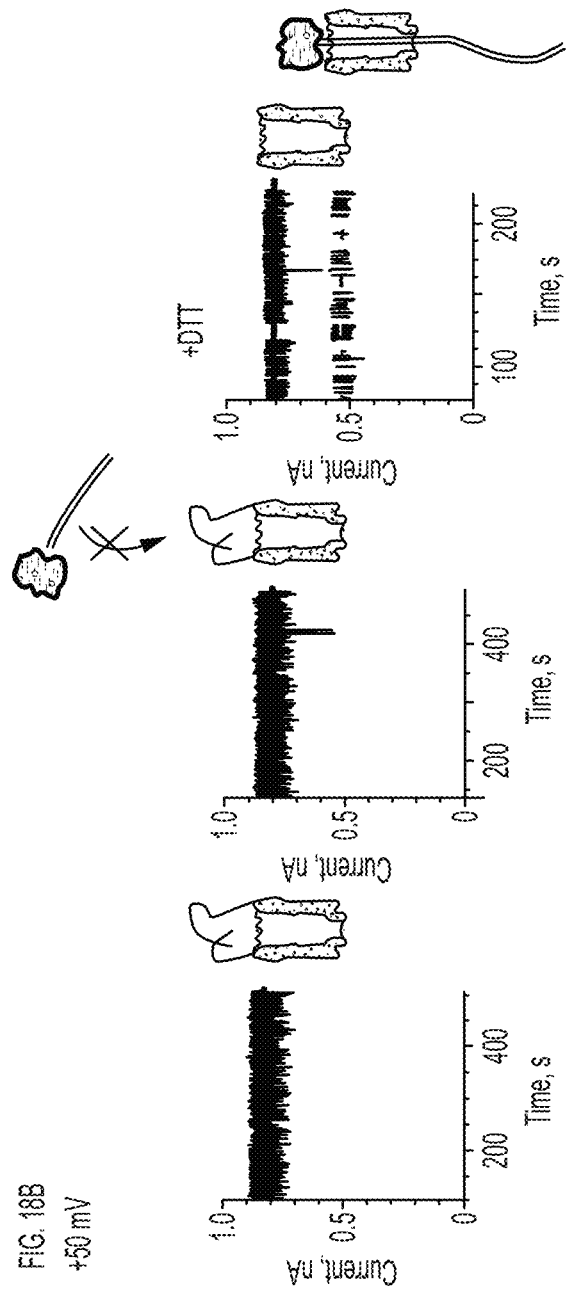
Figure 20:
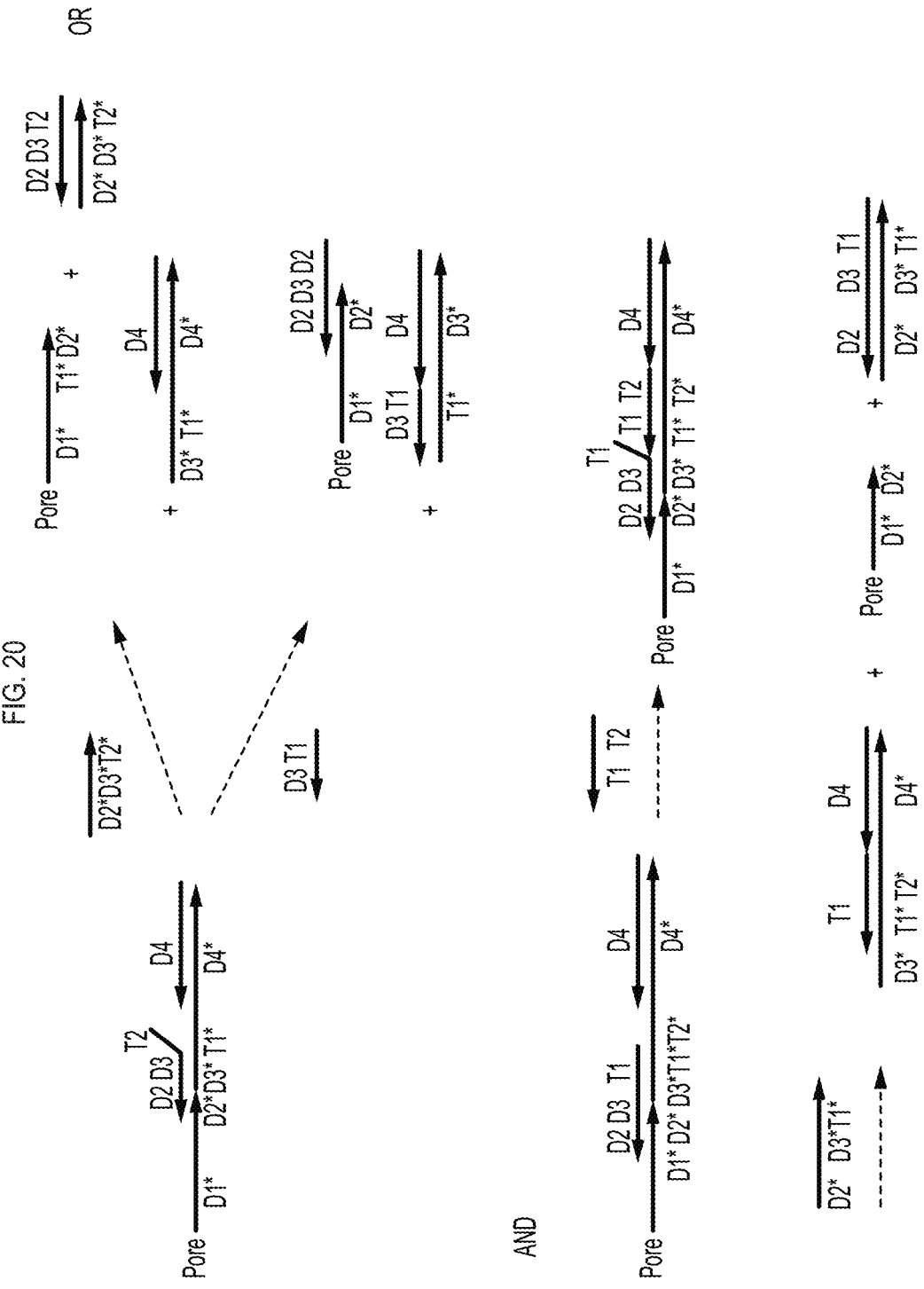
FIG. 20 shows strand release with Boolean logic. The OR gate is represented at the top and the AND gate at the bottom. DNA is represented as directional lines, with the arrow head denoting the 3' end. The sections within the same DNA strand represent DNA domains that act as a unit in hybridization, branch migration or dissociation. Domains are represented by the letter D followed by a number. T denotes a toehold domain. A starred domain represents a domain complementary in sequence to the domain without a star.

The DNA strands at the top of ClyA-2 nanopores drastically reduced the capture of non-specific DNA at both +50 and +100 mV (FIG. 18), suggesting that the DNA at the top of the pore prevented the translocation of dsDNA from solution. Notably, the applied potential was set to +50 mV and not at +100 mV because at +100 mV ClyA-2 occasionally produced long current blockades that were similar to typical events provoked by the capture of non-specific DNA (FIG. 18). Such current blockades were less frequent at lower applied potentials; hence the experiment was performed at +50 mV (FIG. 14) and +35 mV (FIG. 20). An additional reason to work at lower applied potential, as explained in the legend of FIG. 14, is that the frequency of DNA capture is reduced with the potential, thus at lower potentials the cycles of capture and release are more easily observed.

ssDNA vs dsDNA Translocation

Figure 19A:
Figure 19B:
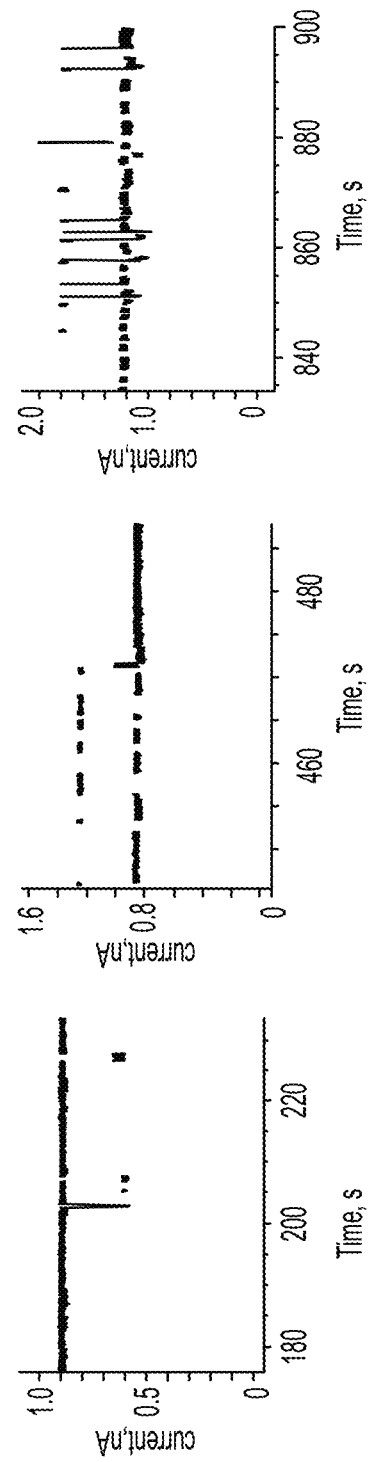

In the rotaxane configuration ssDNA molecules may be spanning the entire length of the pore at positive applied potentials. This is likely because at +100 mV the $I_{RES}$ value of the rotaxane (0.77) is higher than the $I_{RES}$ values of the cis- and trans-pseudorotaxanes (0.68 and 0.62, respectively, FIGS. 11c and 11d), which have a dsDNA immobilised within the pore. In addition, the unitary conductance values of the rotaxane as calculated from the slopes of the I-V curves were lower at positive applied potentials (10.8 nS) than at positive bias (13.0 nS, FIG. 16). Since ssDNA has a diameter (d=1 nm) is smaller than dsDNA (d=2.2 for the 8 form), these results further suggesting that ssDNA occupies the pore at positive bias. To further investigate the ability of ssDNA to span the pore, the ability of DNA hybrid 3, which is formed by a 3' biotinylated dsDNA section of 59 nucleobasepairs followed by a ssDNA stretch of 31 nucleobases at the 5' end, was tested for ability to translocate through ClyA-CS pores. At +100 mV, the addition of 3 in complex with neutravidin to the cis side of a ClyA-CS pore provoked long lasting current blockades with $I_{RES}$=0.67 (FIG. 19), the same $I_{RES}$ of a cis-pseudorotaxane (0.68), suggesting that at this potential the DNA hybrid translocate through ClyA and dsDNA spans the lumen of the pore. Since the translocation of 3 can only be initiated from the ssDNA end these results suggest that at +100 mV the ssDNA leading sequence is capable of translocating the lumen of ClyA. Interestingly, at +50 mV and +70 mV the current blockades were only transient (FIG. 19), suggesting that at this voltage ssDNA cannot pass the ClyA pore. The addition of strand 6, which is complimentary to the last 12 nucleobases of 3 produced long lasting current blockades +70 mV (FIG. 19), suggesting that threshold for DNA translocation is reduced.

Materials & Methods

Screening of ClyA Nanopores.

ClyA was expressed in E. Cloni® EXPRESS BL21 (DE3) cells (Lucigen) by using a pT7 plasmid. Transformants were prescreened on Brucella Agar with 5% Horse Blood (BBL™, Becton, Dickinson and Company), and individually grown and overexpressed in 96-deep-wells plates. Monomers from cell lysates were first screened for hemolytic activity on horse erythrocytes (bioMérieux) and then purified by using Ni-NTA affinity chromatography. Purified monomers were oligomerized in the presence of 0.5% β-dodecyl maltoside (GLYCON Biochemicals GmbH)[12] and loaded on native gel electrophoresis gels to check for oligomerisation. The electrical properties of ClyA oligomers were then screened in planar lipid bilayers.

Purification of Evolved ClyA Nanopores.

ClyA was expressed in E. Cloni® EXPRESS BL21 (DE3) cells by using a pT7 plasmid. Monomers were purified by using Ni-NTA affinity chromatography and oligomerized in the presence of 0.2% β-dodecyl maltoside (GLYCON Biochemicals GmbH).

Electrical Recordings.

Ionic currents were measured by recording from planar bilayers formed from diphytanoyl-sn-glycero-3-phosphocholine (Avanti Polar Upids, Alabaster, Ala.). Currents were measured with Ag/AgCl electrodes by using a patch-clamp amplifier (Axopatch 200B, Axon Instruments, Foster City, Calif.).[18]

Construction of ClyA Libraries by Error-Prone PCR.

Libraries were constructed by amplifying the ClyA genes from plasmid DNA using T7 promoter and T7 terminator primers (Table 3). In the first mutagenesis round we used as a template a plasmid containing the synthetic gene encoding for ClyA-SS from Salmonella Typhi. From the second mutagenesis round we used the DNA plasmids that were derived from the previous round of selection. In ClyA-SS, the WT sequence was modified by the substitution of the two Cys residues (positions 87 and 285) with Ser and by the attachment of DNA encoding a Gly-Ser-Ser linker followed by a C-terminal hexahistidine tag.[7a]

DNA amplification was performed by error prone PCR: 400 μL of the PCR mix (200 μl of REDTaq ReadyMix, 8 μM final concentration of forward and reverse primers, ~400 ng of plasmid template and ddH$_2$O up to 400 μl) was split into 8 reaction mixtures containing 0-0.2 mM of MnCl$_2$ and cycled for 27 times (pre-incubation at 95° C. for 3 min, then cycling: denaturation at 95° C. for 15 sec, annealing at 55° C. for 15 sec, extension at 72° C. for 3 min). These conditions typically yielded 1-4 mutations per gene in the final library. The PCR products were pooled together, gel purified (QIAquick Gel Extraction Kit, Qiagen) and cloned into a pT7 expression plasmid (pT7-SC1) by MEGAWHOP procedure:[19] ~500 ng of the purified PCR product was mixed with ~300 ng of ClyA-SS circular DNA template and the amplification was carried out with Phire Hot Start II DNA polymerase (Finnzymes) in 50 μL final volume (pre-incubation at 98° C. for 30 s, then cycling: denaturation at 98° C. for 5 sec, extension at 72° C. for 1.5 min for 30 cycles). The circular template was eliminated by incubation with Dpn I (1 FDU) for 2 hr at 37° C. The resulted mixture was desalted by dialysis against agarose gel (2.5% agarose in Milli-Q water) and transformed into E. Cloni® 10G cells (Lucigen) by electroporation. The transformed bacteria were grown overnight at 37°C. on ampicillin (100 μg/ml) LB agar plates typically resulting in >10$^5$ colonies, and were harvested for library plasmid DNA preparation.

Construction of Saturation Mutagenesis Library at Position 87 of Evolved ClyA

In order to have a library containing cysteine-free ClyA variants, the gene encoding for 4ClyA4 (Table 2) was amplified using the 87NNS primer (containing a degenerate codon at position 87 encoding for the complete set of amino acids, Table 3) and T7 terminator primers. PCR conditions: 0.3 mL final volume of PCR mix (ReadyMix™), containing ~400 ng of template plasmid, cycled for 30 times (pre-incubation at 95° C. for 3 min, then cycling: denaturation at 95° C. for 15 sec, annealing at 55° C. for 15 sec, extension at 72° C. for 3 min). The resulting PCR product was cloned into pT7 expression plasmid by MEGAWHOP procedure using 4ClyA4 circular template (see above).

Construction of the ClyA-WT

ClyA-SS gene was amplified using 87C and 285C primers (Table 3). PCR conditions: 0.3 mL final volume of PCR mix (150 μl of REDTaq ReadyMix, 6 μM of forward and reverse primers, ~400 ng of template plasmid), cycled for 27 times (pre-incubation at 95° C. for 3 min, then cycling: denaturation at 95° C. for 15 sec, annealing at 55° C. for 15 sec, extension at 72° C. for 3 min). The resulting PCR product was cloned into pT7 expression plasmid by the MEGAWHOP procedure described above, using ClyA-SS circular template.

Screening of ClyA Libraries and Hemolytic Assay

Since ClyA-SS displays "border of detection" hemolytic activity, during the first two rounds of the mutagenesis libraries were only screened for activity on Brucella Agar with 5% Horse Blood. From the third selection round, colonies displaying hemolytic activity on *Brucella* Agar were further screened for hemolytic activity on horse erythrocytes from the crude lysate after overexpression. The goal of this work was to obtain ClyA variants that oligomerise well in β-dodyl maltoside (DDM) and form nanopores with low electrical noise and uniform unitary conductance in lipid bilayers. Therefore, screening for hemolytic activity alone could not serve as the sole criteria for selection of such variants (for example WT-ClyA is very hemolytically active, but shows non-uniform unitary current distribution). Thus, from the 4th round, proteins from the crude lysate were purified by Ni-NTA affinity chromatography and the oligomerisation of ClyA was tested on BN-PAGE after incubation in DDM. ClyA nanopores that oligomerised well were then tested in planar lipid bilayers (with particular stress on uniformity of formed channels, low electrical noise and stability at high applied potentials).

Screening for Hemolytic Activity on *Brucella* Horse Blood Agar Plates

After the plasmid DNA was electroporated into E. Cloni® EXPRESS BL21 (DE3) cells (Lucigen), transformants were prescreened on *Brucella* Agar with 5% Horse Blood (BBL™, Becton, Dickinson and Company) supplemented with 100 µg/ml ampicillin. Clones displaying hemolytic activity, which was observed by a lytic aura around the colonies after overnight growth at 37° C., were individually grown in 96-deep-wells plates overnight by shaking at 37° C. (0.5 mL 2xYT medium containing 100 µg/mL ampicillin). The obtained cultures were either pooled for preparation of plasmid DNA (QIAprep, Qiagen) that served as a template for the next round (rounds 1 and 2), or used as starters for protein overexpression (rounds 3 to 5).

Screening for Hemolytic Activity of Crude Lysates after ClyA Overexpression

Rounds 3 to 5: 50 µl of the starter cultures from 400-600 clones (see above) were inoculated Into 450 µl of fresh medium in new 96-deep-wells plates and the cultures were grown at 37° C. until $OD_{600}$ ~0.8. Then IPTG (0.5 mM) was added to induce overexpression, and the temperature was reduced to 25° C. for an overnight incubation. Next day, bacteria were harvested by centrifugation at 3000×g for 15 min at 4° C., the supernatant was discarded and pellets were incubated at −70° C. for few a hours to facilitate cell disruption. Then pellets were resuspended in 0.3 mL of lysis buffer (15 mM Tris.HCl pH 7.5, 150 mM NaCl, 1 mM $MgCl_2$, 10 µg/ml lysozyme and 0.2 units/mL DNAse I) and lysed by shaking at 1300 RPM for 30 min at 37° C. 5-30 µL of lysates were then added to 100 uL of ~1% horse erythrocytes suspension. The latter was prepared by centrifuging horse blood (bioMérieux) at 6000×g for 5 mins at 4° C., the pellet was resuspended in 15 mM Tris.HCl pH 7.5, 150 mM NaCl (If the supernatant showed a red color, the solution was centrifuged again and the pellet resuspended in the same buffer). The hemolytic activity was monitored by the decrease in OD at 650 nm over time (~3-10 min intervals, measured using Multiskan GO Microplate Spectrophotometer, Thermo Scientific). The hemolytic activity of the clones was compared with the activity of 2-4 parent clones from the previous round that were grown in the same plates as a reference.

Screening for Oligomerization and Nanopore Formation of Evolved Variants

Rounds 4: 6-12 of the most hemolytically active variants were partially purified from the same lysates that were used for the screening of hemolytic activity by using Ni-NTA affinity chromatography: 0.2 mL of crude lysate containing monomeric ClyA was brought to 1 mL with 15 mM Tris.HCl pH 7.5, 150 mM NaCl supplemented with 1% DDM (to trigger ClyA oligomerization) and 10 mM imidazole, incubated at ambient temperature for 20 min and centrifuged at 20'000×g for 10 min at 4° C. The clarified lysates were allowed to bind to 20 µL (bead volume) of NI-NTA agarose beads (Qiagen) for 1 hr by gentle mixing at 4° C. The unbound fraction were removed by centrifugation at 20'000×g for 10 min at 4° C. (the supernatant was discarded). Finally, oligomerized ClyA proteins were eluted with 50 µl. of 600 mM imidazole in 15 mM Tris.HCl pH 7.5 150 mM NaCl 0.2% DOM. Typically 40 µg of ClyA were supplemented with ~10% glycerol and 1× of NativePAGE™ Running Buffer and 1× Cathode Buffer Additive (Invitrogen™) and then loaded on BN-PAGE (FIG. 7). Variants that formed oligomers on BN-PAGE were then tested in planar lipid bilayers (with particular stress on uniformity of formed channels).

In round 5 the ClyA-CS clones that were subjected to saturation mutagenesis at position 87 were screened in order to obtain a cysteine-less ClyA variant amenable to site-specific chemical modification. Therefore, since that clones containing cysteine at position 87 were expected to show the highest activity, in this round the clones that showed medium to high hemolytic activity in the crude lysates were Isolated. ClyA variants were then partially purified and selected as explained above.

Proteins Overexpression and Purification

E. Cloni® EXPRESS BL21 (DE3) cells were transformed with the pT7 plasmid containing the ClyA gene. Transformants were grown overnight at 37° C. on LB agar plates supplemented with 100 mg/L ampicillin. The resulting colonies were pooled together and innoculated into 50 mL of LB medium containing 100 mg/L of ampicillin. The culture was grown at 37° C., with shaking at 200 rpm, until it reached an $OD_{600}$ of 0.6 to 0.8. The expression of ClyA was then induced by the addition of 0.5 mM IPTG and the growth was continued at 20° C. The next day the bacteria were harvested by centrifugation at 6000×g for 10 min and the pellets were stored at −70° C.

The pellets containing monomeric ClyA were thawed and resuspended in 20 mL of wash buffer (10 mM imidazole, 150 mM NaCl, 15 mM Tris.HCl, pH 7.5), supplemented with 1 mM $MgCl_2$ and 0.05 units/mL of DNAse I and the bacteria were lysed by sonication. The crude lysates were clarified by centrifugation at 6000×g for 20 min and the supernatant was mixed with 200 µL of Ni-NTA resin (Qiagen) pre-equilibrated with wash buffer. After 1 h, the resin was loaded into a column (Micro Bio Spin, Bio-Rad) and washed with ~5 ml of the wash buffer. ClyA was eluted with approximately ~0.5 mL of wash buffer containing 300 mM imidazole. Protein concentration was determined by Bradford assay and the purified proteins were stored at 4° C.

Construct of ClyA Models

The 13mer and 14mer ClyA nanopores were modeled from the 12mer of the crystal structure (PDB code: 2WCD) as follow: A central axis was constructed through the length of the 12mer (ax12), and the distance between the C-alpha atom of residue 114 In the monomer A (114Ca-A) and the ax12 was measured giving the approximate radius of the pore (r12). The distance (d) between the 114Ca-A and the equivalent atom in monomer B (114Ca-B) was used to calculate the approximate circumference of the 12mer (c12=d×12), 13mer (c13=d×13) and 14mer (c14=d×14). The radius of the three oligomers (r12, r13 and r14) was then calculated from the circumference using simple trigonometry. The 12mer, 13mer and 14mer were then built by placing the monomers at distances r12, r13 and r14, respectively, from the central ax and rotated over an angle of 360°/12, 360°/13 and 360°/14, respectively. The 12mer that was built using this method reproduced perfectly the 12mer of the X-ray crystal structure (RMS=0.29 Å), showing the high degree of symmetry and feasibility to construct higher order pores.[20]

The size of the nanopore opening was obtained by increasing the Van der Waals radii of the atoms of ClyA until the pore closed. Then the increased value of the Van der Waals radii was taken as the radius of the pore. The diameter of thrombin was calculated from a sphere corresponding to the measured molecular volume of the protein.[20]

Electrical Recordings in Planar Lipid Bilayers.

The applied potential refers to the potential of the trans electrode. ClyA nanopores were inserted into lipid bilayers from the cis compartment, which was connected to the ground. The two compartments were separated by a 25-µm thick polytetrafluoroethylene film (Goodfellow Cambridge Limited) containing an orifice ~100 µm in diameter. The aperture was pretreated with ~5 µL of 10% hexadecane in pentane and a bilayer was formed by the addition of ~10 µL of 1,2-diphytanoyl-sn-glycero-3-phosphocholine (DPhPC) In pentane (10 mg/mL) to both electrophysiology chambers. Typically, the addition of 0.01-0.1 ng of oligomeric ClyA to the cis compartment (0.5 mL) was sufficient to obtain a single channel. Electrical recordings were carried out in 150 mM NaCl, 15 mM Tris.HCl pH 7.5. The temperature of the recording chamber was maintained at 28° C. by water circulating through a metal case in direct contact with the bottom and sides of the chamber.

Data Recording and Analysis

Electrical signals from planar bilayer recordings were amplified by using an Axopatch 200B patch clamp amplifier (Axon Instruments) and digitized with a Digidata 1440 A/D converter (Axon Instruments). Data were recorded by using Clampex 10.2 software (Molecular Devices) and the subsequent analysis was carried out with Clampfit software (Molecular Devices). Open pore currents and HT blockades were recorded by applying a 10 kHz low-pass Bessel filter and sampling at 50 kHz if not otherwise stated. For unitary channel conductance distributions data collection, traces were further filtered digitally with Gaussian low-pass filter with 200 Hz cutoff. The open pore currents were determined for all Inserted channels at both +35 and −35 mV to ensure that the pore inserted with the correct orientation (the unitary conductance of ClyA is higher at positive applied potentials when reconstituted from the cis side) and values corresponding to −35 mV were used to construct the distributions. Open pore current values ($I_O$) for ClyA and blocked pore current values ($I_B$) for HT were calculated from Gaussian fits to all points histograms (0.3 pA bin size).[3] Histograms for HT and BT blockades were prepared from at least 10 current blockade at least 0.5 s long. The residual current values ($I_{RES}$) were calculated as: $I_{RES\%}=I_B/I_O\%$. When HT produced two current levels within the same blockade, their relative contributions (FIG. 4b, Table 1) were deduced from the area of the peaks obtained from Gaussian fits to the all points histogram.[3] HT blockade lifetimes were calculated by fitting the cumulative distribution of the block dwell times for at least 50 events to a single exponential.[3] From −5 to −20 mV HT blockade lifetimes were measured by applying a cyclic sweep voltage protocol consisting of 3 steps. In the first "capture" step, the applied potential was set to −60 mV for 2 seconds. In the second "release" step the applied potential was decreased to the voltage of interest (−5 to −20 mV) for 2-10 sec where HT released from the pore. Finally in the "regeneration" step the potential was briefly reversed to +35 mV for 0.2 seconds to regenerate a new unblocked open pore state. At least 50 sweeps were averaged and the part of the trace corresponding to release step was fit to single exponential. The duration of the FP blockades (dwell times), which occasionally showed both level 1 and level 2 currents, were distributed over two orders of magnitude and were not fit well with exponential functions. Therefore, median dwell times are quoted for FP. The traces were recorded at a sampling rate of 20 kHz with an internal low-pass Bessel filter set at 5 kHz. The measurements were performed in 150 mM NaCl, 15 mM Tris.HCl, pH 7.5. Graphs were made with Origin (OriginLab Corporation) and the temperature set at 28° C. All values quoted in this work are based on the average of at least three separate recordings, unless otherwise specified.

ClyA Pores for DNA Translocation

DNA Preparation ssDNA molecules were purchased from Integrated DNA Technologies (IDT). 1 was made by PCR where one of the two primers was 5' biotinylated. 3 was formed by incubating two complementary ssDNA molecules, one of which contained a biotin moiety at the 3' end. The DNA hybrid was then purified from the excess ssDNA by affinity chromatography. 5 and 6 were HPLC purified by IDT.

Preparation of ClyA Pores

ClyA was expressed in *E. coli* (DE3) pLysS cells by using a pT7 plasmid. Monomers containing a C-terminal oligohistidine tag were expressed in *E. coli* cells and the soluble fraction purified by Ni-NTA affinity chromatography. ClyA dodecamers were formed by the addition of 0.2% β-dodecyl maltoside (DDM), and were separated from monomers by blue native poly-acrylamide gel electrophoresis. The lowest band of oligomeric ClyA-CS was extracted and stored at 4° C.

ClyA-2 nanopores were prepared by covalently attaching 2 to a ClyA protein where the two WT cysteine residues (positions 87 and 285) were substituted with serine (ClyA-SS), and a cysteine was introduced at position 103 (aspartate in the WT gene; ClyA-SSC$_{103}$). ClyA-SSC$_{103}$ was constructed from ClyA-SS, which also encoded a Gly-Ser-Ser linker followed by a C-terminal hexahistidine tag, by using the megaprimer method[7a] using Phire® Hot Start DNA Polymerase (Finnzymes). The DNA (5'-TTTTTTTTTTATC-TACGAATTCATCAGGGCTAAAGAGTGCAGAGT-TACTTAG-3'), containing a protected thiol group attached to the 5' hydroxyl of the DNA strand via a C6 linker (5ThioMC6-D, IDT), was then conjugated to ClyA-SSC$_{103}$ monomers, purified and oligomerised as described. Purified oligomers were stored at −80° C. in 20% glycerol.

DNA preparation 1 was made by PCR amplification of a pT7-ClyA-WT DNA template using a 5' biotinylated forward primer (bio-5' TAATACGACTCACTATAGGG-3') and a non-biotinylated reverse primer (5'-CATCAGCAG-CACTTTGATATCGCCCACC-3') using Taq DNA Polymerase from REDTaq® ReadyMix™ PCR Reaction Mix (Sigma). After a maximum number of 35 cycles the PCR product of 24 reaction tubes (50 µL each tube) was purified by using a PCR quick purification kit (QIAGEN) and the size of the construct checked by using a 2% agarose gel (TAE buffer). The typical sample concentration was ~200 ng/µL.

3 was formed by incubating a 3' biotinylated ssDNA molecule (5'-GGATGACCTGATCCAGATATTTATTATA-CAGGTCCAGCGCACCGTCAGCCCAATCG-CACTTTTCACAAAAAGA GAGAGAGATCGATTACC-3'-bio, 3a) with a 20% excess of a partially complementary ssDNA (5'-GGTAATCGATCCTCTCTCTTTTGT-GAAAAGTGCGATTGGGCTGACGGTGCGCTGGAC-3', 3b, Table 4). The temperature was brought to 95° C. for one minute and then decreased stepwise to room temperature. At around the estimated annealing temperature, the temperature was decreased in 2° C. steps, each held for one minute. The hybrid DNA was then purified from the excess of ssDNA by affinity chromatography, using a biotin-binding column containing monomeric avidin immobilised on agarose beads (Thermo Scientific Pierce). 3 was eluted in Biotin Blocking/Elution Buffer according to the protocol. Typically a DNA concentration of ~400 ng/µL was obtained. The size of the dsDNA was checked by using a 2% agarose gel in TAE buffer. The purified dsDNA was stored at −20° C. in the presence of 1 µM EDTA.

Electrical Recordings

If not otherwise specified, the signal was collected at sampling rate of 50 KHz using a 10 kHz Bessel filter. The lipid bilayer was formed by the addition of 1 to 2 µL of a 10% solution of 1,2-diphytanoyl-sn-glycero-3-phosphocholine (DPhPC) in pentane (w/v). The electrical potential was applied by using Ag/AgCl electrodes submerged in agar bridges (3% w/v low melt agarose in 2.5 M NaCl buffer). The applied potential refers to the potential of the working electrode connected to the trans compartment of the chamber. ClyA nanopore solutions (0.01-0.1 ng) were added to the cis compartment, which was connected to the ground electrode. After the Insertion of a single channel, excess protein was removed by several cycles of perfusion. Electrical recordings were carried out in 2.5 M NaCl, 15 mM Tris.HCl pH 8.0, at 22° C. The errors indicate the standard deviation from the average for at least three independent repeats, which are indicated with the letter n.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES 1. (a) Kasianowicz, J. J.; Brandin, E.; Branton, D.; Deamer, D. W., Characterization of individual polynucleotide molecules using a membrane channel. Proc Natl Acad Sci USA 1996, 93 (24), 13770-3; (b) Vercoutere, W.; Winters-Hilt, S.; Olsen, H.; Deamer, D.; Haussler, D.; Akeson, M., Rapid discrimination among individual DNA hairpin molecules at single-nucleotide resolution using an Ion channel. Nat Biotechnol 2001, 19 (3), 248-52; (c) Howorka, S.; Cheley, S.; Bayley, H., Sequence-specific detection of individual DNA strands using engineered nanopores. Nat Biotechnol 2001, 19 (7), 636-9.
2. (a) Dekker, C., Solid-state nanopores. Nat Nanotechnol 2007, 2 (4), 209-15; (b) Li, J.; Stein, D.; McMullan, C.; Branton, D.; Aziz, M. J.; Golovchenko, J. A., Ion-beam sculpting at nanometre length scales. Nature 2001, 412 (6843), 166-9.
3. (a) Wei, R.; Martin, T. G.; Rant, U.; Dietz, H., DNA origami gatekeepers for solid-state nanopores. Angew Chem Int Ed Engl 2012, 51 (20), 4864-7; (b) Bell, N. A.; Engst, C. R.; Ablay, M.; Divitini, G.; Ducati, C.; Liedl, T.; Keyser, U. F., DNA origami nanopores. Nano Lett 2012, 12 (1), 512-7; (c) Langecker, M.; Arnaut, V.; Martin, T. G.; List, J.; Renner, S.; Mayer, M.; Dietz, H.; Simmel, F. C., Synthetic lipid membrane channels formed by designed DNA nanostructures. Science 2012, 338 (6109), 932-6.
4. Hall; Scott, A.; Rotem, D.; Mehta, K.; Bayley, H.; Dekker, C., Hybrid pore formation by directed insertion of alpha hemolysin into solid-state nanopores. Nature Nanotechnology 2011, In press.
5. Venkatesan, B. M.; Bashir, R., Nanopore sensors for nucleic acid analysis. Nat Nanotechnol 2011, 6 (10), 615-24.
6. (a) Jung, Y.; Bayley, H.; Movileanu, L., Temperature-responsive protein pores. J Am Chem Soc 2006, 128 (47), 15332-40; (b) Heinz, C.; Engelhardt, H.; Niederweis, M., The core of the tetrameric mycobacterial porin MspA is an extremely stable beta-sheet domain. J Biol Chem 2003, 278 (10), 8678-85.
7. (a) Soskine, M.; Biesemans, A.; Moeyaert, B.; Cheley, S.; Bayley, H.; Maglia, G., An Engineered ClyA Nanopore Detects Folded Target Proteins by Selective External Association and Pore Entry. Nano Lett 2012, 12 (9), 4895-900; (b) Franceschini, L; Mikhailova, E.; Bayley, H.; Maglia, G., Nucleobase recognition at alkaline pH and apparent pKa of single DNA bases immobilised within a biological nanopore. Chem Commun (Camb) 2012, 48 (10), 1520-2; (c) Maglia, M.; Henricus, M.; Wyss, R.; Li, Q.; Cheley, S.; Bayley, H., DNA strands from denatured duplexes are translocated through engineered protein nanopores at alkaline pH. Nano Letters 2009, 9, 3831-3836.
8. (a) Pastoriza-Gallego, M.; Oukhaled, G.; Mathe, J.; Thiebot, B.; Betton, J. M.; Auvray, L. C.; Pelta, J., Urea denaturation of alpha-hemolysin pore inserted in planar lipid bilayer detected by single nanopore recording: Loss of structural asymmetry. FEBS Lett 2007, 581 (18), 3371-3376; (b) Japrung, D.; Henricus, M.; Li, Q. H.; Maglia, G.; Bayley, H., Urea Facilitates the Translocation of Single-Stranded DNA and RNA Through the alpha-Hemolysin Nanopore. Biophysical Journal 2010, 98 (9), 1856-1863.
9. (a) Mohammad, M. M.; Iyer, R.; Howard, K. R.; McPike, M. P.; Borer, P. N.; Movileanu, L., Engineering a Rigid Protein Tunnel for Biomolecular Detection. J Am Chem Soc 2012; (b) Bikwemu, R.; Wolfe, A. J.; Xing, X.; Movileanu, L, Facilitated translocation of polypeptides through a single nanopore. J Phys Condens Matter 2010, 22 (45), 454117; (c) Wolfe, A. J.; Mohammad, M. M.; Cheley, S.; Bayley, H.; Movileanu, L., Catalyzing the translocation of polypeptides through attractive interactions. Journal of the American Chemical Society 2007, 129 (45), 14034-14041; (d) Movileanu, L.; Schmittschmitt, J. P.; Scholtz, J. M.; Bayley, H., Interactions of peptides with a protein pore. Biophys J 2005, 89 (2), 1030-45; (e) Payet, L.; Martinho, M.; Pastoriza- Gallego, M.; Betton, J. M.; Auvray, L; Pelta, J.; Mathe, J., Thermal unfolding of proteins probed at the single molecule level using nanopores. Anal Chem 2012, 84 (9), 4071-6; (f) Pastoriza-Gallego, M.; Rabah, L; Gibrat, G.; Thiebot, B.; van der Goot, F. G.; Auvray, L; Betton, J. M.; Pelta, J., Dynamics of unfolded protein transport through an aerolysin pore. J Am Chem Soc 2011, 133 (9), 2923-31; (g) Oukhaled, G.; Mathé, J.; Biance, A.-L.; Bacri, L.; Betton, J.-M.; Lairez, D.; Pelta, J.; Auvray, L., Unfolding of Proteins and Long Transient Conformations Detected by Single Nanopore Recording. Phys. Rev. Lett. 2007, 98, 158101; (h) Stefureac, R. I.; Kachayev, A.; Lee, J. S., Modulation of the translocation of peptides through nanopores by the application of an AC electric field. Chem Commun (Camb) 2012, 48 (13), 1928-30; (i) Stefureac, R. I.; Lee, J. S., Nanopore analysis of the folding of zinc fingers. Small 2008, 4 (10), 1646-50; (j) Stefureac, R.; Waldner, L; Howard, P.; Lee, J. S., Nanopore analysis of a small 86-residue protein. Small 2008, 4 (1), 59-63; (k) Stefureac, R.; Long, Y. T.; Kraatz, H. B.; Howard, P.; Lee, J. S., Transport of alpha-helical peptides through alpha-hemolysin and aerolysin pores. Biochemistry 2006, 45 (30), 9172-9.

10. (a) Firnkes, M.; Pedone, D.; Knezevic, J.; Doblinger, M.; Rant, U., Electrically Facilitated Translocations of Proteins through Silicon Nitride Nanopores: Conjoint and Competitive Action of Diffusion, Electrophoresis, and Electroosmosis. Nano Letters 2010, 10 (6), 2162-2167; (b) Plesa, C.; Kowalczyk, S. W.; Zinsmeester, R.; Grosberg, A. Y.; Rabin, Y.; Dekker, C., Fast Translocation of Proteins through Solid State Nanopores. Nano Lett 2013; (c) Niedzwiecki, D. J.; Grazul, J.; Movileanu, L, Single-Molecule Observation of Protein Adsorption onto an Inorganic Surface. Journal of the American Chemical Society 2010, 132 (31), 10816-10822; (d) Fologea, D.; Ledden, B.; McNabb, D. S.; U, J. L, Electrical characterization of protein molecules by a solid-state nanopore. Applied Physics Letters 2007, 91 (5); (e) Han, A.; Creus, M.; Schurmann, G.; Under, V.; Ward, T. R.; de Rooij, N. F.; Staufer, U., Label-free detection of single protein molecules and protein-protein interactions using synthetic nanopores. Anal Chem 2008, 80 (12), 4651-8; (f) Stefureac, R. I.; Trivedi, D.; Marziali, A.; Lee, J. S., Evidence that small proteins translocate through silicon nitride pores in a folded conformation. J Phys Condens Matter 2010, 22 (45), 454133.

12. Eifier, N.; Vetsch, M.; Gregorini, M.; Ringler, P.; Chami, M.; Philippsen, A.; Fritz, A.; Muller, S. A.; Glockshuber, R.; Engel, A.; Grauschopf, U., Cytotoxin ClyA from *Escherichia coli* assembles to a 13-meric pore independent of its redox-state. EMBO J 2006, 25 (11), 2652-61.

13. (a) Pogoryelov, D.; Klyszejko, A. L.; Krasnoselska, G. O.; Heller, E. M.; Leone, V.; Langer, J. D.; Vonck, J.; Muller, D. J.; Faraldo-Gomez, J. D.; Meler, T., Engineering rotor ring stoichiometries in the ATP synthase. Proc Natl Acad Sci USA 2012, 109 (25), E1599-608; (b) Bayfield, O. W.; Chen, C. S.; Patterson, A. R.; Luan, W.; Smits, C.; Gollnick, P.; Antson, A. A., Trp RNA-binding attenuation protein: modifying symmetry and stability of a circular oligomer. PLoS One 2012, 7 (9), e44309.

14. Niedzwiecki, D. J.; Iyer, R.; Borer, P. N.; Movileanu, L, Sampling a Biomarker of the Human Immunodeficiency Virus across a Synthetic Nanopore. ACS Nano 2013.

15. (a) Clarke, J.; Wu, H.; Jayasinghe, L; Patel, A.; Reid, S.; Bayley, H., Continuous base identification for single-molecule nanopore DNA sequencing. Nature Nanotechnology 2009, 4, 265-270; (b) Rincon-Restrepo, M.; Mikhailova, E.; Bayley, H.; Maglia, G., Controlled Translocation of Individual DNA Molecules through Protein Nanopores with Engineered Molecular Brakes. Nano Lett 2011, 11(2), 746-50.

16. (a) Freedman, K. J.; Jurgens, M.; Prabhu, A.; Ahn, C. W.; Jemth, P.; Edel, J. B.; Kim, M. J., Chemical, thermal, and electric field induced unfolding of single protein molecules studied using nanopores. Anal Chem 2011, 83 (13), 5137-44; (b) Niedzwiecki, D. J.; Movileanu, L, Monitoring protein adsorption with solid-state nanopores. J Vis Exp 2011, (58); (c) Talaga, D. S.; Li, J., Single-molecule protein unfolding in solid state nanopores. J Am Chem Soc 2009, 131 (26), 9287-97.

17. Mueller, M.; Grauschopf, U.; Maier, T.; Glockshuber, R.; Ban, N., The structure of a cytolytic alpha-helical toxin pore reveals its assembly mechanism. Nature 2009, 459 (7247), 726-U135.

18. Maglia, G.; Heron, A. J.; Stoddart, D.; Japrung, D.; Bayley, H., Analysis of Single Nucleic Acid Molecules with Protein Nanopores. Methods in Enzymology, Vol 475: Single Molecule Tools, Pt B 2010, 474, 591-623.

19. Miyazaki, K., MEGAWHOP cloning: a method of creating random mutagenesis libraries via megaprimer PCR of whole plasmids. Methods Enzymol 2011, 498, 399-406.

20. Delhaise, P.; Bardiaux, M.; Demaeyer, M.; Prevost, M.; Vanbelle, D.; Donneux, J.; Lasters, I.; Vancustem, E.; Alard, P.; Wodak, S. J., The Brugel Package—toward Computer-Aided-Design of Macromolecules. J Mol Graphics 1988, 6 (4), 219-219.

21. King, N. P. et al. Computational design of self-assembling protein nanomaterials with atomic level accuracy. Science 336, 1171-1174 (2012).

22. Ackermann, D. et al. A double-stranded DNA rotaxane. Nat Nanotechnol 5, 436-442 (2010).

23. Sanchez-Quesada, J., Saghatelian, A., Cheley, S., Bayley, H. & Ghadiri, M. R. Single DNA rotaxanes of a transmembrane pore protein. Angew Chem Int Ed Engl 43, 3063-3067 (2004).

24. Meller, A., Nivon, L. & Branton, D. Voltage-driven DNA translocations through a nanopore. Phys Rev Lett 86, 3435-3438 (2001).

25. Henrickson, S. E., Misakian, M., Robertson, B. & Kasianowicz, J. J. Driven DNA transport into an asymmetric nanometer-scale pore. Phys Rev Lett 85, 3057-3060 (2000).

26. Maglia, G., Rincon Restrepo, M., Mikhailova, E. & Bayley, H. Enhanced translocation of single DNA molecules through α-hemolysin nanopores by manipulation of internal charge. Proc Natl Acad Sci USA 105, 19720-19725 (2008).

27. Butler, T. Z., Pavlenok, M., Derrington, I. M., Niederweis, M. & Gundlach, J. H. Single-molecule DNA detection with an engineered MspA protein nanopore. Proc Natl Acad Sci USA 105, 20647-20652 (2008).

28. Wanunu, M., Morrison, W., Rabin, Y., Grosberg, A. Y. & Meller, A. Electrostatic focusing of unlabelled DNA into nanoscale pores using a salt gradient. Nat Nanotechnol 5, 160-165 (2010).

Tables

TABLE 1

Parameters for ClyA-SS and the three types of ClyA-CS nanopores. The diameter of Type I ClyA-SS and ClyA-CS was taken from the crystal structure of *E. coli* ClyA. The diameter of Type II and Type III ClyA-CS was measured from models that were created by adding one (Type II) or two (Type III) subunits to the structure of the 12mer ClyA (crystal structure) as described in the supplementary information. The diameters of the nanopores were determined including the Van der Waals radii of the atoms (supplementary information). Errors are given as standard deviations.

| Parameters | Type I* ClyA-SS | Type I ClyA-CS | Type II ClyA-CS | Type III ClyA-CS |
|---|---|---|---|---|
| Trans diameter, nm | 3.3 | 3.3 | 3.7 | 4.2 |
| Cis diameter, nm | 5.5 | 5.5 | 5.9 | 6.5 |
| Nanopore conductance at −35 mV, nS | 1.8 ± 0.1 | 1.78 ± 0.04 | 2.19 ± 0.09 | 2.81 ± 0.11 |
| Nanopore conductance at −150 mV, nS | NA | 1.50 ± 0.03 | 1.85 ± 0.06 | NA |
| HT Occupancy of L2 at −35 mV, % | 22 ± 5 | 30 ± 10 | 96 ± 2 | 100 |
| HT Level 1 at −35 mV, $I_{RES}$ % | 56 ± 1 | 56 ± 1 | 68 ± 1 | NA |
| HT Level 2 at −35 mV, $I_{RES}$ % | 23 ± 1 | 23 ± 3 | 31 ± 1 | 32 ± 9 |
| HT Occupancy of L2 at −150 mV, % | NA | 100 | 100 | NA |
| HT Level 2 (−150 mV), $I_{RES}$, % | NA | 23 ± 2 | 31 ± 5 | NA |
| HT Dwell time at −150 mV, ms | NA | 1.0 ± 0.4 | 235 ± 186 | NA |

(*Data taken from[7a])

TABLE 2

Mutations accumulated during the directed evolution rounds of the ClyA-SS gene.

| Round | Name | Clone ID | Sequence changes relative to WT-ClyA |
|---|---|---|---|
| 0 | ClyA-SS | dSClyA | C87S, C285S |
| 3 | | 3ClyA1 | C87S, F166Y, K230R, C285S |
| 3 | | 3ClyA2 | Q73R, F166Y, C285S |
| 3 | | 3ClyA3 | Q33R, Q56H, C87S, D122G, C285S |
| 4 | | 4ClyA1 | I4T, N128S, S145I, C285S |
| 4 | | 4ClyA2 | S110I, C285S, F166Y, T223A |
| 4 | | 4ClyA3 | T39I, C285S, F166Y, K230R |
| 4 | ClyA-CS | 4ClyA4 | L99Q, E103G, F166Y, C285S, K294R |
| 4 | | 4ClyA5 | I4T, Q73R, C285S |
| 4 | | 4ClyA6 | Q73R, F166Y, C285S |
| 5 | | 5ClyA1 | C87A, L99Q, E103G, C285S, F166Y, N220S, Q289R, K294R, H307Y |
| 5 | | 5ClyA2 | C87A, L99Q, E103G, C285S, F166Y, Q289R, K294R, H307Y |
| 5 | ClyA-AS | 5Cly43 | C87A, L99Q, E103G, C285S, F166Y, I203V, K294R, H307Y |

TABLE 3

Primers: N stands for A, G, C, or T; S is G or C, thus NNS codon encodes for the full set of amino acids.

| Name | Sequence | SEQ ID NO |
|---|---|---|
| 87NNS | GAAGCTACCCAAACGGTTTACGAATGGNNSGGTGTGGTTACCCAGCTGCTG | 17 |
| T7 promoter | TAATACGACTCACTATAGGG | 18 |
| T7 terminator | GCTAGTTATTGCTCAGCGG | 19 |
| 87C | GTTTACGAATGGTGTGGTGTGGTTACCCAG | 20 |
| 285C | CGCTGCTGATATTCATTACAGGTATTAATCATTTTC | 21 |

TABLE 4

Summary of DNA molecules used in this work. 1 was prepared by PCR as described in methods. 3 was formed by incubating 3a with a 20% excess of 3b and purified by affinity chromatogtraphy as described in methods. The complimentary sequences in the two DNA strands are shown in italics.

|   | Name | DNA sequence | SEQ ID NO |
|---|------|--------------|-----------|
| 1 | 1a | Bio-5'TAATACGACTCACTATAGGGAGACCACAACGGTTTCCCTCTAGAAATAATTT TGTTTAACTTTAAGAAGGAGATATACATATGACGGGTATCTTTGCGGAACAGAC GGTGGAAGTTGTGAAAAGTGCGATTGAAACGGCTGACGGTGCGCTGGACCTGTA TAATAAATATCTGGATCAGGTCATCCCGTGGAAAACCTTTGACGAAACGATTAA AGAACTGAGCCGTTTCAAACAGGAATACAGTCAAGAAGCGTCCGTCCTGGTGGG CGATATCAAAGTGCTSCTGATG3' | 7 |
|   | 1b | 5'CATCAGCAGCACTTTGATATCGCCCACCAGGACGGACGCTTCTTGACTGTAT TCCTGTTTGAAACGGCTCAGTTCTTTAATCGTTTCGTCAAAGGTTTTCCACGGG ATGACCTGATCCAGATATTTATTATACAGGTCCAGCGCACCGTCAGCCGTTTCA ATCGCACTTTTCACAACTTCCACCGTCTGTTCCGCAAAGATACCCGTCATATGT ATATCTCCTTCTTAAAGTTAAACAAAATTATTTCTAGAGGGAAACCGTTGTGGT CTCCCTATAGTGAGTCGTATTA3' | 8 |
| 2 |  | 5'TTTTTTTTTATCTACGAATTCATCAGGGCTAAAGAGTGCAGAGTTACTTAG3' | 9 |
| 3 | 3a | 5'GGATGACCTGATCCAGATATTTATTATAC*AGGTCCAGCGCACCGTCAGCCCA ATCGCACTTTTCACAAAAAGAGAGAGATCGATTACC*3'-bio | 10 |
|   | 3b | 5'*GGTAATCGATCTCTCTCTCTTTTTGTGAAAAGTGCGATTGGGCTGACGGTGC GCTGGAC*-3' | 11 |
| 4 |  | 5'AATAAATATCTGGATCAGGTCATCCCTAAGTAACTCTGCAC3' | 12 |
| 5a |  | 5'GGATGACCTGATCCAGATATTTATTATACAGGTCCAGCGCACCGTCAGCCCA ATCGCACTTTTCACAAAAAGAGAGAGATCGATTACC3'bio | 13 |
| 5b |  | 5'GGTAATCGATCTCTCTCTCTTTTTGTGAAAAGTGCGATTGGGCTGACGGTGC GCTGGACCTGTATAATAAATATCTGGATCAGGTCATCC3' | 14 |
| 6 |  | 5'GCCCTATATTATCAGGTCATCCCTAAGTAACTCTGCA3' | 15 |
| 7 |  | 5'TGCAGAGTTACTTAGGGATGACCTGATAATATAGGGC3' | 16 |

| Description | Sequence | SEQ ID NO |
|---|---|---|
| Protein sequence for S. typhi ClyA (ClyA-WT) | MIMTGIFAEQTVEWKSAIETADGALDLYNKYLDQVIPWKTFDETIKEL SRFKQEYSQEASVLVGDIKVLLMDSQDKYFEATQTVYEWCGVVTQLLS AYILLFDEYNEKKASAQKDILIRILDDGVKKLNEAQKSLLTSSQSFNNASG KLLALDSQLTNDFSEKSSYFQSQVDRIRKEAYAGAAAGIVAGPFGLIISYS IAAGVIEGKLIPELNNRLKTVQNFFTSLSATVKQANKDIDAAKLKLATEIA AIGEIKTETETTRFYVDYDDLMLSLLKGAAKKMINTCNEYQQRHGKKTL FEVPDV | SEQ ID NO: 1 |
| Protein sequence for ClyA with C285S substitution (ClyA-CS) | MTGIFAEQTVEVVKSAIETADGALDLYNKYLDQVIPWKTFDETIKELSRF KQEYSQEASVLVGDIKVLLMDSQDKYFEATQTVYEWCGWTQLLSAYI QLFDGYNEKKASAQKDILIRILDDGVKKLNEAQKSLLTSSQSFNNASGKL LALDSQLTNDFSEKSSYYQSQVDRIRKEAYAGAAAGIVAGPFGLIISYSIA AGVIEGKLIPELNNRLKTVQNFFTSLSATVKQANKDIDAAKLKLATEIAAI GEIKTETETTRFYVDYDDLMLSLLKGAAKKMINTSNEYQQRHGRKTLFE VPDVGSSHHHHHH* | SEQ ID NO: 2 |
| Protein sequence for ClyA-AS | MTGIFAEQTVEWKSAIETADGALDLYNKYLDQVIPWKTFDETIKELSRF KQEYSQEASVLVGDIKVLLMDSQDKYFEATQTVYEWAGWTQLLSAYI QLFDGYNEKKASAQKDILIRILDDGVKKLNEAQKSLLTSSQSFNNASGKL LALDSQLTNDFSEKSSYYQSQVDRIRKEAYAGAAAGIVAGPFGLIISYSIA AGVVEGKLIPELNNRLKTVQNFFTSLSATVKQANKDIDAAKLKLATEIAA IGEIKTETETTRFYVDYDDLMLSLLKGAAKKMINTSNEYQQRHGRKTLF EVPDVGSSYHHHHH* | SEQ ID NO: 3 |
| Nucleotide sequence for S. typhi ClyA | CCTGCGTAGATAAGCAGGAAGCAGGCAGTATTTCCAGCTTCTGGAA TGTTAAAGCTACAAAAGTTGTCTGGAGGTAATAGGTAAGAATACTT TATAAAACAGGTACTTAATTGCAAmATATATTTAAAGAGGCAAAT GATTATGACCGGAATATTTGCAGAACAAACTGTAGAGGTAGTTAAA AGCGCGATCGAAACCGCAGATGGGGCATTAGATCTTTATAACAAAT ACCTCGACCAGGTCATCCCTGGAAGACCTTTGATGAAACCATAAA AGAGTTAAGCCGTTTTAAACAGGAGTACTCGCAGGAAGCTTCTGTT TTAGTTGGTGATATTAAAGTTTTGCTTATGGACAGCCAGGACAAGT ATTTTGAAGCGACACAAACTGTTTATGAATGGTGTGGTGTCGTGAC GCAATTACTCTCAGCGTATATTTTACTATTTGATGAATATAATGAGA | SEQ ID NO: 4 |

-continued

| Description | Sequence | SEQ ID NO |
|---|---|---|
| | AAAAAGCATCAGCCCAGAAAGACATTCTCATTAGGATATTAGATGA<br>TGGTGTCAAGAAACTGAATGAAGCGCAAAAATCTCTCCTGACAAGT<br>TCACAAAGTTTCAACAACGCTTCCGGAAAACTGCTGGCATTAGATA<br>GCCAGTTAACTAATGATTTTTCGGAAAAAAGTAGTTATTTCCAGTCA<br>CAGGTGGATAGAATTCGTAAGGAAGCTTATGCCGGTGCTGCAGCC<br>GGCATAGTCGCCGGTCCGTTTGGATTAATTATTTCCTATTCTATTGCT<br>GCGGGCGTGATTGAAGGGAAATTGATTCCAGAATTGAATAACAGG<br>CTAAAAACAGTGCAAAATTTCTTTACTAGCTTATCAGCTACAGTGAA<br>ACAAGCGAATAAAGATATCGATGCGGCAAAATTGAAATTAGCCACT<br>GAAATAGCAGCAATTGGGGAGATAAAAACGGAAACCGAAACAACC<br>AGATTCTACGTTGATTATGATGATTTAATGCTTTCTTTATTAAAAGG<br>AGCTGCAAAGAAAATGATTAACACCTGTAATGAATACCAACAAAGA<br>CACGGTAAGAAGACGCTTTTCGAGGTTCCTGACGTCTGATACATTTT<br>CATTCGATCTGTGTACTTTTAACGCCCGATAGCGTAAAGAAAATGA<br>GAGACGGAGAAAAAGCGATATTCAACAGCCCGATAAACAAGAGTC<br>GTTACCGGGCTGACGAGGTTATCAGGCGTTAAGCTGGTAG | |
| Nucleotide sequence for ClyA with C285S substitution (ClyA-CS) | ATGACGGGTATCTTTGCGGAACAGACGGTGGAAGTTGTGAAAAGT<br>GCGATTGAAACGGCTGACGGTGCGCTGGACCTGTATAATAAATATC<br>TGGATCAGGTCATCCCGTGGAAAACCTTTGACGAAACGATTAAAGA<br>ACTGAGCCGTTTCAAACAGGAATACAGTCAAGAAGCGTCCGTCCTG<br>GTGGGCGATATCAAAGTGCTGCTGATGGATTCTCAGGACAAATATT<br>TTGAAGCTACCCAAACGGTTTACGAATGGTGTGGTGTGGTTACCCA<br>GCTGCTGTCCGCATATATTCAGCTGTTCGATGGATACAACGAGAAA<br>AAAGCGAGCGCGCAGAAAGACATTCTGATCCGCATTCTGGATGACG<br>GCGTGAAAAAACTGAATGAAGCCCAGAAATCGCTGCTGACCAGCTC<br>TCAATCATTTAACAATGCCTCGGGTAAACTGCTGGCACTGGATAGCC<br>AGCTGACGAACGACTTTTCTGAAAAAAGTTCCTATTACCAGAGCCA<br>AGTCGATCGTATTCGTAAAGAAGCCTACGCAGGTGCCGCAGCAGGT<br>ATTGTGGCCGGTCCGTTCGGTCTGATTATCTCATATTCGATTGCTGC<br>GGGCGTTATCGAAGGTAAACTGATTCCGGAACTGAACAATCGTCTG<br>AAAACCGTTCAGAACTTTTTCACCAGTCTGTCTGCTACGGTCAAACA<br>AGCGAATAAAGATATCGACGCCGCAAAACTGAAACTGGCCACGGA<br>AATCGCTGCGATTGGCGAAATCAAAACCGAAACGGAAACCACGCG<br>CTTTTATGTTGATTACGATGACCTGATGCTGAGCCTGCTGAAAGGTG<br>CCGCGAAGAAAATGATTAATACCTCTAATGAATATCAGCAGCGTCA<br>CGGTAGAAAAACCCTGTTTGAAGTCCCGGATGTGGGCAGCAGCCAC<br>CACCATCATCACCACTAAAAGCTTGGATCCGGCTGCTAACAAAGCCC<br>GAA | SEQ ID NO: 5 |
| Nucleotide sequence for ClyA-AS | ATGACGGGTATCTTTGCGGAACAGACGGTGGAAGTTGTGAAAAGT<br>GCGATTGAAACGGCTGACGGTGCGCTGGACCTGTATAATAAATATC<br>TGGATCAGGTCATCCCGTGGAAAACCTTTGACGAAACGATTAAAGA<br>ACTGAGCCGTTTCAAACAGGAATACAGTCAAGAAGCGTCCGTCCTA<br>GTGGGCGATATCAAAGTGCTGCTGATGGATTCTCAGGACAAATATT<br>TTGAAGCTACCCAAACGGTTTACGAATGGGCGGGTGTGGTTACCCA<br>GCTGCTGTCCGCATATATTCAGCTGTTCGATGGATACAATGAGAAA<br>AAAGCGAGCGCGCAGAAAGACATTCTGATCCGCATTCTGGATGACG<br>GCGTGAAAAAACTGAATGAAGCCCAGAAATCGCTGCTGACCAGCTC<br>TCAATCATTTAACAATGCCTCGGGTAAACTGCTGGCACTGGATAGCC<br>AGCTGACGAACGACTTTTCTGAAAAAAGTTCCTATTACCAGAGCCA<br>AGTCGATCGTATTCGTAAAGAAGCCTACGCAGGTGCCGCAGCAGGT<br>ATTGTGGCCGGTCCGTTCGGTCTGATTATCTCATATTCAATTGCTGC<br>GGGCGTTGTCGAAGGTAAACTGATTCCGGAACTGAACAATCGTCTG<br>AAAACCGTTCAGAACTTTTTCACCAGTCTGTCTGCTACGGTCAAACA<br>AGCGAATAAAGATATCGACGCCGCAAAACTGAAACTGGCCACGGA<br>AATCGCTGCGATTGGCGAAATCAAAACCGAAACGGAAACCACGCG<br>CTTTTATGTTGATTACGATGACCTGATGCTGAGCCTGCTGAAAGGTG<br>CCGCGAAGAAAATGATTAATACCTCTAATGAATATCAGCAGCGTCA<br>CGGTAGAAAAACCCTGTTTGAAGTCCCGGATGTGGGCAGCAGCTAC<br>CACCATCATCACCACTAAAAGCTT | SEQ ID NO: 6 |

The invention claimed is:

1. A nanopore sensor system comprising:
   i) a fluid-filled compartment separated by a membrane into a first cis chamber and a second trans chamber, wherein the fluid is an ionic solution;
   ii) a ClyA pore inserted in the membrane, wherein the ClyA pore comprises 12 or more ClyA subunits and has a pore lumen of at least 3 nm in diameter, wherein the cis diameter of the pore lumen is at least 5.5 nm and the trans exit of the pore lumen is at least 3.3 nm,
   wherein the each subunit of the ClyA pore comprises a polypeptide represented by an amino acid sequence with at least 80% identity to SEQ ID NO: 1; and
   iii) electrodes configured for generating an electrical potential difference across the membrane to facilitate ionic flow through the ClyA pore from the first chamber to the second chamber.

2. The nanopore sensor system of claim 1 further comprising a ligand in combination with the ClyA pore.

3. The nanopore sensor according to claim 2, wherein the ligand confers selective binding properties to an analyte present in the ionic solution.

4. The nanopore sensor according to claim 3, wherein the ligand is an aptamer.

5. The nanopore sensor according to claim 3, wherein the ligand is selected to bind to a specific target protein analyte.

6. The nanopore sensor according to claim 3, wherein the ligand is an antibody.

7. The nanopore sensor according to claim 3, wherein the ligand is a receptor.

8. The nanopore sensor according to claim 3, wherein the ligand is a peptide.

9. The nanopore sensor according to claim 5, wherein the protein analyte binds within the lumen of the ClyA pore.

10. The nanopore sensor according to claim 5, wherein the protein analyte is a protein with a molecular weight in the range of 15-70 kDa.

11. The nanopore sensor according to claim 9, wherein the protein analyte is a protein with a molecular weight in the range of 15-70 kDa.

12. The nanopore sensor according to claim 1, wherein the lumen of the ClyA pore is modified to alter the size, binding properties, and/or structure of the pore.

13. The nanopore sensor according to claim 2, wherein the ClyA pore is attached to the ligand.

14. The nanopore sensor according to claim 13, wherein the ClyA pore is attached to the ligand via a disulfide linkage.

15. The nanopore sensor according to claim 13, wherein the ClyA pore is attached to the ligand via cross-linking.

16. The nanopore sensor according to claim 13, wherein the ClyA pore is attached to the ligand via chemical ligation.

17. The nanopore sensor according to claim 2, wherein the ClyA pore is not attached to the ligand.

* * * * *

UNITED STATES PATENT AND TRADEMARK OFFICE
CERTIFICATE OF CORRECTION

PATENT NO. : 10,802,015 B2
APPLICATION NO. : 16/521475
DATED : October 13, 2020
INVENTOR(S) : Giovanni Maglia et al.

Page 1 of 1

It is certified that error appears in the above-identified patent and that said Letters Patent is hereby corrected as shown below:

In the Claims

At Column 51, Claim 1, Line 61:
"wherein the each subunit of the ClyA pore comprises a"

Should read:
--wherein each subunit of the ClyA pore comprises a--.

Signed and Sealed this
Eighth Day of December, 2020

Andrei Iancu
*Director of the United States Patent and Trademark Office*

SEQUENCE LISTING

<160> NUMBER OF SEQ ID NOS: 21

<210> SEQ ID NO 1
<211> LENGTH: 305
<212> TYPE: PRT
<213> ORGANISM: Salmonella typhi

<400> SEQUENCE: 1

Met Ile Met Thr Gly Ile Phe Ala Glu Gln Thr Val Glu Val Val Lys
1               5                   10                  15

Ser Ala Ile Glu Thr Ala Asp Gly Ala Leu Asp Leu Tyr Asn Lys Tyr
            20                  25                  30

Leu Asp Gln Val Ile Pro Trp Lys Thr Phe Asp Glu Thr Ile Lys Glu
        35                  40                  45

Leu Ser Arg Phe Lys Gln Glu Tyr Ser Gln Glu Ala Ser Val Leu Val
50                  55                  60

Gly Asp Ile Lys Val Leu Leu Met Asp Ser Asp Lys Tyr Phe Glu
65                  70                  75                  80

Ala Thr Gln Thr Val Tyr Glu Trp Cys Gly Val Val Thr Gln Leu Leu
                85                  90                  95

Ser Ala Tyr Ile Leu Leu Phe Asp Glu Tyr Asn Glu Lys Lys Ala Ser
            100                 105                 110

Ala Gln Lys Asp Ile Leu Ile Arg Ile Leu Asp Asp Gly Val Lys Lys
        115                 120                 125

Leu Asn Glu Ala Gln Lys Ser Leu Leu Thr Ser Ser Gln Ser Phe Asn
130                 135                 140

Asn Ala Ser Gly Lys Leu Leu Ala Leu Asp Ser Gln Leu Thr Asn Asp
145                 150                 155                 160

Phe Ser Glu Lys Ser Ser Tyr Phe Gln Ser Gln Val Asp Arg Ile Arg
                165                 170                 175

Lys Glu Ala Tyr Ala Gly Ala Ala Gly Ile Val Ala Gly Pro Phe
            180                 185                 190

Gly Leu Ile Ile Ser Tyr Ser Ile Ala Ala Gly Val Ile Glu Gly Lys
        195                 200                 205

Leu Ile Pro Glu Leu Asn Asn Arg Leu Lys Thr Val Gln Asn Phe Phe
210                 215                 220

Thr Ser Leu Ser Ala Thr Val Lys Gln Ala Asn Lys Asp Ile Asp Ala
225                 230                 235                 240

Ala Lys Leu Lys Leu Ala Thr Glu Ile Ala Ile Gly Glu Ile Lys
            245                 250                 255

Thr Glu Thr Glu Thr Thr Arg Phe Tyr Val Asp Tyr Asp Asp Leu Met
                260                 265                 270

Leu Ser Leu Leu Lys Gly Ala Ala Lys Lys Met Ile Asn Thr Cys Asn
        275                 280                 285

Glu Tyr Gln Gln Arg His Gly Lys Lys Thr Leu Phe Glu Val Pro Asp
            290                 295                 300

Val
305

<210> SEQ ID NO 2
<211> LENGTH: 312
<212> TYPE: PRT
<213> ORGANISM: Salmonella typhi

<400> SEQUENCE: 2

```
Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60
```

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Gln Leu Phe Asp Gly Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
130                 135                 140

Ser Gly Lys Leu Leu Ala Leu Asp Ser Gln Leu Thr Asn Asp Phe Ser
145                 150                 155                 160

Glu Lys Ser Ser Tyr Tyr Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Ser Asn Glu Tyr
        275                 280                 285

Gln Gln Arg His Gly Arg Lys Thr Leu Phe Glu Val Pro Asp Val Gly
290                 295                 300

Ser Ser His His His His His His
305                 310

<210> SEQ ID NO 3
<211> LENGTH: 312
<212> TYPE: PRT
<213> ORGANISM: Salmonella typhi

<400> SEQUENCE: 3

Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Ala Gly Val Val Thr Gln Leu Leu Ser Ala
                85                  90                  95

Tyr Ile Gln Leu Phe Asp Gly Tyr Asn Glu Lys Lys Ala Ser Ala Gln
            100                 105                 110

Lys Asp Ile Leu Ile Arg Ile Leu Asp Asp Gly Val Lys Lys Leu Asn

```
                115                 120                 125
Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Tyr Gln Ser Gln Val Asp Arg Ile Arg Lys Glu
                165                 170                 175

Ala Tyr Ala Gly Ala Ala Gly Ile Val Ala Gly Pro Phe Gly Leu
                180                 185                 190

Ile Ile Ser Tyr Ser Ile Ala Ala Gly Val Val Glu Gly Lys Leu Ile
                195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
                260                 265                 270

Leu Leu Lys Gly Ala Ala Lys Lys Met Ile Asn Thr Ser Asn Glu Tyr
                275                 280                 285

Gln Gln Arg His Gly Arg Lys Thr Leu Phe Glu Val Pro Asp Val Gly
    290                 295                 300

Ser Ser Tyr His His His His His His
305                 310

<210> SEQ ID NO 4
<211> LENGTH: 1194
<212> TYPE: DNA
<213> ORGANISM: Salmonella typhi

<400> SEQUENCE: 4
cctgcgtaga taagcaggaa gcaggcagta tttccagctt ctggaatgtt aaagctacaa      60
aagttgtctg gaggtaatag gtaagaatac tttataaaac aggtacttaa ttgcaattta     120
tatatttaaa gaggcaaatg attatgaccg gaatatttgc agaacaaact gtagaggtag     180
ttaaaagcgc gatcgaaacc gcagatgggg cattagatct ttataacaaa tacctcgacc     240
aggtcatccc ctggaagacc tttgatgaaa ccataaaaga gttaagccgt tttaaacagg     300
agtactcgca ggaagcttct gttttagttg gtgatattaa gttttgctt atggacagcc     360 aggacaagta ttttgaagcg acacaaactg tttatgaatg gtgtggtgtc gtgacgcaat     420
tactctcagc gtatatttta ctatttgatg aatataatga gaaaaaagca tcagcccaga     480
aagacattct cattaggata ttagatgatg gtgtcaagaa actgaatgaa gcgcaaaaat     540
ctctcctgac aagttcacaa agtttcaaca acgcttccgg aaaactgctg gcattagata     600
gccagttaac taatgatttt tcggaaaaaa gtagttattt ccagtcacag gtggatagaa     660
ttcgtaagga agcttatgcc ggtgctgcag ccggcatagt cgccggtccg tttggattaa     720
ttatttccta ttctattgct gcgggcgtga ttgaagggaa attgattcca gaattgaata     780
acaggctaaa aacagtgcaa aatttcttta ctagcttatc agctacagtg aaacaagcga     840
ataaagatat cgatgcggca aaattgaaat tagccactga aatagcagca attggggaga     900
taaaaacgga aaccgaaaca accagattct acgttgatta tgatgattta atgctttctt     960
tattaaaagg agctgcaaag aaaatgatta cacctgtaa tgaataccaa caaagacacg    1020
```

```
gtaagaagac gcttttcgag gttcctgacg tctgatacat tttcattcga tctgtgtact      1080
tttaacgccc gatagcgtaa agaaaatgag agacggagaa aaagcgatat tcaacagccc      1140
gataaacaag agtcgttacc gggctgacga ggttatcagg cgttaagctg gtag            1194

<210> SEQ ID NO 5
<211> LENGTH: 971
<212> TYPE: DNA
<213> ORGANISM: Salmonella typhi

<400> SEQUENCE: 5
atgacgggta tctttgcgga acagacggtg gaagttgtga aaagtgcgat tgaaacggct        60
gacggtgcgc tggacctgta aataaatat ctggatcagg tcatcccgtg gaaaaccttt       120
gacgaaacga ttaaagaact gagccgtttc aaacaggaat acagtcaaga agcgtccgtc      180
ctggtgggcg atatcaaagt gctgctgatg gattctcagg acaaatattt tgaagctacc      240
caaacggttt acgaatggtg tggtgtggtt acccagctgc tgtccgcata tattcagctg      300
ttcgatggat acaacgagaa aaaagcgagc gcgcagaaag acattctgat ccgcattctg      360
gatgacggcg tgaaaaaact gaatgaagcc cagaaatcgc tgctgaccag ctctcaatca      420
tttaacaatg cctcgggtaa actgctggca ctggatagcc agctgacgaa cgacttttct      480
gaaaaaagtt cctattacca gagccaagtc gatcgtattc gtaaagaagc ctacgcaggt      540
gccgcagcag gtattgtggc cggtccgttc ggtctgatta tctcatattc gattgctgcg      600
ggcgttatcg aaggtaaact gattccggaa ctgaacaatc gtctgaaaac cgttcagaac      660
tttttcacca gtctgtctgc tacggtcaaa caagcgaata agatatcga cgccgcaaaa       720 ctgaaactgg ccacggaaat cgctgcgatt ggcgaaatca aaccgaaac ggaaccacg        780 cgcttttatg ttgattacga tgacctgatg ctgagcctgc tgaaaggtgc cgcgaagaaa      840
atgattaata cctctaatga atatcagcag cgtcacggta gaaaaaccct gtttgaagtc      900
ccggatgtgg gcagcagcca ccaccatcat caccactaaa agcttggatc cggctgctaa      960
caaagcccga a                                                           971

<210> SEQ ID NO 6
<211> LENGTH: 945
<212> TYPE: DNA
<213> ORGANISM: Salmonella typhi

<400> SEQUENCE: 6
atgacgggta tctttgcgga acagacggtg gaagttgtga aaagtgcgat tgaaacggct        60
gacggtgcgc tggacctgta aataaatat ctggatcagg tcatcccgtg gaaaaccttt       120
gacgaaacga ttaaagaact gagccgtttc aaacaggaat acagtcaaga agcgtccgtc      180
ctagtgggcg atatcaaagt gctgctgatg gattctcagg acaaatattt tgaagctacc      240
caaacggttt acgaatgggc gggtgtggtt acccagctgc tgtccgcata tattcagctg      300
ttcgatggat acaatgagaa aaaagcgagc gcgcagaaag acattctgat ccgcattctg      360
gatgacggcg tgaaaaaact gaatgaagcc cagaaatcgc tgctgaccag ctctcaatca      420
tttaacaatg cctcgggtaa actgctggca ctggatagcc agctgacgaa cgacttttct      480
gaaaaaagtt cctattacca gagccaagtc gatcgtattc gtaaagaagc ctacgcaggt      540
gccgcagcag gtattgtggc cggtccgttc ggtctgatta tctcatattc aattgctgcg      600
ggcgttgtcg aaggtaaact gattccggaa ctgaacaatc gtctgaaaac cgttcagaac      660
```

```
tttttcacca gtctgtctgc tacggtcaaa caagcgaata agatatcga cgccgcaaaa        720 ctgaaactgg ccacggaaat cgctgcgatt ggcgaaatca aaaccgaaac ggaaaccacg        780
cgcttttatg ttgattacga tgacctgatg ctgagcctgc tgaaaggtgc cgcgaagaaa       840
atgattaata cctctaatga atatcagcag cgtcacggta gaaaaaccct gtttgaagtc       900
ccggatgtgg gcagcagcta ccaccatcat caccactaaa agctt                       945

<210> SEQ ID NO 7
<211> LENGTH: 290
<212> TYPE: DNA
<213> ORGANISM: Artificial Sequence
<220> FEATURE:
<223> OTHER INFORMATION: Synthetic oligonucleotide

<400> SEQUENCE: 7
taatacgact cactataggg agaccacaac ggtttccctc tagaaataat tttgtttaac        60
tttaagaagg agatatacat atgacgggta tctttgcgga acagacggtg gaagttgtga       120
aaagtgcgat tgaaacggct gacggtgcgc tggacctgta ataaatat ctggatcagg         180 tcatcccgtg gaaaaccttt gacgaaacga ttaaagaact gagccgtttc aaacaggaat       240
acagtcaaga agcgtccgtc ctggtgggcg atatcaaagt gctgctgatg                  290

<210> SEQ ID NO 8
<211> LENGTH: 290
<212> TYPE: DNA
<213> ORGANISM: Artificial Sequence
<220> FEATURE:
<223> OTHER INFORMATION: Synthetic oligonucleotide

<400> SEQUENCE: 8
catcagcagc actttgatat cgcccaccag gacggacgct tcttgactgt attcctgttt        60
gaaacggctc agttctttaa tcgtttcgtc aaaggttttc cacgggatga cctgatccag       120
atatttatta tacaggtcca gcgcaccgtc agccgtttca atcgcacttt tcacaacttc       180
caccgtctgt tccgcaaaga tacccgtcat atgtatatct ccttcttaaa gttaaacaaa       240
attatttcta gagggaaacc gttgtggtct ccctatagtg agtcgtatta                   290

<210> SEQ ID NO 9
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 9
ttttttttta tctacgaatt catcagggct aaagagtgca gagttactta g                 51

<210> SEQ ID NO 10
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 10
ggatgacctg atccagatat ttattataca ggtccagcgc accgtcagcc caatcgcact        60
tttcacaaaa agagagagag atcgattacc                                         90

<210> SEQ ID NO 11
<211> LENGTH: 59
```

```
<212> TYPE: DNA
<213> ORGANISM: Artificial Sequence
<220> FEATURE:
<223> OTHER INFORMATION: Synthetic oligonucleotide

<400> SEQUENCE: 11
ggtaatcgat ctctctctct ttttgtgaaa agtgcgattg ggctgacggt gcgctggac      59

<210> SEQ ID NO 12
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 12
aataaatatc tggatcaggt catccctaag taactctgca c                         41

<210> SEQ ID NO 13
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 13
ggatgacctg atccagatat ttattataca ggtccagcgc accgtcagcc caatcgcact      60
tttcacaaaa agagagagag atcgattacc                                      90

<210> SEQ ID NO 14
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 14
ggtaatcgat ctctctctct ttttgtgaaa agtgcgattg ggctgacggt gcgctggacc      60
tgtataataa atatctggat caggtcatcc                                      90

<210> SEQ ID NO 15
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 15
gccctatatt atcaggtcat ccctaagtaa ctctgca                              37

<210> SEQ ID NO 16
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 16
tgcagagtta cttagggatg acctgataat atagggc                              37

<210> SEQ ID NO 17
<211> LENGTH: 51
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: misc_feature
<222> LOCATION: (28)..(29)
<223> OTHER INFORMATION: n is a, c, g or t

<400> SEQUENCE: 17
gaagctaccc aaacggttta cgaatggnns ggtgtggtta cccagctgct g          51

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
taatacgact cactataggg                                              20

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
gctagttatt gctcagcgg                                               19

<210> SEQ ID NO 20
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 20
gtttacgaat ggtgtggtgt ggttacccag                                   30

<210> SEQ ID NO 21
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 21
cgctgctgat attcattaca ggtattaatc attttc                            36
```